(12) United States Patent
Ho et al.

(10) Patent No.: US 8,247,610 B2
(45) Date of Patent: Aug. 21, 2012

(54) AMINE LINKED MODULATORS OF γ-SECRETASE

(75) Inventors: Chih Yung Ho, Lansdale, PA (US); Yan Zhang, Fort Washington, PA (US); Umar S. M. Maharoof, North Wales, PA (US); John Harrison, Cambridge (GB); Jeremy Major, Cambridge (GB); Svenja Burckhardt, Newmarket (GB); Alison Jones, Cambridge (GB)

(73) Assignees: Janssen Pharmaceutica N.V., Beerse (BE); Cellzome Limited, Cambridge (GB)

( * ) Notice: Subject to any disclaimer, the term of this patent is extended or adjusted under 35 U.S.C. 154(b) by 681 days.

(21) Appl. No.: 12/253,444

(22) Filed: Oct. 17, 2008

(65) Prior Publication Data

US 2009/0105300 A1  Apr. 23, 2009

Related U.S. Application Data

(60) Provisional application No. 60/981,293, filed on Oct. 19, 2007.

(51) Int. Cl.
C07C 211/00 (2006.01)
C07D 213/72 (2006.01)
C07D 213/00 (2006.01)
A61K 31/135 (2006.01)
A61K 31/44 (2006.01)

(52) U.S. Cl. ........ 564/373; 546/304; 546/329; 514/352; 514/649

(58) Field of Classification Search .......................... None
See application file for complete search history.

(56) References Cited

U.S. PATENT DOCUMENTS

| 3,876,636 | A | | 4/1975 | Fauran et al. |
| 4,013,768 | A | * | 3/1977 | Fauran et al. ................. 514/256 |
| 4,252,951 | A | | 2/1981 | Jackson et al. |
| 5,391,817 | A | | 2/1995 | Springer et al. |
| 5,877,399 | A | | 3/1999 | Hsiao et al. |
| 7,825,160 | B2 | | 11/2010 | Wilson et al. |
| 7,897,643 | B2 | | 3/2011 | Ho |
| 7,951,843 | B2 | | 5/2011 | Ho |
| 7,968,725 | B2 | | 6/2011 | Lu |
| 2002/0128319 | A1 | | 9/2002 | Koo et al. |
| 2009/0105275 | A1 | | 4/2009 | Ho |
| 2009/0105288 | A1 | | 4/2009 | Ho |
| 2009/0306392 | A1 | | 12/2009 | Ho |

FOREIGN PATENT DOCUMENTS

| CN | 101903347 | 12/2010 |
| EP | 1650183 | 4/2006 |
| EP | 2212287 | 8/2010 |
| EP | 2215043 | 8/2010 |
| WO | WO 01/78721 A1 | 10/2001 |
| WO | WO 03/008635 A2 | 1/2003 |
| WO | WO 2006/004555 | 1/2006 |
| WO | WO 2006/005554 | 1/2006 |
| WO | WO 2006/008558 | 1/2006 |
| WO | WO 2006/045554 A1 | 5/2006 |
| WO | WO 2007/124351 | 11/2007 |
| WO | WO 2007/124394 A1 | 11/2007 |
| WO | WO 2007/146838 | 12/2007 |
| WO | WO 2009/052126 | 4/2009 |
| WO | WO 2009/052334 | 4/2009 |

OTHER PUBLICATIONS

Shih, I-M., et al Cancer Research, 2007, vol. 67, pp. 1879-1882.*
Vippagunta, S. Adv. Drug Deliv. Rev. 2001, vol. 48, pp. 3-26.*
Silverman, R. "The Organic Chemistry of Drug Design and Drug Action," 2004, Elsevier, pp. 29-32.*
Buchwald, H., et al. "Long-Term, Continuous Intravenous Heparin Administration by an Implantable Infusion Pump in Ambulatory Patients with Recurrent Venous Thrombosis", Surgery 88, p. 507 (1980).
During, M., et al. "Controlled Release of Dopamine from a Polymeric Brain Implant: In Vivo Characterization", Ann. Neurol. 25, p. 351 (1989).
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.
Frautschy, S., et al. "Microglial Response to Amyloid Plaques in APPsw Transgenic Mice", Am. J. of Pathology, VI. 52, No. 1 p. 307 (1998).
Goodson, J., "Medical Applications of Controlled Release", vol. I, Chapter 6, pp. 115 (Table of Contents) (1984).
Howard, M., et al. "Acute Subdural Hematomas: An Age-Dependent Clinical Entity", J. Neurosurgery, vol. 71, p. 858 (1989).
Huffman (Thompson), et al. "The Conversion of Phenols to the Corresponding Aryl Halides Under Mild Conditions", Synthesis No. 4, p. 0547 (2005).
Hsiao, K., et al. "Correlative Memory Deficits, Aβ Elevation and Amyloid Plaques in Transgenic Mice", Science 274, p. 99 (1996).
Ida, N., et al. "Analysis of Heterogeneous βA4 Peptides in Human Cerebrospinal Fluid and Blood by a Newly Developed Sensitive Western Blot Assay", J. Biol. Chem. 271, p. 22908 (1996).

(Continued)

Primary Examiner — Janet Andres
Assistant Examiner — Heidi Reese
(74) Attorney, Agent, or Firm — Woodcok Washburn LLP

(57) ABSTRACT

The present invention relates to compounds of Formula I as shown below, wherein the definitions of A, X, Y, $R^1$ $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

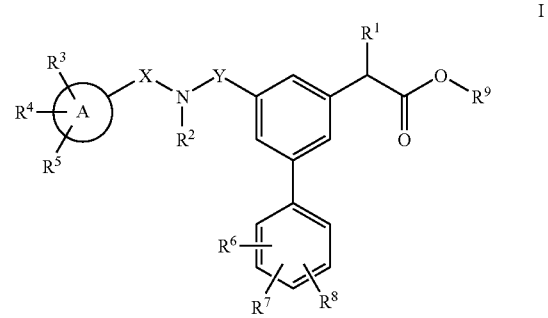

6 Claims, No Drawings

OTHER PUBLICATIONS

Irizarry, M., et al. "APP$_{SW}$ Transgenic Mice Develop Age-Related Aβ Deposits and Neuropil Abnormalities, but no Neuronal Loss in CA1", J. of Neuropathology and Experimental Neurology, vol. 56(9), p. 965 (1997).

Jensen, M., et al. "Quantification of Alzheimer Amyloid Peptides Ending at Residues 40 and 42 by Novel ELISA Systems", Mol. Med. 6 p. 291 (2000).

Kawarabayahsi, T., et al. "Age-Dependent Changes in Brain, CSF, and Plasma Amyloid β Protein in the Tg2576 Transgenic Mouse Model of Alzheimer's Disease", J. Neurosci. 21 p. 372 (2001).

Langer, R., "New Methods of Drug Delivery", Science 249, p. 1527 (1990).

Langer and Peppas "Chemical and Physical Structure of Polymers as Carriers for Controlled Release of Bioactive Agents: A Review", Macromol. Chem. Phys. C23(1), 61-126 (1983).

Larner, A., "Secretases as Therapeutic Targets in Alzheimer's Disease: Patents 2000-2004", Exp. Opinion Ther. Patents 14, p. 1403 (2004).

Lehman, J., et al. "Alterations in β-Amyloid Production and Deposition in Brain Regions of Two Transgenic Models", Neurobiol. Aging 24, p. 645 (2003).

Levy, R., et al. "Inhibition of Calcification of Bioprosthetic Heart Valves by Local Controlled Release Diphosphonate", Science 228, p. 190 (1985).

Lim, G., et al. Ibuprofen Effects on Alzheimer Pathology and Open Field Activity in APPsw Transgenic Mice, Neuroibol. Aging 22, p. 645 (2001).

Lim, G., et al. "Ibuprofen Suppresses Plaque Pathology and Open Field Activity in APPsw Transgenic Mice", Journal of Neuroscience, vol. 20(15), p. 5709 (2000).

Marjaux, E., et al. "γ-Secretase Inhibitors: Still in the Running as Alzheimer's Therapeutics", Drug Discovery Today: Therapeutics Strategies 1, p. 1 (2004).

Morihara, T., et al. "Selective Inhibition of Aβ42 Production b NSAID R-Enantiomer", J., Neurochem. 83, p. 1009 (2002).

Myers, A., et al. "Use of Pseudo Ephedrine as a Practical Chiral Auxiliary for Asymmetric Synthesis", Journal of American Chemical Society, 116 (20), p. 9361 (1994).

Nesmejanow, E., et al. "Immediate Cyanization of Ferricinium Salts", Department for Organic Chemistry of the Moscow State University (Jul. 1960).

Peretto, D., et al. "Synthesis and Biological Activity of Fluriprofen Analogues as Selective Inhibitors of β-Amylid 1-42 Secretion", J. Med. Chem. 48 p. 5705 (2005).

Saudek, C., et al. "A Preliminary Trial of the Programmable Implantable Medication System for Insulin Delivery", N. Engl. J. Med. p. 321 (1989).

Schweisguth, F., et al. Regulation of Notch Signaling Activity, Curr. Biol. 14, p. R129 (2004).

Sefton, M., "Implantable Pumps", CRC Crit. Ref. Biomed. Eng. 14, p. 201 (1987).

Shimizu, K., et al. "Binding of Delta1, Jagged1, and Jagged2 to Notch2 Rapidly Induces Cleavage, Nuclear Translocation, and Hyperphosphorylation of Notch2", Mol. Cell. Biol. 20, p. 6913 (2000).

Steiner, H., "Uncovering γ-Sucretase", Curr. Alzheimer Research 1(3), p. 175 (2004).

Suh, Y., et al. "Novel Potent Antagonists of Transient Receptor Potential Channel, Vanilloid Subfamily Member1: Structure-Activity Relationship of 1,2-Diarylalkyl Thioureas Possessing New Vanilloid Equivalents", Journal of Medicinal Chemistry, 18, p. 7434 (2005).

Thompson(Huffman), et al. "The Conversion of Phenols to the Corresponding Aryl Halides Under Mild Conditions", Synthesis No. 4, p. 0547 (2005).

Vassar, R., et al. "β-Secretese Cleavage of Alzheimer's Amyloid Precursor Protein by the Transmembrane Aspartic Protease BACE", science 286, p. 735 (1999).

Wang, R., et al. "The Profile of Soluble Amyloid β Protein in Cultured Cell Media", J. Biol. Chem. 271 p. 31894 (1996).

Weggen, S., et al. "A Subset of NSAIDs Lower Amylidogenic Aβ42 Independently of Cyclooxygenase Activity", Nature 414, p. 212 (2001).

Yan, R., et al. "Membrane Anchored Aspartyl Protease with Alzheimer's Disease β Secretase Activity", Nature 402, p. 533 (1999).

Yan, Q., et al. "Anti-Inflammatory Drug Therapy Alters β-Amyloid Processing and Deposition in an Animal Model of Alzheimer's Disease", Journal of Neuroscience 23(20), p. 7504 (2003).

Xia, W., et al. "Preseilin 1 Regulates the Processing of β-Amyloid Precursor Protein C-Terminal Fragments and the Generation of Amyloid β-Protein in Endoplasmic Reticulum and Golgi", Biochemistry 3, 16465 (1998).

Braga, et al., "Making crystals from crystals: a green route to crystal engineering and polymorphism", Chem. Comm., Apr. 2005, 3635-3645.

Criton, et al., "Mutant Presenilins of Alzheimer's Disease increase production of 42-Residue Amyloid β-protein in both transfected cells and transgenic mice", Nature Medicine, Jan. 1997, 3(1), 67-72.

Curtis, et al., "1, 6, 13, 8, 25, 30-Hexaoxa [6.6.6.](1, 3, 5) cyclophane. Attempted synthesis of a [4] Cyptand", Journal of the Chemical Society, Perkin Transactions 1: Organic and Bio-Organic Chemistry, 1977, 7, 785-788 (XP-002508187).

Evans, et al., "Synthesis of Diaryl Ethers through the copper-promoted arylation of Phenols with Arylbornic Acids. An expedient synthesis of Thyroxine", Tetrahedron Letters, Jan. 1998, 39, 2937-2940.

Fauran, et al., "Pharmacologically active ethyl 4-amindo-2-(p-chlorophenyl)pyrimidin-6-yl acetate", CAPLUS, 2011, Accession Number: 1973:124623, 4 pages.

Hendrickson, et al., "A new synthesis of Depsidones. Diploicin and Gangaleoidin", Journal of the American Chemical Society, 1972, 94(19), 6834-6843 (XP-002508189).

International Patent Application No. PCT/US2008/079905: International Search Report dated Aug. 1, 2009, 2 pages.

International Patent Application No. PCT/US2008/080241: International Search Report dated Feb. 20, 2009, 2 pages.

Kaminski, et al., "Side-chain retention during lithiation of 4-Picoline and 3,4-Lutidine: Easy access to molecular diversity in Pyridine Series", European J. of Organic Chemistry, Oct. 2003, 19, 3855-3860.

Krivun, et al., "Pyrylium salts from pyrones and some organometallic compounds", Chemistry of Heterocyclic Compounds, Oct. 1973, 9(10), 1191-1194 (XP-002544092).

Krivun, et al., "Pyrylium salts from pyrones and some organometallic compounds", HCAPLUS, 2009, Accession No. 1974:47782, 2 pages. (Abstract).

Lin, et al., "Structure-Activity studies on a novel series of cholinergic channel activators based on a Heteroaryl Ether framework", Bioorganic & Medicinal Chemistry Letters, Aug. 1999, 9, 2747-2752.

Patani, et al., "Bioisosterism: A rational approach in drug design", Chem. Rev., May 1996, 96(8), 3147-3176.

Silverman, Richard B., "The Organic Chemistry of Drug Design and Drug Action", Academic Press, Inc., 1992, Chapter 2: Drug Discovery, Design, and Development, 15-22.

Tagat, et al., "Synthetic inhibitors of Interleukin-6 II: 3,5-Diaryl Pyridines and Meta-Terphenyls", Bioorganic & Medicinal Chemistry Letters, Sep. 1995, 5(18), 2143-2146.

Tanzi, et al., "Twenty years of the Alzheimer's Disease Amyloid Hypothesis: A Genetic Perspective", Cell, Feb. 2005, 120, 545-555.

Vu, et al., "A Practical method for the preparation of 2-Arylbenzofurans and the synthesis of Moracin A and B", Liebigs Ann. Chem., 1984, 734-741 (XP-002508188) (English Abstract).

West, Anthony R., "Solid state chemistry and its applications", Wiley, New York, Mar. 1988, 358 and 365.

Wilson, et al., "Preparation of tephenylcarboxylates for treatment of Alzheimer's disease", CAPLUS, 2010, Accession No. 2007:1201441, 3 pages.

\* cited by examiner

AMINE LINKED MODULATORS OF γ-SECRETASE

CROSS REFERENCE TO RELATED APPLICATIONS

This application claims priority of the benefits of the filing of U.S. Provisional Application Ser. No. 60/981,293, filed Oct. 19, 2007. The complete disclosures of the aforementioned related U.S. patent application is/are hereby incorporated herein by reference for all purposes.

FIELD OF THE INVENTION

The present invention relates the use of compounds having the general Formula I, wherein the definitions or A, X, Y, $R^1$ $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

SUMMARY OF THE INVENTION

A compound having the general Formula (I)

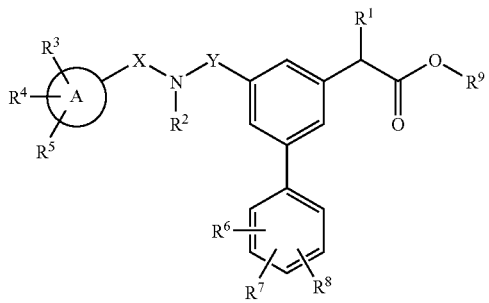

wherein
A is selected from the group consisting of phenyl, heterocyclyl, heteroaryl

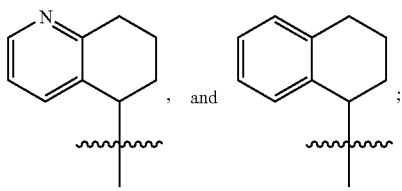

X is $CH_2$, a direct bond, or $CHC_{(1-5)}$alkyl wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$; alkenyl selected from $C_2H_3$, $i$-$C_3H_5$, $n$-$C_3H_5$, $n$-$C_4H_7$, $i$-$C_4H_7$, sec-$C_4H_7$; wherein said alkyl and alkenyl groups are optionally substituted with one, two, or three substituents independently selected from the group consisting of F, Cl, Br, I and $CF_3$;

$R^2$ is selected from the group consisting of H, benzyl, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, $i$-$C_3H_5$, $n$-$C_3H_5$, $n$-$C_4H_7$, $i$-$C_4H_7$, sec-$C_4H_7$; wherein said alkyl and alkenyl groups are optionally substituted with one, two, or three substituents independently selected from the group consisting of F, Cl, Br, I, and $CF_3$; alternatively, when $R^2$ is alkyl, it may be combined with $R^3$, the A ring, X, and the attached nitrogen to form a 9 or 10 membered fused ring system;

$R^3$, and $R^6$, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

$R^4$, $R^5$, $R^7$, and $R^8$ are independently selected from the group consisting of $CF_3$, H, F, Cl, $OCH_3$, $C_{(1-4)}$alkyl, and CN;

$R^9$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$; alkenyl selected from $C_2H_3$, $i$-$C_3H_5$, $n$-$C_3H_5$, $n$-$C_4H_7$, $i$-$C_4H_7$, sec-$C_4H_7$; wherein said alkyl and alkenyl groups are optionally substituted with one, two, or three substituents independently selected from the group consisting of F, Cl, Br, I and $CF_3$;

and solvates, hydrates, esters, and pharmaceutically acceptable salts thereof.

DETAILED DESCRIPTION OF THE INVENTION

A compound having the general Formula (I)

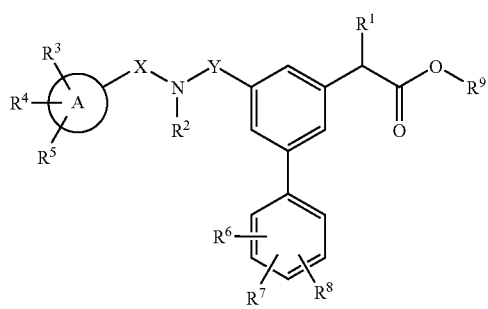

wherein
A is selected from the group consisting of phenyl, heterocyclyl, heteroaryl

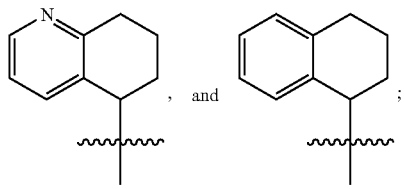

X is $CH_2$, a direct bond, or $CHC_{(1-5)}$alkyl wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$; alkenyl selected from $C_2H_3$, $i$-$C_3H_5$, $n$-$C_3H_5$, $n$-$C_4H_7$, $i$-$C_4H_7$, sec-$C_4H_7$; wherein said alkyl and alkenyl groups are optionally substituted with one, two, or three substituents independently selected from the group consisting of F, Cl, Br, I and $CF_3$;

$R^2$ is selected from the group consisting of H, benzyl, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, $i$-$C_3H_5$, $n$-$C_3H_5$, $n$-$C_4H_7$, $i$-$C_4H_7$, sec-$C_4H_7$; wherein said alkyl and alkenyl groups are optionally substituted with one, two, or three substituents independently selected from the group consisting of F, Cl, Br, I, and $CF_3$; alternatively, when $R^2$ is alkyl, it may be combined with $R^3$, the A ring, X, and the attached nitrogen to form a 9 or 10 membered fused ring system;

$R^3$, and $R^6$, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

$R^4$, $R^5$, $R^7$, and $R^8$ are independently selected from the group consisting of $CF_3$, H, F, Cl, $OCH_3$, $C_{(1-4)}alkyl$, and CN;

$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

and solvates, hydrates, esters, and pharmaceutically acceptable salts thereof.

In another embodiment of the invention

A is selected from the group consisting of phenyl, heterocyclyl, heteroaryl

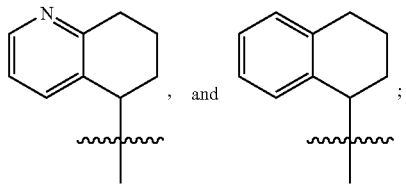

X is $CH_2$, a direct bond, or $CHC_{(1-5)}alkyl$ wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$; and alkenyl selected from $C_2H_3$, i-$C_3H_5$, n-$C_3H_5$, n-$C_4H_7$, i-$C_4H_7$, and sec-$C_4H_7$;

$R^2$ is selected from the group consisting of H, benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, and sec-$C_4H_7$; wherein said alkyl and alkenyl groups are optionally substituted with one, two, or three substituents independently selected from the group consisting of F, Cl, Br, I, and $CF_3$; alternatively, when $R^2$ is alkyl, it may be combined with $R^3$, the A ring, X, and the attached nitrogen to form a 9 or 10 membered fused ring system;

$R^3$, and $R^6$, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

$R^4$, $R^5$, $R^7$, and $R^8$ are independently selected from the group consisting of $CF_3$, H, F, Cl, $OCH_3$, $C_{(1-4)}alkyl$, and CN;

$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$;

and solvates, hydrates, esters, and pharmaceutically acceptable salts thereof.

In another embodiment of the invention

A is selected from the group consisting of phenyl, heterocyclyl, heteroaryl

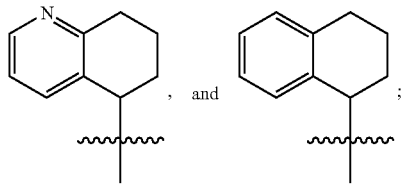

X is $CH_2$, a direct bond, or $CHC_{(1-5)}alkyl$ wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$; and alkenyl selected from $C_2H_3$, i-$C_3H_5$, n-$C_3H_5$, n-$C_4H_7$, i-$C_4H_7$, and sec-$C_4H_7$;

$R^2$ is selected from the group consisting of H, benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, and sec-$C_4H_7$; alternatively, when $R^2$ is alkyl, it may be combined with $R^3$, the A ring, X, and the attached nitrogen to form a 9 or 10 membered fused ring system.

$R^2$ is selected from the group consisting of H, benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, and sec-$C_4H_7$; wherein said alkyl and alkenyl groups are optionally substituted with one, two, or three substituents independently selected from the group consisting of F, Cl, Br, I, and $CF_3$; alternatively, when $R^2$ is alkyl, it may be combined with $R^3$, the A ring, X, and the attached nitrogen to form a 9 or 10 membered fused ring system;

$R^3$, and $R^6$, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

$R^4$, $R^5$, $R^7$, and $R^8$ are independently selected from the group consisting of $CF_3$, H, F, Cl, $OCH_3$, $C_{(1-4)}alkyl$, and CN;

$R^9$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, $sec$-$C_4H_9$, and $tert$-$C_4H_9$;

and solvates, hydrates, esters, and pharmaceutically acceptable salts thereof.

and solvates, hydrates, esters, and pharmaceutically acceptable salts thereof.

In another embodiment of the invention

A is selected from the group consisting of phenyl, heterocyclyl, heteroaryl

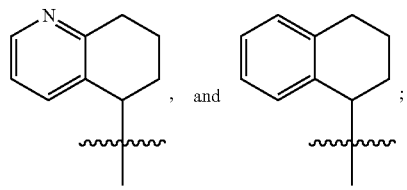

X is $CH_2$, a direct bond, or $CHC_{(1-5)}$alkyl wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, $sec$-$C_4H_9$, and $tert$-$C_4H_9$; and alkenyl selected from $C_2H_3$, $i$-$C_3H_5$, $n$-$C_3H_5$, $n$-$C_4H_7$, $i$-$C_4H_7$, and $sec$-$C_4H_7$;

$R^2$ is selected from the group consisting of H, benzyl, alkyl selected from the group $CH_3$, $C_2H_5$, $i$-$C_3H_7$, $n$-$C_3H_7$, $i$-$C_4H_9$, $n$-$C_4H_9$, $sec$-$C_4H_9$, $tert$-$C_4H_9$, $CH_2CH_2CH(CH_3)_2$, $C(O)CH_2CH(CH_3)_2$; alkenyl selected from $C_2H_3$, $i$-$C_3H_5$, $n$-$C_3H_5$, $n$-$C_4H_7$, $i$-$C_4H_7$, and $sec$-$C_4H_7$; alternatively, when $R^2$ is alkyl, it may be combined with $R^3$, the A ring, X, and the attached nitrogen to form a 9 or 10 membered fused ring system.

$R^3$ and $R^6$ are independently selected from the group consisting of $C(O)NH_2$, $OCF_3$, $CF_3$, H, F, Cl, $OCH_3$, $C_{(1-4)}$alkyl, and CN;

$R^4$, $R^5$, $R^7$, and $R^8$ are independently selected from the group consisting of $CF_3$, H, F, Cl, $OCH_3$, $C_{(1-4)}$alkyl, and CN;

$R^9$ is H;

and solvates, hydrates, esters, and pharmaceutically acceptable salts thereof.

In another embodiment of the invention

A is selected from the group consisting of phenyl, pyridyl,

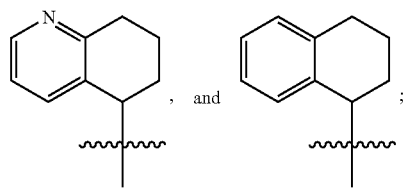

X is $CH_2$, a direct bond, or $CHC_{(1-5)}$alkyl;

Y is $CH_2$ or a direct bond;

$R^1$ is $CH_2CH(CH_3)_2$;

$R^2$ is H, $CH_3$, $CH_2CH_3$, $CH_2CH_2CH(CH_3)_2$, $C(O)CH_2CH(CH_3)_2$; alternatively $R^2$ and $R^3$, together with the A ring, X, and the attached nitrogen may form a fused ring system selected from the group consisting of:

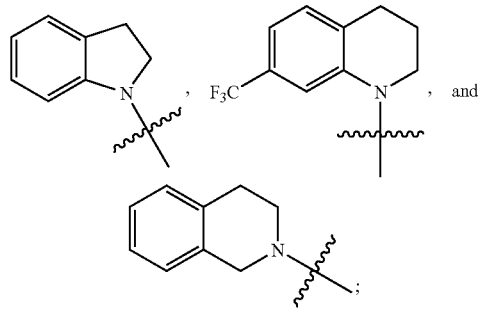

$R^3$, $R^4$, and $R^5$, are H, Cl, $CF_3$, F, —CN, $C(O)NH_2$, $CH(CH_3)_2$, $CH_3$, $C(CH_3)_3$, $OCF_3$;

$R^6$, $R^7$, and R are H, F, Cl, and $CF_3$;

$R^9$ is H;

and solvates, hydrates, esters, and pharmaceutically acceptable salts thereof.

Another embodiment of the invention comprises a compound selected from the group consisting of:

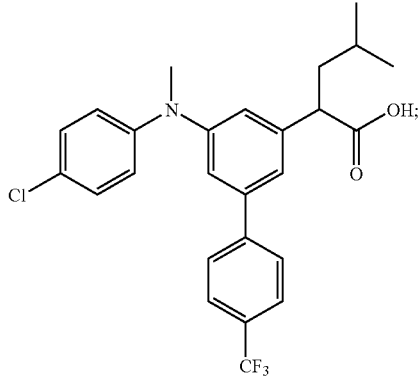

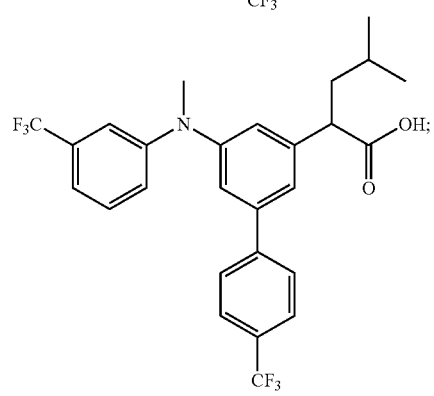

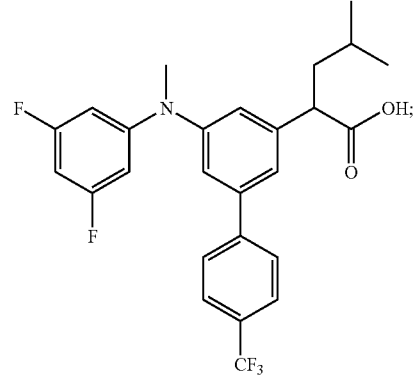

-continued
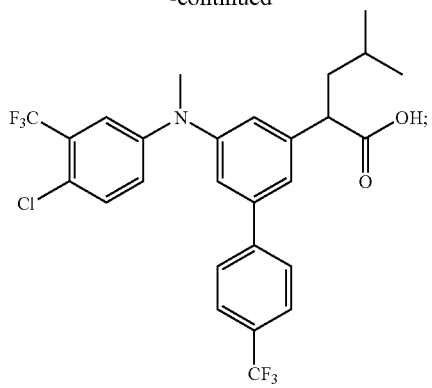
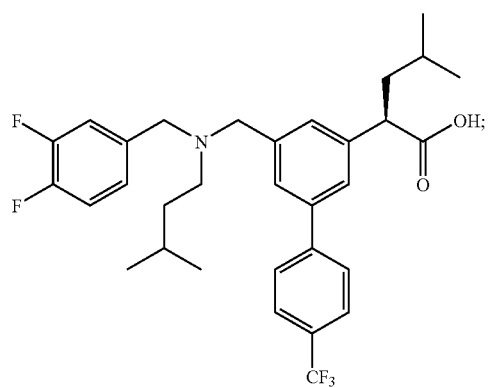
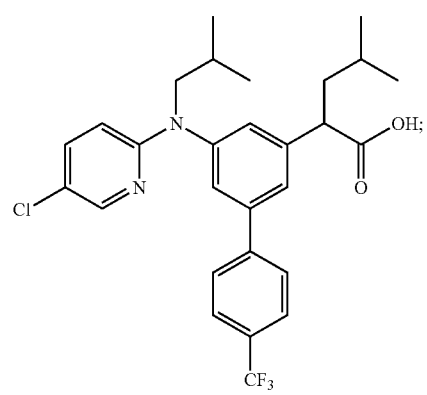
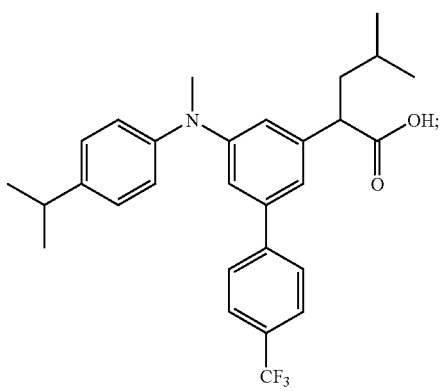
-continued
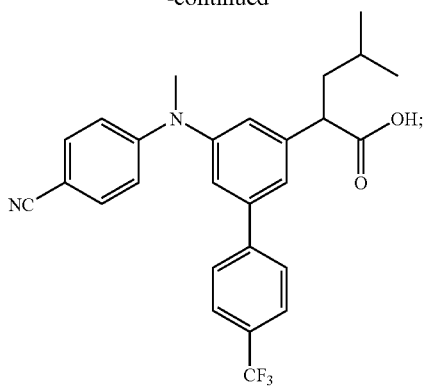
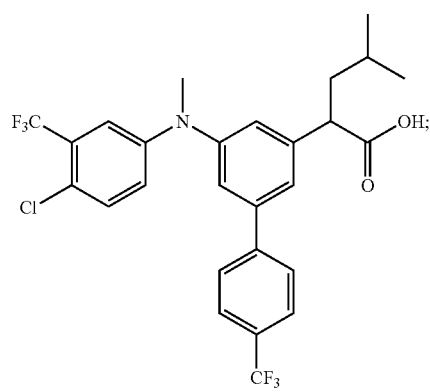
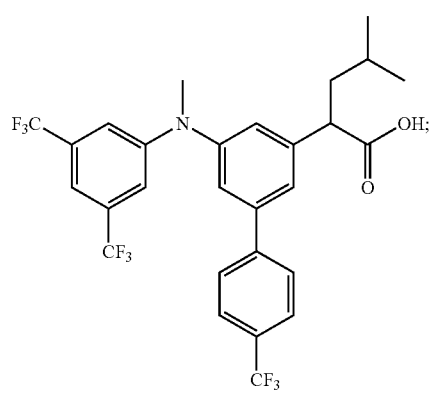
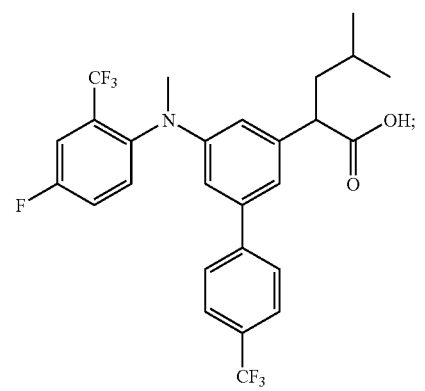

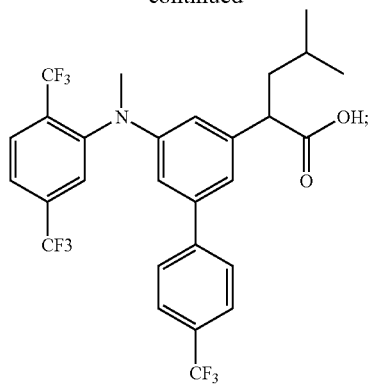
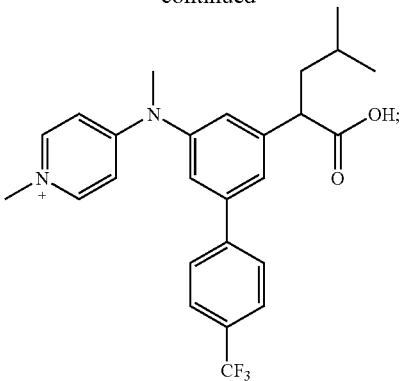
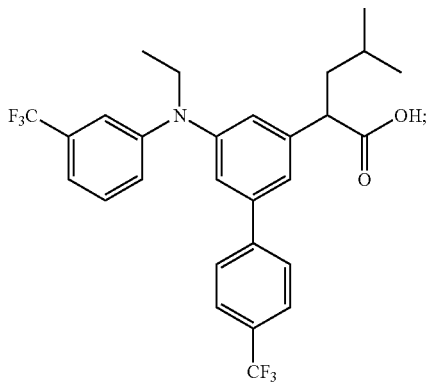
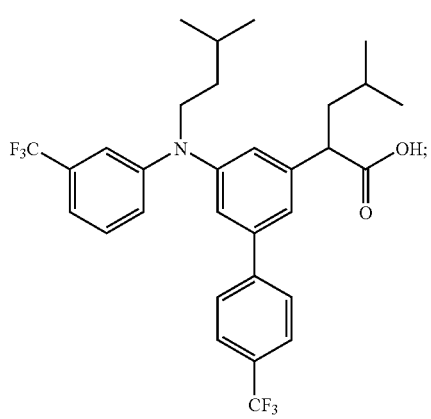
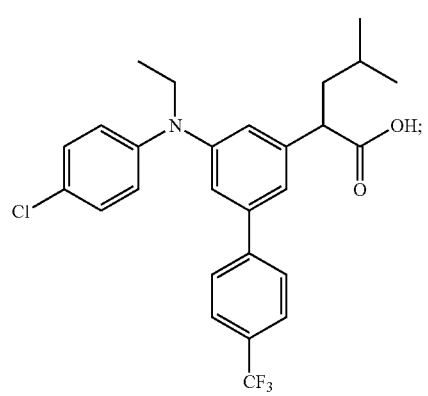
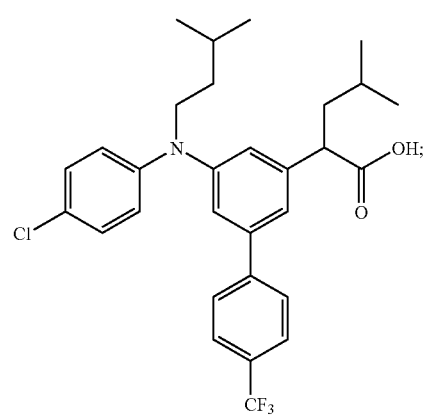
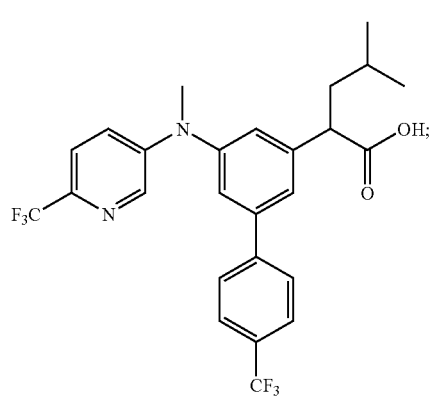
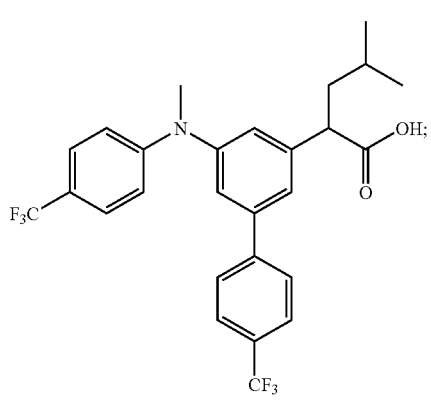

-continued
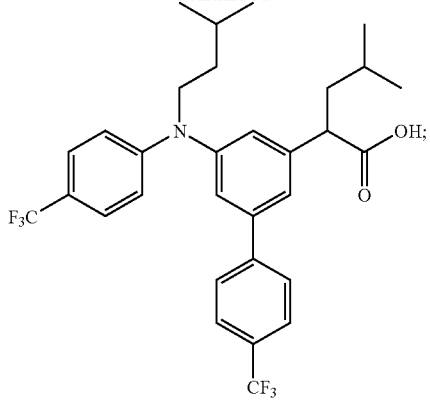
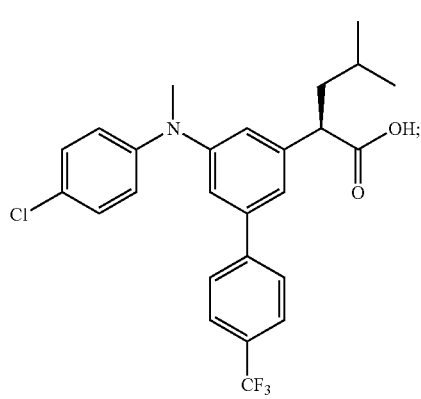
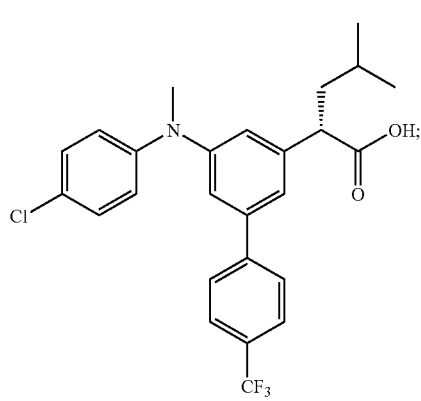
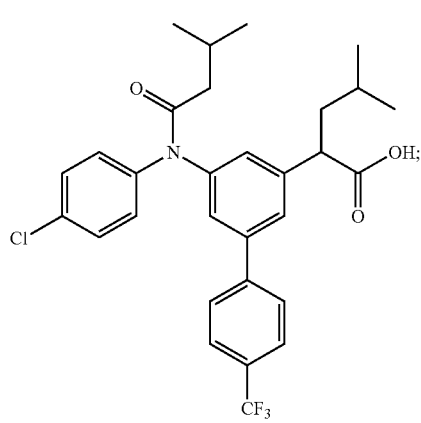
-continued
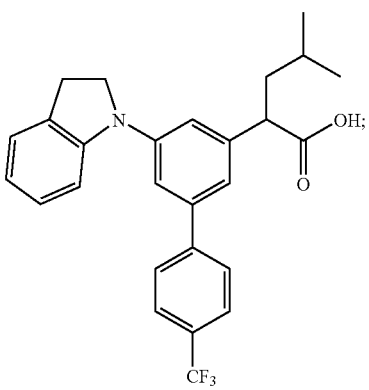
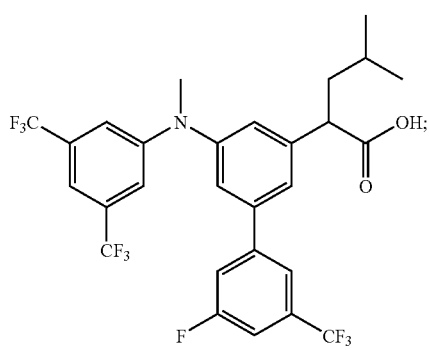
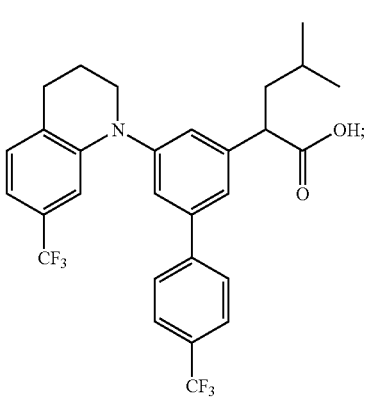
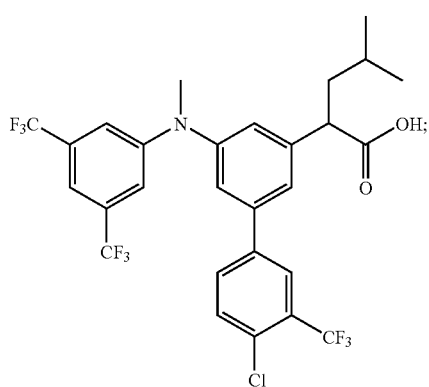

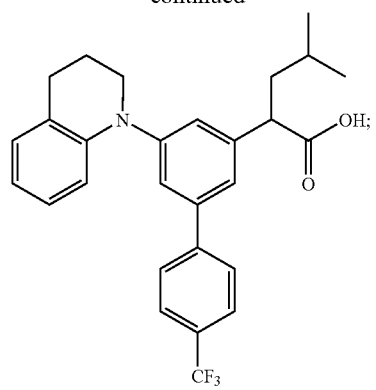
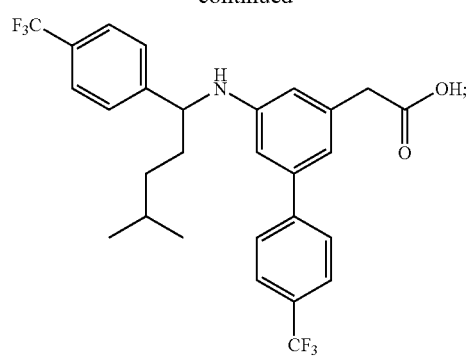
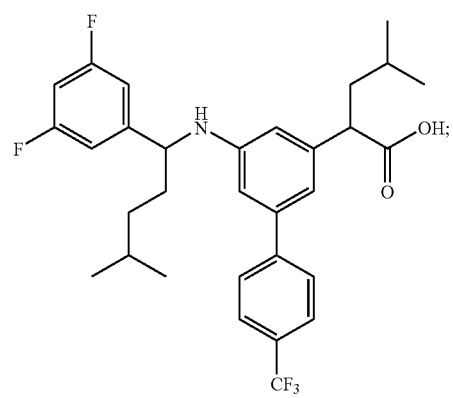
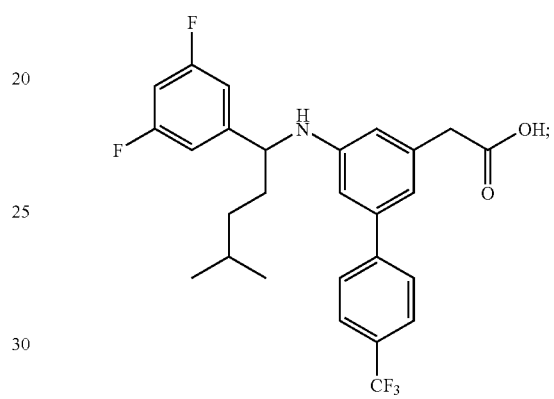
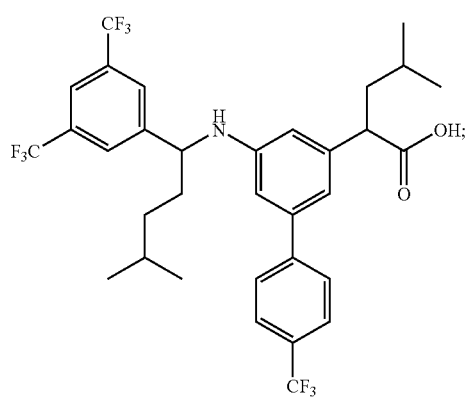
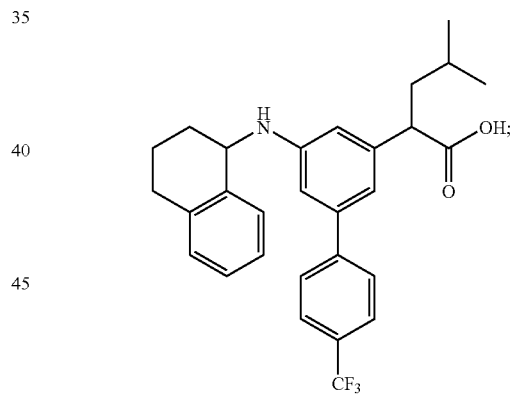
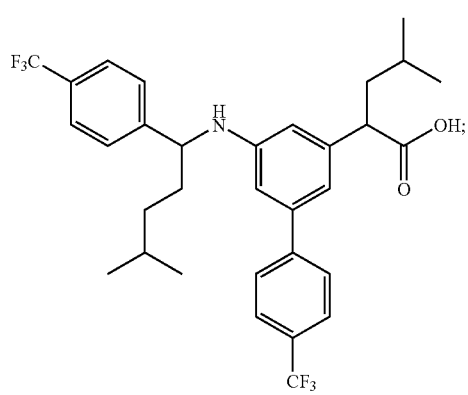
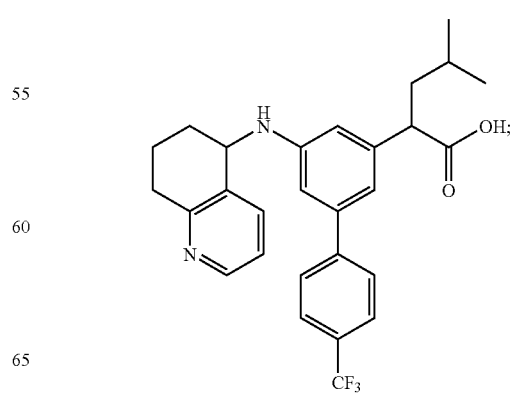

17
-continued
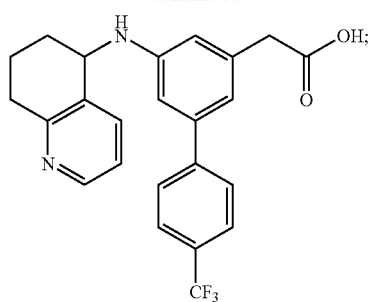
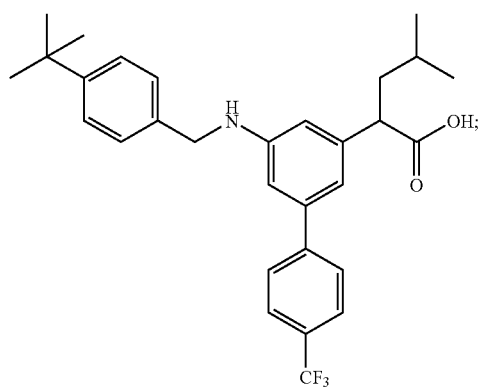
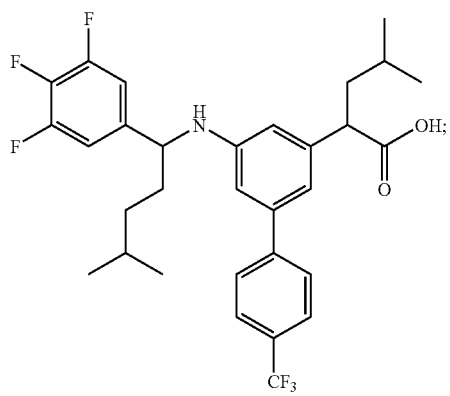
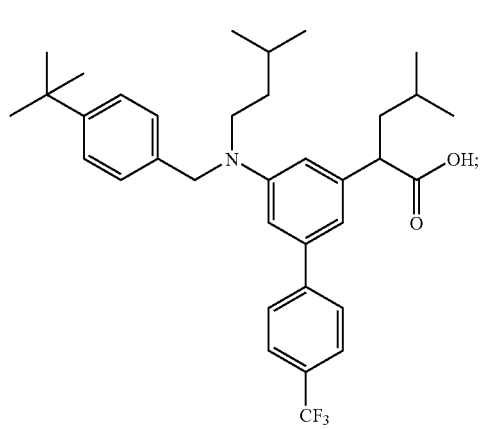
18
-continued
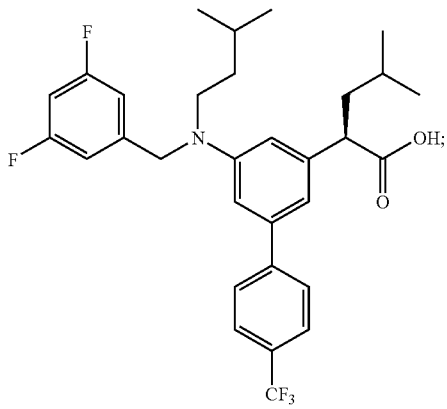
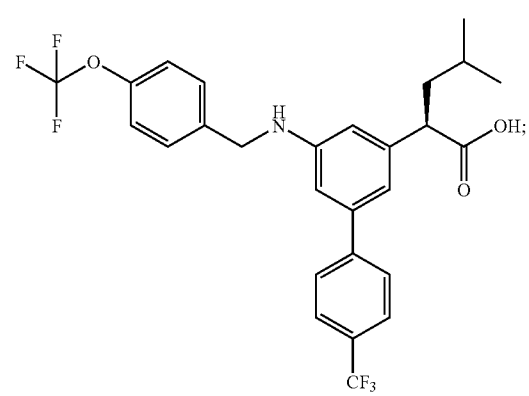
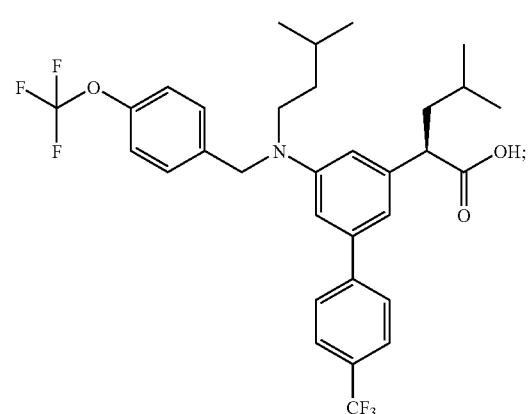
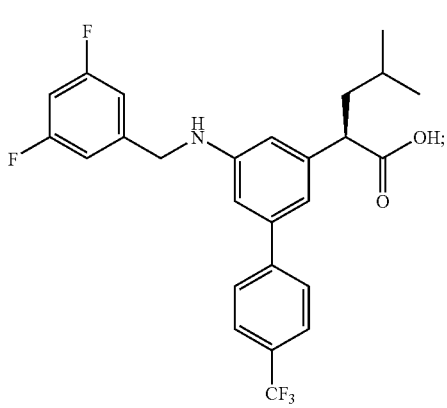

-continued
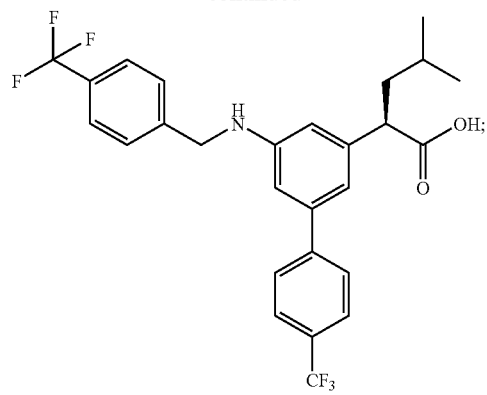
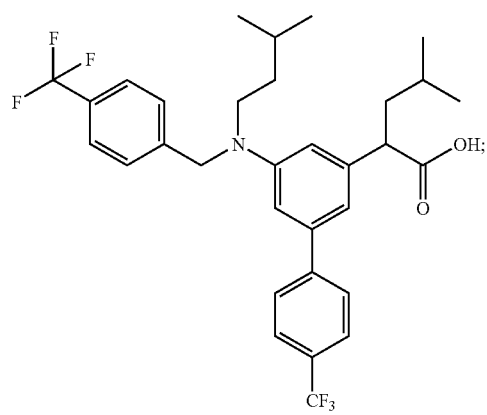
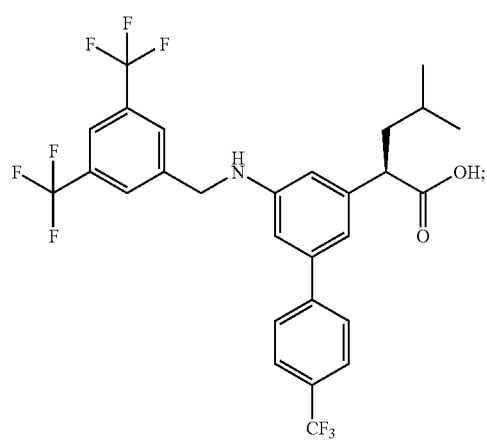
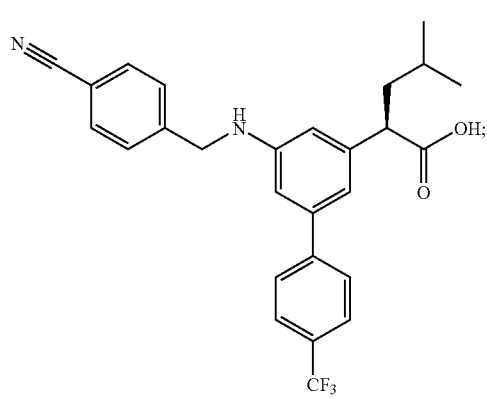
-continued
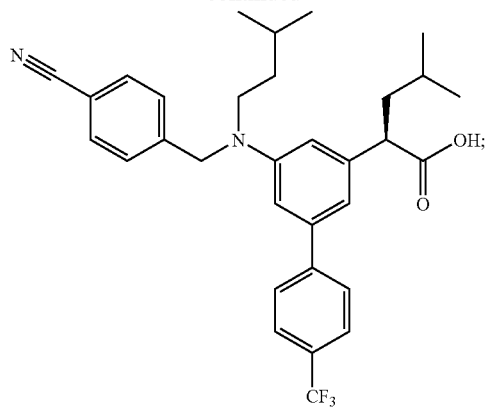
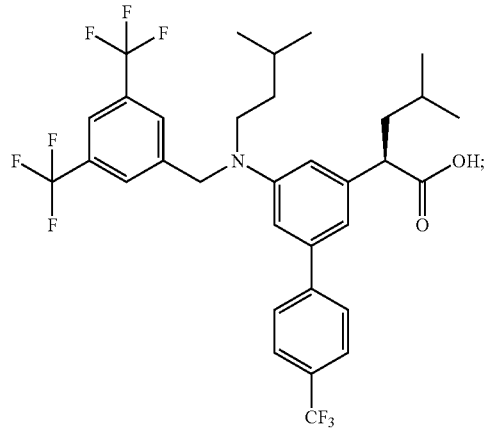
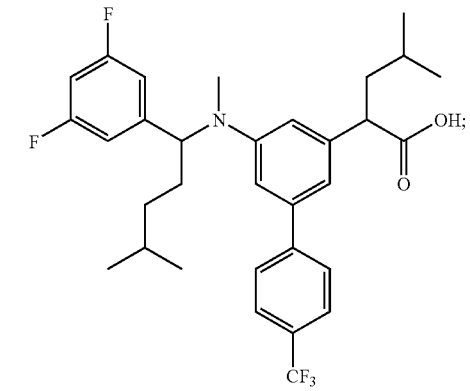
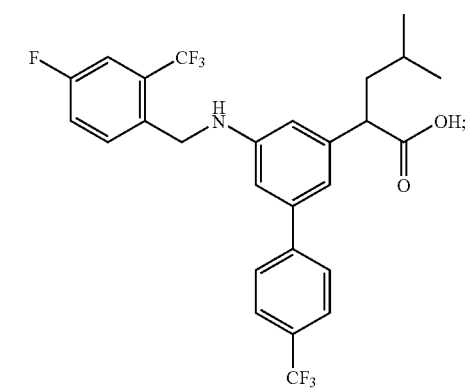

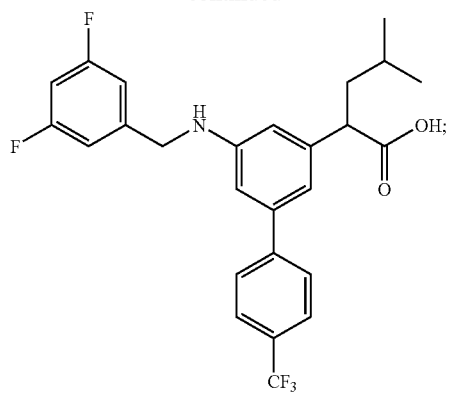
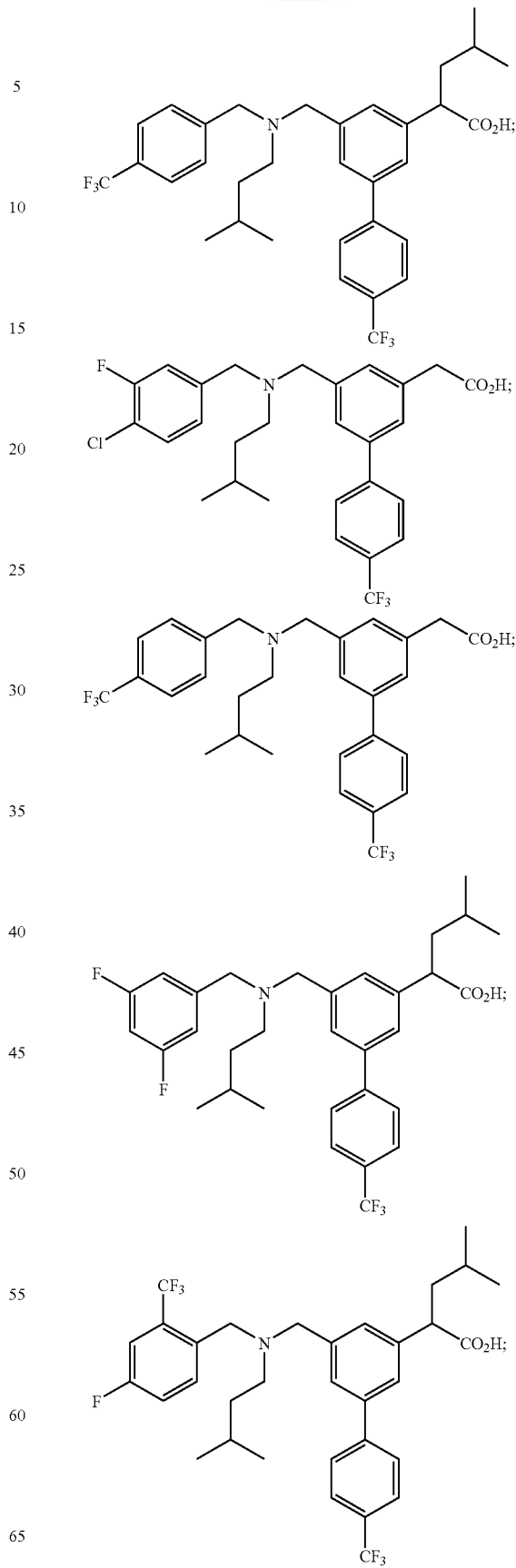

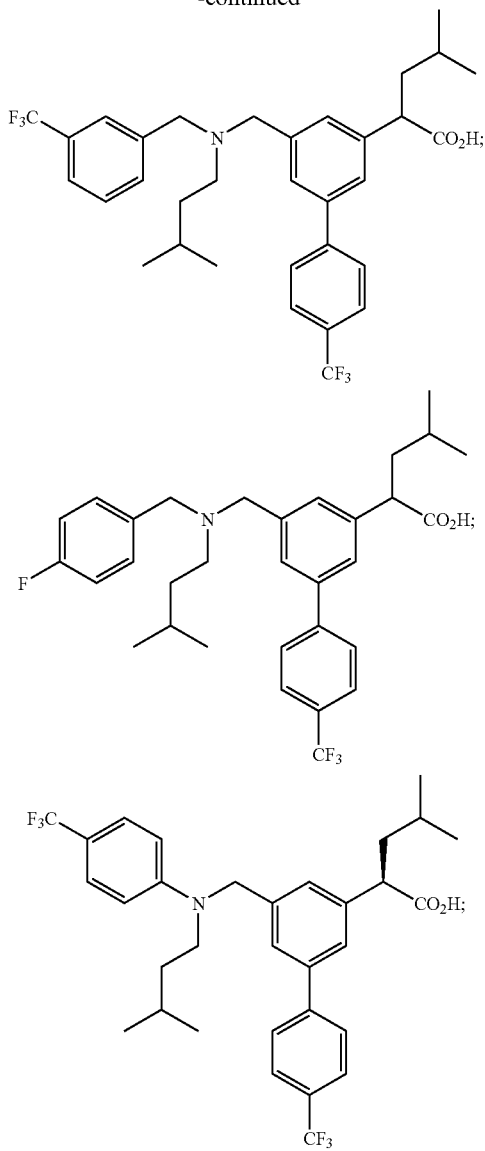

and solvates, hydrates, esters, and pharmaceutically acceptable salts thereof.

In another embodiment, the invention relates to a compound as described in the above examples or Formula I for use as a medicament.

In another embodiment, the invention relates to the use of a compound according to the above examples or Formula I for the preparation of a medicament for the modulation of γ-secretase.

In another embodiment, the invention relates to the use of a compound according to the above examples or Formula I for the preparation of a medicament for the treatment of a disease associated with an elevated level of Aβ42-production.

In another embodiment, the invention relates to the use of a compound according to the above examples or Formula I for the preparation of a medicament for the treatment of Alzheimer's disease.

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

The term "pharmaceutically acceptable" means approved by a regulatory agency such as the EMEA (Europe) and/or the FDA (US) and/or any other national regulatory agency for use in animals, preferably in humans.

The respective salts of the compounds according to the invention can be obtained by customary methods which are known to the person skilled in the art, for example by contacting these with an organic or inorganic base in a solvent or dispersant, or by cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according of the invention in any suitable manner, such as any suitable in vitro assay.

The invention is considered to include prodrugs, i.e., derivatives of an acting drug that possess superior delivery capabilities and therapeutic value as compared to the acting drug. Prodrugs are transformed into active drugs by in vivo enzymatic or chemical processes.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The invention also relates to compounds of the invention for use as medicaments. The compounds are as defined above, furthermore with respect to the medicaments the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta peptide species produced, most importantly levels of Abeta-42 (see Example section, infra).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129).

With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 µM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Aβ peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The activity of the γ-secretase can be modulated in different ways, i.e. resulting in different profiles of the various Aβ-peptides.

Respective dosages, routes of administration, formulations etc are disclosed further below.

The invention further relates to the use of the compounds of Formula I for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound of Formula I in a mixture with an inert carrier.

Modulators of γ-secretase derived from compounds of Formula I can be formulated into pharmaceutical compositions comprising a compound of Formula I in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds according to the invention and their pharmaceutically acceptable salts, optionally in combination with other pharmaceutically active compounds are suitable to treat or prevent Alzheimer's disease or the symptoms thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by modulation of γ-secretase activity, which comprises administering to the subject a therapeutically effective dose of the instant pharmaceutical composition.

As used herein, the term "subject" includes, without limitation, any animal or artificially modified animal having a disorder ameliorated by modulation of γ-secretase activity. In a preferred embodiment, the subject is a human.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

Various delivery systems are known and can be used to administer a compound of the invention for the treatment of Alzheimer's disease or for the modulation of the γ-secretase activity, e.g. encapsulation in liposomes, microparticles, and microcapsules: If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

Modulators of γ-secretase derived from compounds of Formula I can be delivered in a vesicle, in particular a liposome (Langer (1990) Science 249, 1527.

Modulators of γ-secretase derived from compounds of Formula I can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. patent U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645.

Substantial data from several studies are available to the skilled person in the art, which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

DEFINITIONS

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, n-butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

General Synthesis Description

The following general description is for illustrative purposes only and is in no way meant to limit the invention.

Compounds of Formula I wherein A, X, Y, $R^1$, $R^2$, $R^3$, $R^4$, $R^5$, $R^6$, $R^7$, and $R^8$ are defined as in Formula I, and $R^9$ is H, may be obtained by hydrolysis of esters II under standard acidic or basic hydrolysis conditions, including reaction with NaOH, at room temperature, for several hours, in an appropriate solvent mixture, such as water, tetrahydrofuran (THF), and methanol or ethanol. For illustrative purposes, esters II are shown with $R^9$ as alkyl, but those skilled in the art will recognize that hydrolysis will work for all $R^9$ as defined in Formula I.

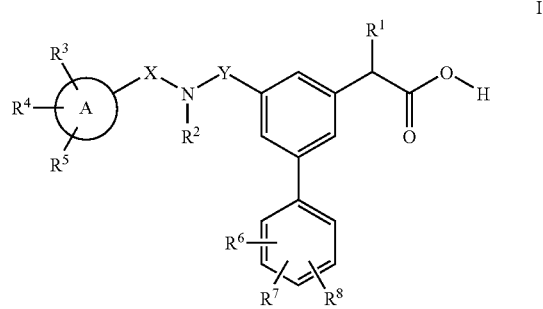

I

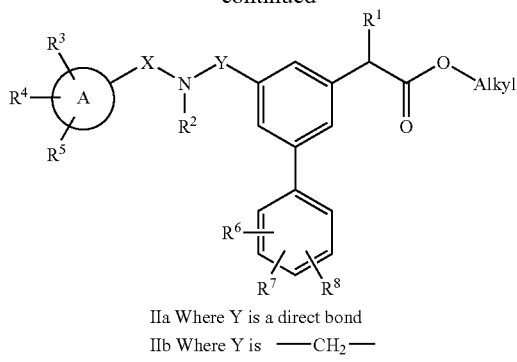

IIa Where Y is a direct bond
IIb Where Y is ——CH₂—

Compounds of Formula IIa, where Y is a direct bond may be obtained by coupling compounds IIIa or IIIb with aryl amines, heteroarylamines, arylmethyleneamines or heteroarylmethyleneamines under typical Buckwald or Hartwig conditions, e.g. in toluene, dioxane or THF in the presence of potassium t-butoxide and a catalyst, e.g. palladium (II) acetate (Pd(OAc)₂) or palladium (0) trans, trans-dibenzylideneacetone at elevated temperature (range from 80-180 degrees C.) or the reaction may be preformed in a microwave reactor. The products are subsequently alkylated with alkyl halides or mesylates in the presence of base such as cesium carbonate or potassium carbonate or reductivly alkylated with alkyl carboxyadehydes to provide compounds IIa.

Compounds IIIa may be obtained from the reaction of phenols IV with trifluoromethanesulfonic anhydride in DCM in the presence of a base such as pyridine, or triethylamine at 0° C. Intermediates IIIb can be obtained from reactions of phenols IV with concentrated HCl, or HBr, or HI at elevated temperature (ranges from 25 to 120° C.). Alternatively, compounds IIIb can be obtained under mild conditions by treatment of the corresponding triflates IIIa with pinacolborane in dioxane in the presence of triethylamine catalyzed with PdCl₂ to give pinacol boronate esters which are then treated with copper (II) halide in the methanol-water, procedure described by Nesmejanow et al. (Chem Ber. 1960, 2729). The aforementioned pinacolboronate esters could also be reacted with NaI in aqueous THF in the presence of chloramines-T to give aryl iodides described by J. W. Huffman et. al. (Synthesis, 2005, 547).

Compounds of Formula IIIc can be obtained from compounds IIIa or IIIb by reaction with benzophenone imine in an aprotic solvent such as DMF, toluene or THF in the presence of a catalytic amount of tetrakistriphenylphosphine palladium (0) and triphenylphosphine and followed by aqueous basic hydrolysis of the imine intermediates. Alternatively, compounds IIa can be obtained from compounds IIIc by reductive amination with aryl carboxyaldehydes, aryl ketones, heteroarylcarboxyaldehydes, or heteroarylketones with sodium borohydride or sodium triacetoxyborohydride. The secondary amine products can be subsequently alkylated with alkyl halides or reductively aminated with alkylaldehydes for installing R² group on the amine functionality to compounds IIa.

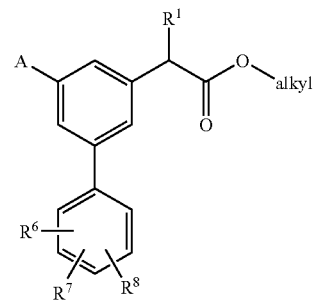

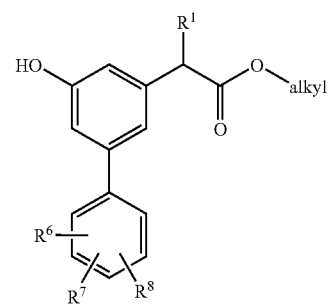

wherein:
IIIa, A = OTf
IIIb, A = Br, Cl, I
IIIc, A = NH₂

Compounds IV may be prepared by debenzylation of compounds V by hydrogenation in alcohol, e.g. MeOH or EtOH in the presence of Pd—C. Debenzylation can also be achieved with other methods, such as BBr₃ in DCM, NaCN in DMSO/ 120-200° C. or LiCl in DMF/120-200° C.

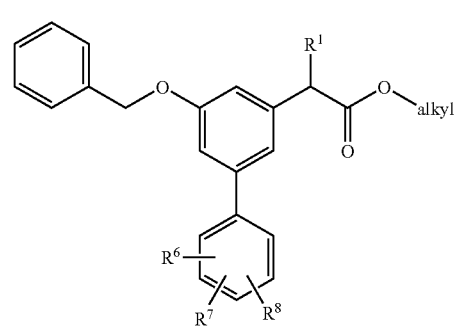

Compounds V may be prepared from alkylation of compounds VI with either alkyl or alkenyl halides. Treatment of compounds VI in THF or other aprotic solvent with a base, e.g. lithium bis(trimethylsilyl)amide, sodium bis(trimethylsilyl)amide, or lithium diisopropylamide at −78° C., followed by the addition of an electrophile, e.g. an alkyl or alkenyl halides, yields alkylated compounds V.

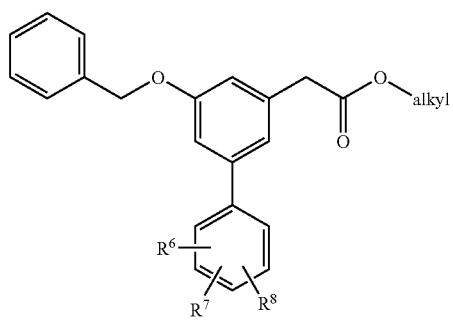

VI

Alternatively, compounds VI may be prepared from compounds VII through a coupling reaction with arylboronic acid under Suzuki conditions of aqueous sodium carbonate in DME in the presence of Pd(PPh$_3$)$_4$. Alternatively, the triflates can be converted to boronate esters under the conditions described above and then can be coupled with aryl bromides or aryl chlorides to give compounds VI.

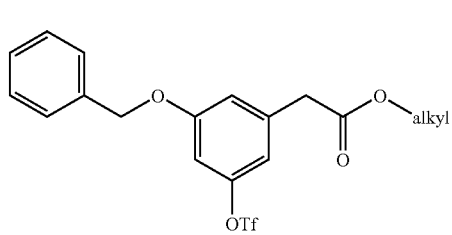

VII

Intermediate triflate compounds VII may be prepared from compounds VIII with trifluoromethanesulfonic anhydride in DCM in the presence of one equivalent of pyridine at 0° C.

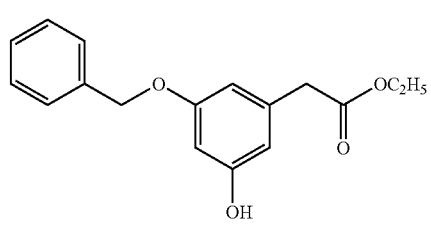

VIII

Intermediate compound VIII can be prepared from mono-debenzylation of compound IX. Selective mono-debenzylation of compound IX can be achieved by selective hydrogenolysis of compound IX in ethanol or methanol with an addition of 1.1 equivalents of base, e.g. sodium hydroxide or potassium hydroxide in the presence of Pd—C catalyst in a Parr shaker. The reaction is allowed to proceed until one equivalent of hydrogen is consumed.

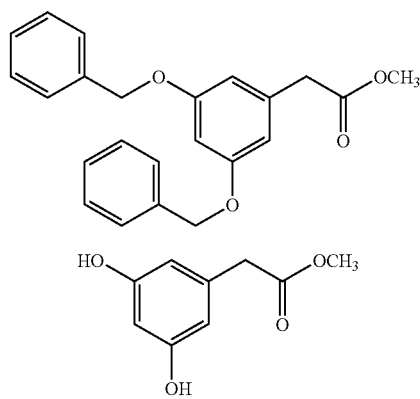

IX

X

Intermediate IX can be easily prepared from reaction of 3,5-dihydroxyphenyl acetic acid methyl ester, compound X, (commercially available) with benzyl bromide and potassium carbonate in DMF at room temperature.

Compounds of Formula IIb, where Y is CH$_2$, can be obtained from reductive amination of compounds XI with aryl carboxyaldehydes, aryl ketones, heteroarylcarboxyaldehydes, or heteroarylketones with sodium borohydride or sodium triacetoxyborohydride. The reductive amination products from aldehydes can be subsequently alkylated with alkyl halides or reductive amination with alkylaldehydes for installing R$^2$ group on the amine functionality to compounds IIb. Compounds XI can be obtained from reduction of compounds XII by hydrogenation using PtO$_2$ in acidic alcohol solvent, e.g. methanol or ethanol. Compounds XII can be obtained from reaction of compounds IIIa or IIIb with zinc cyanide in elevated temperature (80-150 degrees C.) in an aprotic solvent such as DMF in the presence of a catalytic amount of tetrakistriphenylphosphine palladium (0).

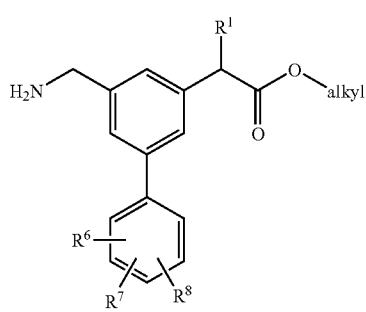

XI

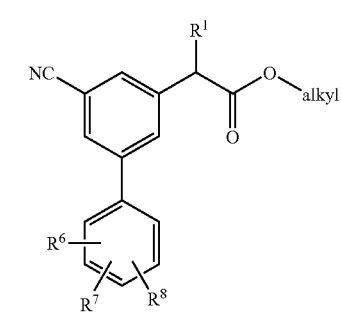

XII

Compounds of Formula I have a chiral center α to the carboxylic group, and can exist as one of two enantiomers (or a mixture thereof, wherein an enantiomeric excess may or may not be present). The enantiomers Ia (R enantiomer) and Ib (S enantiomer) are shown. The pure enantiomers Ia and Ib may be obtained by chiral separation using chiral columns. The enantiomers Ia and Ib may also be separated by resolutions through forming chiral amine salts by fractional recrystallizations. The enantiomers Ia and Ib also may be obtained from kinetic resolution of the racemate of corresponding esters using lipase enzymes, e.g. Amano lipase Ak, Amano lipase PS, Amano lipaseA, Amano lipase M, Amano lipase F-15 Amano lipase G (from Biocatalytics Inc) in aqueous organic solvents, e.g. aqueous DMF, DMSO, t-butyl-ethyl ether or triton X-100 aqueous solutions.

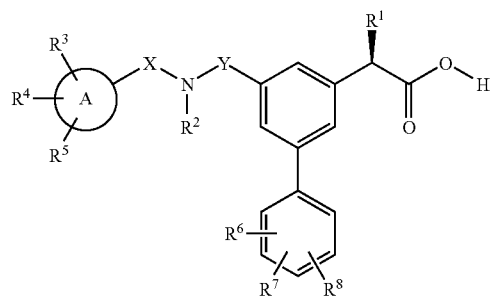

Ia

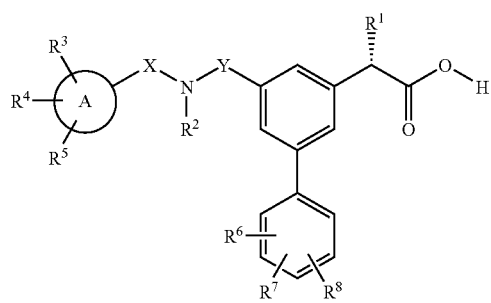

Ib

Alternatively, compounds of Formulae Ia and Ib may be prepared from chiral syntheses. Compounds of Formula Ia or Ib may be obtained from chiral phenolic compounds IVa and IVb as described above.

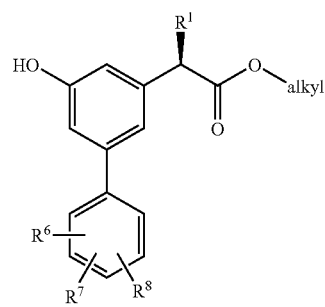

IVa

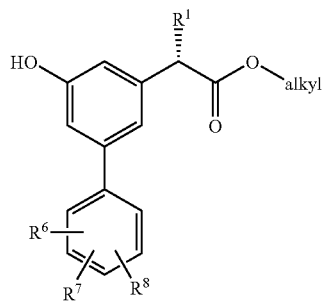

IVb

Chiral compounds IVa and IVb may be obtained from the removal of the chiral auxiliary groups from compounds XIIIa and XIIIb respectively, with lithium hydroxide/hydrogen peroxide in aqueous THF, followed by esterification.

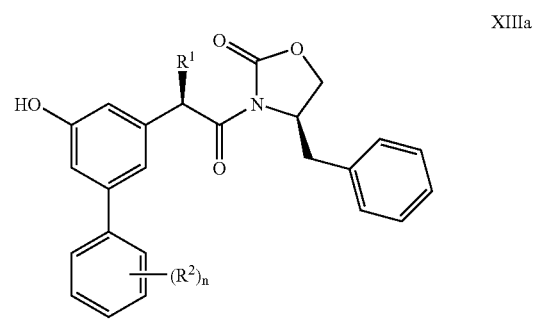

XIIIa

XIIIb

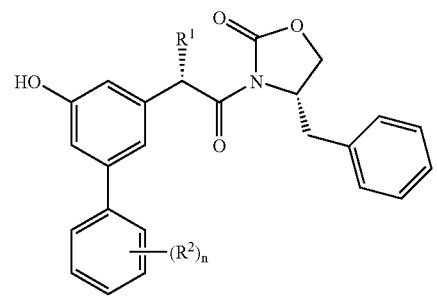

Compounds XIIIa and XIIIb may be prepared from debenzylation of compounds XIVa and XIVb respectively by hydrogenation in an alcohol solvent, e.g. MeOH or EtOH, in the presence of Pd—C.

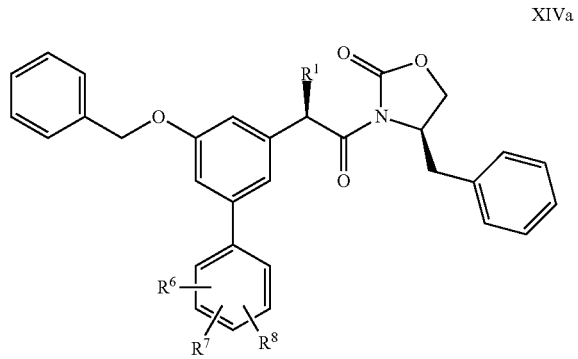

XIVa

XIVb

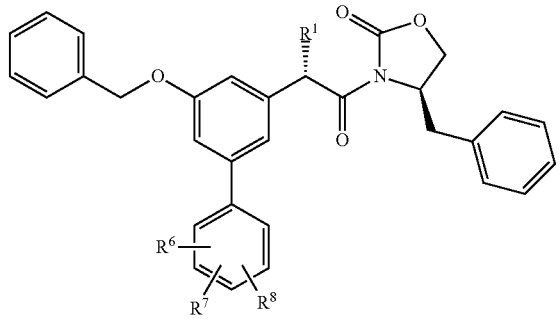

Compounds XIVa and XIVb may be prepared from the alkylation of compounds XVa and XVb respectively with an appropriate alkyl bromide, including sec-butyl bromide or sec-butenyl bromide. Treatment of compounds XVa and XVb in THF or other aprotic solvents with bases, e.g. lithium bis(trimethylsilyl)amide, sodium bis(trimethylsilyl)amide, or lithium diisopropylamide at −78° C., followed by the addition of electrophiles, sec-butyl bromide or sec-butenyl bromide will give alkylated compounds XIVa and XIVb respectively.

XVa

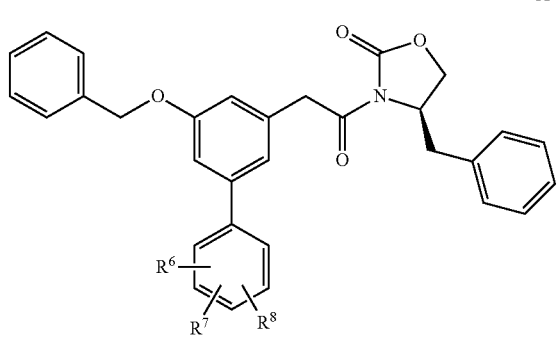

XVb

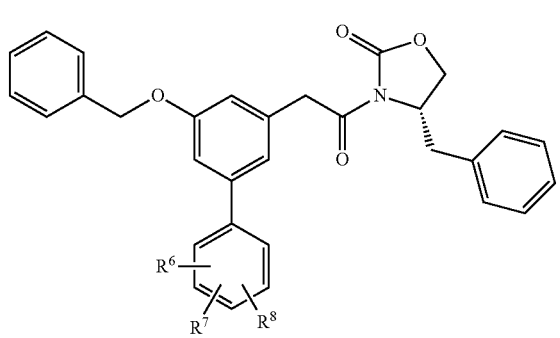

Compounds XVa and XVb may be prepared by coupling intermediates XVI with either the R-isomer of 4-benzyl-oxazolidin-one (XVIIa) or the S-isomer of 4-benzyl-oxazolidin-one (XVIIb) by Evans's procedures. Intermediates XVI may be reacted with pivaloyl chloride, oxalyl chloride or isopropyl chloroformate in THF in the presence of a base, e.g. triethylamine or N-methylmorpholine, to generate the mixed anhydrides or acid chlorides which then are reacted with the lithium salt of XVIIa or XVIIb in THF.

Alternatively, other chiral auxiliary groups may also be used for the chiral syntheses of compounds IVa and IVb, e.g. pseudoephedrine via the A. G. Myers conditions (J. Am. Chem. Soc. 1994, 116, 9361-9362). For examples, treatments of either the carboxylic acid chlorides or anhydride with (+) or (−) pseudoephedrine will give compounds XVIIIa and XVIIIb. The amides are then treated with a strong base, e.g. lithium diisopropyl amide in the presence of lithium chloride, followed by the addition of an alkylating agent to yield the corresponding alkylated products XIXa and XIXb.

XVI

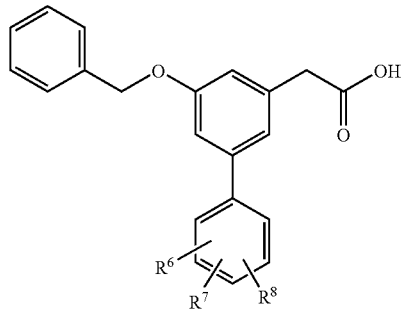

XVIIa

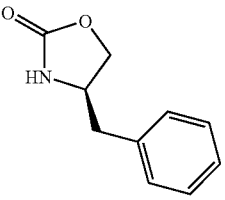

XVIIb

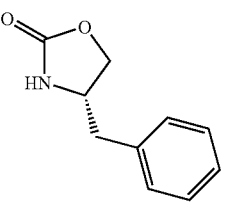

XVIIIa

XVIIIb

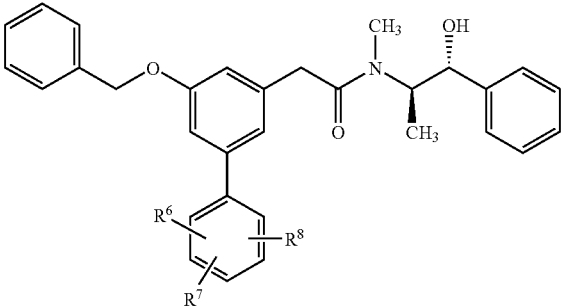

-continued

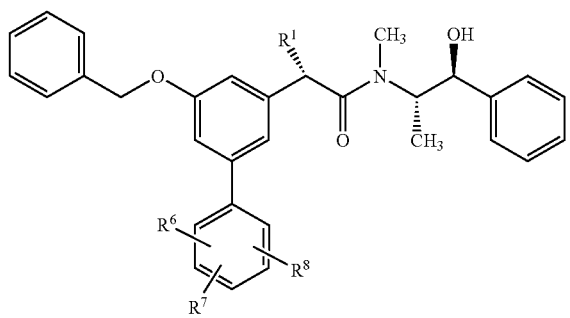
XIXa

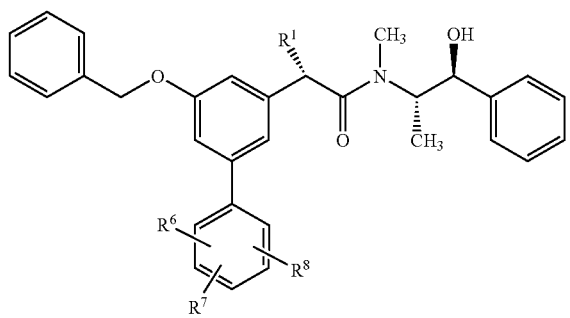
XIXb

Chiral phenolic compounds IVa and IVb can also be prepared from compounds XIXa and XIXb by removal of the chiral auxiliary pseudoephedrine in sulfuric acid aqueous solution and followed by treatment of BBr$_3$/DCM to remove the benzyl protecting group.

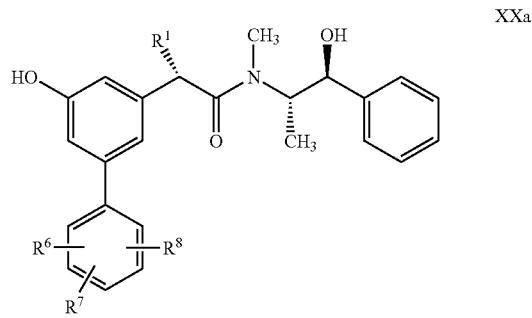
XXa

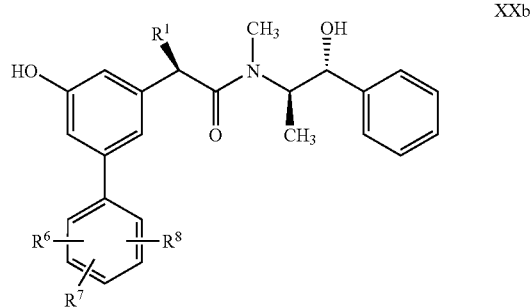
XXb

Additionally, the chiral phenolic compounds XIIIa, XIIIb, XXa and XXb can serve as chiral intermediates for preparing chiral compounds of Formula Ia and Ib. The chiral auxiliary groups are removed at the final stage of synthesis under the conditions described above.

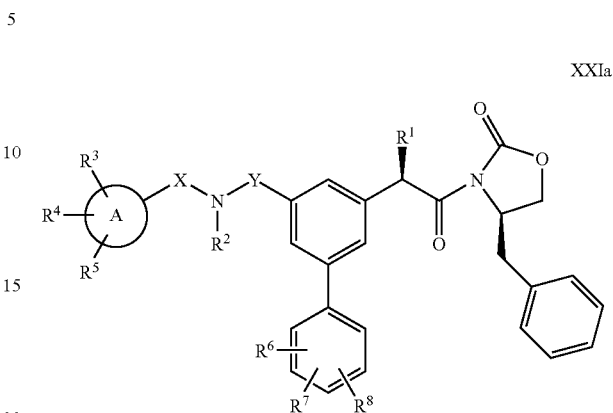
XXIa

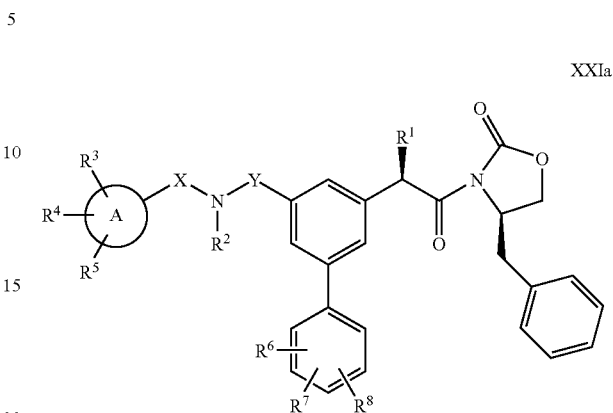
XXIb

Compounds XXIa and XXIb can be prepared from chiral phenolic compounds XIIIa and XIIIb under the similar aforementioned conditions. For example, the triflate compounds XXIIa and XXIIb, prepared from phenolic compounds XIIIa and XIIIb by reacting with trifluoromethylsulfonyl anhydride in pyridine-methylene chloride solution, can give the coupling compounds XXIa and XXIb under Buckwald or Hartwig conditions as described above.

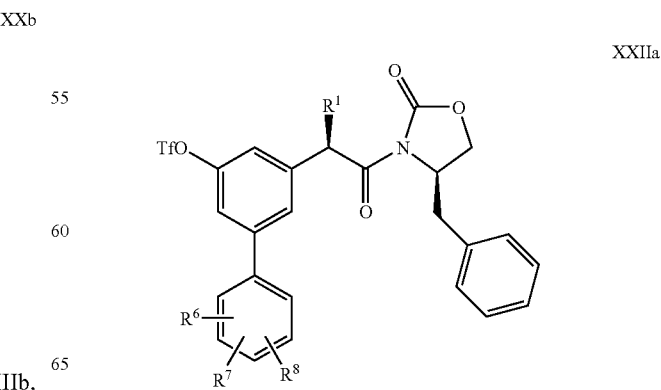
XXIIa

XXIIb

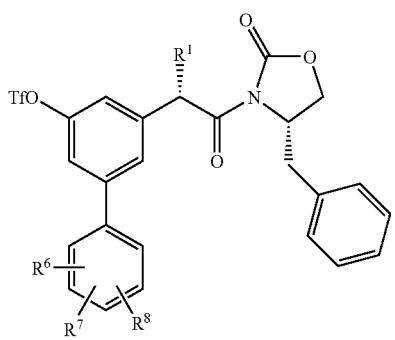

Under similar conditions, compounds XXIIIa and XXIIIb may be prepared from compounds XXIIa and XXIIb by reacting with benzophenone imine in the presence of triphenylphosphine and a catalytic amount of tetrakistriphenylphosphine palladium (0) as mentioned previously. Reductive amination of compounds XXIIIa and XXIIIb with aryl carboxyaldehydes or heteroarylcarboxyaldehydes and followed by alkylation of the nitrogen via reductive amination or alkyl halide alkylations and then removal of the chiral auxiliary groups with lithium hydroxide and hydrogen peroxide in aqueous THF to give chiral compounds Ia and Ib.

XXIIIa

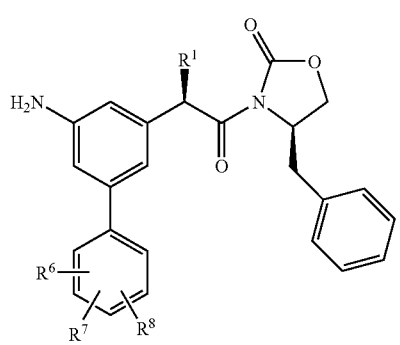

XXIIIb

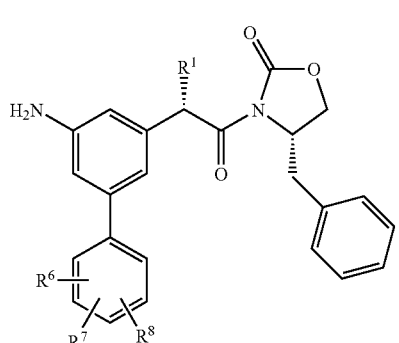

In addition, Compounds XXIVa and XXIVb can be prepared XXIIa and XXIIb as described previously using zinc cyanide and tetrakistriphenylphosphine palladium and then followed by reduction the cyano compounds with platinum oxide in acid alcohol medium. The chiral amine compounds XXIVa and XXIVb can be used to prepare the final target compounds of Formula Ia and Ib in analogous routes to those described previously.

XXIVa

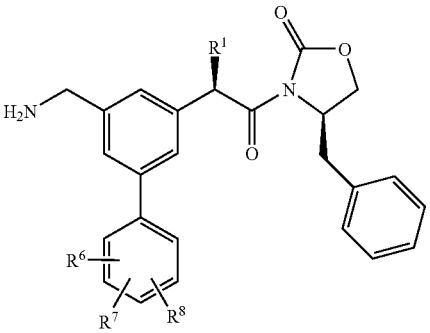

XXIVb

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
| --- | --- | --- |
| A | 1 ml/min | 0-1.5-95% MeCN<br>1.5-6 min 95%<br>4.5-5 min 95%-5% MeCN |

ABBREVIATIONS

| | |
| --- | --- |
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| Eq | Equivalents |
| Et | Ethyl |
| EtOAc | ethyl acetate |
| g | Gram |
| h | Hour |
| HPLC | high pressure liquid chromatography |
| $K_2CO_3$ | Potassium carbonate |
| l | Litre |
| LCMS | liquid chromatography - mass spectrometry |

| | |
|---|---|
| LDA | lithium diisopropylamide |
| M | Molar |
| m | Multiplet |
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

EXAMPLE 1

2-{5-[(4-Chloro-phenyl)-methyl-amino]-4'-trifluoromethyl-biphenyl-3-yl}-4-methyl-pentanoic acid

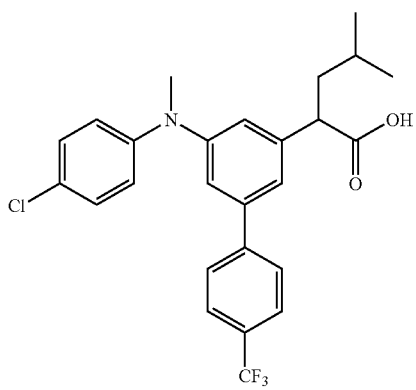

a) (3,5-Bis-benzyloxy-phenyl)-acetic acid methyl ester

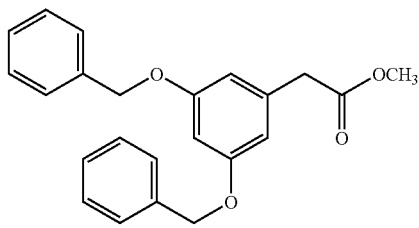

A mixture of (3,5-dihydroxy-phenyl)-acetic acid methyl ester (from Aldrich, 70 g, 0.385 mol), benzylbromide (137 mL, 1.16 mol), potassium carbonate (160 g, 1.16 mol) and DMF (1.5 L) under N$_2$ was mechanically stirred at room temperature overnight. The resulting reaction mixture was poured into a mixture of 1.5 L of ice-water with stirring. The precipitate was obtained by filtration and washed with heptane successively to remove benzyl bromide to give the title compounds (123.7 g) as a brown solid which was air dried for the next reaction. $^1$H-NMR (CDCl$_3$): δ 3.60 (s, 2H), 3.71 (s, 3H), 5.05 (s, 4H), 6.60 (s, 3H), 7.35-7.50 (m, 10H); Calcd for C23H22O4 (M+H) 363.15. Found 363.

b) 3-Benzyloxy-5-hydroxy-phenyl)-acetic acid ethyl ester

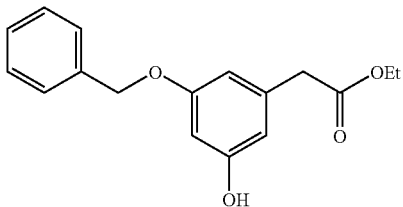

A solution of 3,5-Bis-benzyloxy-phenyl)-acetic acid methyl ester (50 g, 1.38 mol) and NaOH (6.6 g, 1.65 mole) in 1 L of EtOH in the presence of 10% of Pd—C was hydrogenated in a Parr shaker until one equivalent of hydrogen was consumed. The mixture was acidified with concentrated HCl and then the catalyst and solvent were removed to give an oil residue. The crude product was purified by ISCO silica gel column chromatography (ISCO) using EtOAC-heptane as eluents (gradient from 10% to 75% of EtOAc) to give 25 g of (65% yield) the title compound $^1$H-NMR (CDCl$_3$): δ 1.15-1.20 (t, 3H), 3.4-(s, 2H), 4.05-4.1 (q, 2H), 4.9 (s, 2H), 5.5 (s, 1H), 6.4 (s, 2H), 6.5 (s, 1H), 7.207.35 (m, 5H); Calcd for C17H18O4 (M+H) 287.3. Found 287.

c) (3-Benzyloxy-5-trifluoromethanesulfonyloxyphenyl)-acetic acid ethyl ester

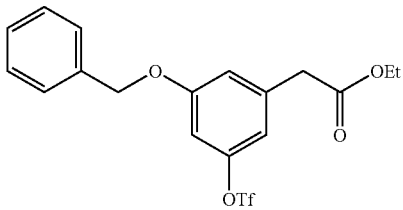

To a solution of 3-(benzyloxy-5-hydroxy-phenyl)-acetic acid ethyl ester (74.4 g, 0.26 mol) in dichloromethane (700 mL) was added pyridine (62.5 mL, 0.78 mol). The mixture was cooled to 0° C. To this cold solution was added trifluoromethanesulfonic anhydride (65.6 mL, 0.39 mol), over 1.5 h, maintaining the internal temperature below 5° C. and stirred for an additional 0.5 h at 0° C. This reaction mixture was poured to a mixture of 1 N HCl (420 mL), and wet-ice (105 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid (108 g) which was carried on to the next step without further purification. Calcd for C18H17F3O6S (M+H) 419.07. Found 419.1.

d) (5-Benzyloxy-4'-trifluoromethyl-biphenyl-3-yl)-acetic acid ethyl ester

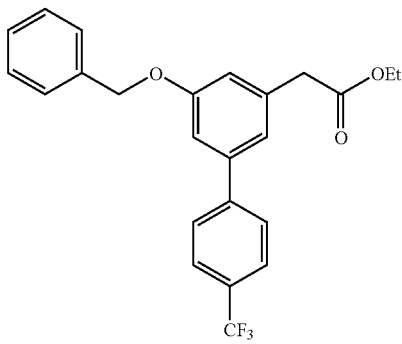

A mixture of (3-benzyloxy-5-trifluoromethanesulfonyloxy-phenyl)-acetic acid ethyl ester (108 g, 0.26 mol), 4-(trifluoromethyl)phenylboronic acid (55.6 g, 0.29 mol), 1,2-dimethoxyethane (1.1 L) and aqueous Na₂CO₃ (2 M, 129 mL, 0.26 mol) was mechanically stirred while purging N₂ at room temperature for 10 min. To this system was added Pd(Ph₃)₄ (480 mg, 0.42 mmol) and heated to reflux (95° C.) for 2.5 h. The red-brown mixture was diluted with EtOAc (0.5 L) and washed with saturated aqueous NaHCO₃ solution (3×200 mL) and brine (2×200 mL). The organic fraction was dried (Na₂SO₄) and concentrated in vacuo. The crude mixture was purified by ISCO column chromatography to obtain (5-benzyloxy-4'-trifluoromethyl-biphenyl-3-yl)-acetic acid ethyl ester (107 g, 100%).

¹H-NMR (CDCl₃): δ 1.26 (t, 3H), 3.66 (s, 2H), 4.17 (q, 2H), 5.12 (s, 2H), 6.99 (s, 1H), 7.12 (s, 2H), 7.34-7.49 (m, 5H), 7.67 (s, 4H); Calcd for C24H21F3O3 (M+H) 415.14. Found 415.2.

e) 2-(5-Benzyloxy-4'-trifluoromethyl-biphenyl-3-yl)-4-methyl-pent-4-enoic acid ethyl ester

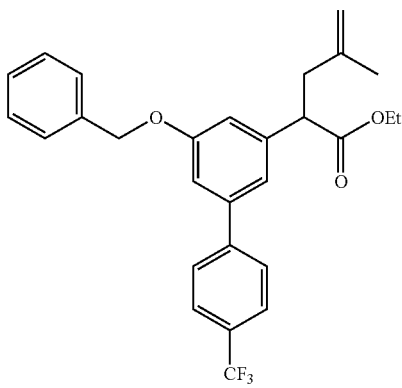

To a solution of compound 1d (4.9 g, 11.8 mmol) in THF (50 mL) at −78° C. was added Li[N(SiMe₃)₂] (1N in THF, 14.2 mL, 14.2 mmol) dropwise. The reaction mixture was stirred for 1 h at −78° C. and then 3-bromo-2-methyl-propene (1.25 mL, 12.4 mmol) was added dropwise. The solution was slowly warmed up to −35° C. and stirred at −35° C. for 0.5 h. The reaction was quenched with NH₄Cl saturated solution and extracted with EtOAc. The organic extracts was dried (Na₂SO₄), concentrated and purified by column chromatography give compound 1e (5.1 g, 92%) as a clear oil; ¹H NMR (400 MHz, CHLOROFORM-D) δ ppm 1.19-1.29 (m, 3H), 1.74 (s, 3H), 2.47 (m, 1H), 2.85 (m, 1 H), 3.83 (m, 1H), 4.11 (m, 2H), 4.72 (s, 1H), 4.77 (s, 1H), 5.12 (s, 2H), 7.03 (s, 1H), 7.10 (s, 1H), 7.15 (s, 1H), 7.35-7.48 (m, 5H), 7.67 (s, 4H); Calcd for C28H27F3O3 (M+H) 469.19. Found 469.

f) 2-(5-Hydroxy-4'-trifluoromethyl-biphenyl-3-yl)-4-methyl-pentanoic acid ethyl ester

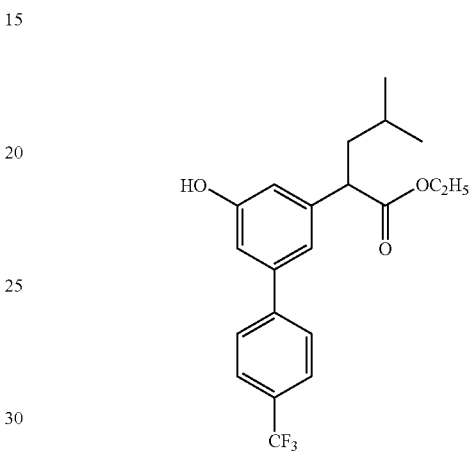

A mixture of compound 1e (5.1 g, 10.9 mmol), 10% Pd/C (500 mg) in EtOH (50 mL) was hydrogenated under H₂ (40 psi) in par-shaker for 20 h. The resulting reaction mixture was filtered through a celite pad and the filtrate was concentrated to give the title compound (4.2 g, 100%) as a clear oil; 1H NMR (300 MHz, CHLOROFORM-D) δ ppm 0.92 (d, J=6.6 Hz, 6H), 1.25 (m, 3H), 1.49-1.61 (m, 1H), 1.65-1.70 (m, 1H), 1.95-2.05 (m, 1H), 3.67 (t, J=7.7 Hz, 1H), 4.10-4.29 (m, 2H), 6.91 (s, 1H), 6.97 (t, J=2.0 Hz, 1H), 7.08 (s, 1H), 7.65 (s, 4H); Calcd for C21H23F3O3 (M+H) 381.16. Found 381.

g) 4-Methyl-2-(5-trifluoromethanesulfonyloxy-4'-trifluoromethyl-biphenyl-3-yl)-pentanoic acid ethyl ester

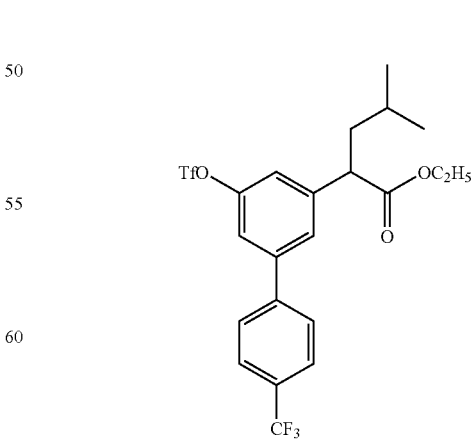

To a solution of compound 1f, 2-(5-Hydroxy-4'-trifluoromethyl-biphenyl-3-yl)-4-methyl-pentanoic acid ethyl ester, 2.8 g, 7.36 mmol) and N-phenyl-bis-(trifluoromethanesulfonimide) (3.16 g, 8.83 mmol) in THF (30 mL) under $N_2$ was added $Et_3N$ (2.05 mL, 14.7 mmol). The reaction mixture was heated to reflux overnight. After cooling to room temperature, the solution was concentrated and purified by column chromatography to give the title compound (3.7 g, 98%) as a colorless thick oil; $^1H$ NMR (400 MHz, CHLOROFORM-D) δ ppm 0.94 (dd, J=6.60, 1.47 Hz, 6H), 1.22-1.28 (m, 3H), 1.46-1.52 (m, 1H), 1.69 (ddd, J=13.82, 7.09, 6.97 Hz, 1H), 1.98-2.06 (m, 1 H), 3.75 (t, J=7.83 Hz, 1H), 4.10-4.21 (m, 2H), 7.31 (s, 1H), 7.38 (s, 1 H), 7.57 (s, 1 H), 7.65-7.75 (m, 4H); Calcd for C22H22F6O5S (M+H) 513.11. Found 513.

h) 2-{5-[(4-Chloro-phenyl)-methyl-amino]-4'-trifluoromethyl-biphenyl-3-yl}-4-methyl-pentanoic acid A mixture of compound 1g (50 mg, 0.098 mmol), N-methyl-4-chloro-aniline (23 mg, 0.156 mmol), Pd(OAc)$_2$ (6.6 mg, 0.029 mmol), racemic-2-(di-t-butylphosphino)-1,1'-binaphthyl (35 mg, 0.088 mmol) and NaOt-Bu (11.3 mg, 0.12 mmol) in toluene (1.5 mL) was heated to 150° C. under microwave irradiation (300 w, 250 psi) for 20 min. After cooling to room temperature, the solution was partitioned between EtOAc and H$_2$O. The organic layer was dried (Na$_2$SO$_4$), concentrated and purified by column chromatography to give an aniline intermediate.

A mixture of the above intermediate and NaOH (2N in H$_2$O, 0.114 mL, 0.228 mmol) in THF-MeOH (0.6 mL-0.6 mL) was stirred for 18 h. The reaction mixture was concentrated on a rotary evaporator and the residue was dissolved in CH$_2$Cl$_2$ and water and the mixture was acidified with 1N HCl. The organic phase was separated and the aqueous phase was extracted with CH$_2$Cl$_2$. The combined organic layers were dried, concentrated, and purified by column chromatography to give 12 mg (26%, 2 steps) of the title compound as a white solid; 1H NMR (400 MHz, CHLOROFORM-D) δ ppm 0.88-0.98 (m, 6H), 1.50-1.61 (m, 1H), 1.71 (ddd, J=13.82, 7.09, 6.97 Hz, 1H), 1.97 (ddd, J=13.57, 7.70, 7.58 Hz, 1H), 2.04 (s, 1H), 3.32-3.42 (s, 3H), 3.67 (t, J=7.83 Hz, 1H), 6.98-7.08 (m, 3H), 7.12 (s, 1H), 7.21-7.31 (m, 3H), 7.59-7.69 (m, 4H); Calcd for C26H25ClF3NO2 (M+H) 476.15. Found 476.1.

EXAMPLE 2

4-Methyl-2-{5-[methyl-(3-trifluoromethyl-phenyl)-amino]-4'-trifluoromethyl-biphenyl-3-yl}-pentanoic acid

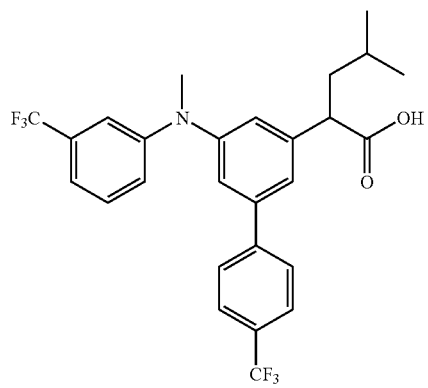

a) 4-Methyl-2-[4'-trifluoromethyl-5-(3-trifluoromethyl-phenylamino)-biphenyl 3-yl]-pentanoic acid ethyl ester

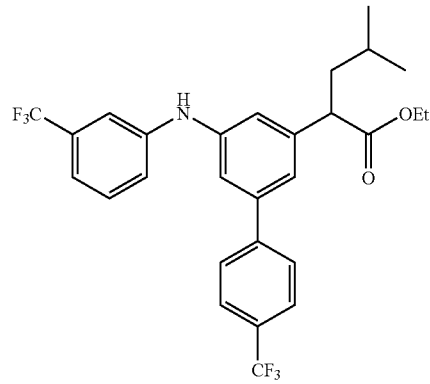

A mixture of compound 1g (50 mg, 0.098 mmol), 4-trifluoromethyl-aniline (27 mg, 0.167 mmol), Pd(OAc)$_2$ (6.6 mg, 0.029 mmol), racemic-2-(di-t-butylphosphino)-1,1'-binaphthyl (35 mg, 0.088 mmol) and NaOt-Bu (11.3 mg, 0.12 mmol) in toluene (1.5 mL) was heated to 150° C. under microwave irradiation (300 w, 250 psi) for 20 min. After cooling to room temperature, the solution was partitioned between EtOAc and H$_2$O. The organic layer was dried (Na$_2$SO$_4$), concentrated and purified by column chromatography to give compound 2a as a white solid.

b) 4-Methyl-2-{5-[methyl-(3-trifluoromethyl-phenyl)-amino]-4'-trifluoromethyl-biphenyl-3-yl}-pentanoic acid To a solution of compound 2a (41 mg, 0.078 mmol) in acetonitrile (1 mL) was added MeI (0.049 mL, 0.78 mmol) and Cs$_2$CO$_3$ (74 mg, 0.228 mmol). The mixture was heated to 85° C. for 17 h. After cooling to room temperature, the solution was partitioned in EtOAc and H$_2$O. The organic layer was dried (Na$_2$SO$_4$), concentrated and purified by column chromatography to give an ester intermediate.

A mixture of the above intermediate and NaOH solution (2N in H$_2$O, 0.114 mL, 0.228 mmol) in THF-MeOH (0.6 mL-0.6 mL) was stirred for 18 h and concentrated. CH$_2$Cl$_2$ and water were added, and the mixture was acidified with 1N HCl. The organic phase was separated and the aqueous phase was extracted with CH$_2$Cl$_2$. The combined organic layers were dried, concentrated, and purified by column chromatography to give 21 mg (53%, 3 steps) of the title compound as a white solid; 1H NMR (400 MHz, MeOD) δ ppm 0.82 (d, J=6.60 Hz, 6H), 1.41 (dt, J=13.45, 6.72 Hz, 1H), 1.53-1.62 (m, 1H), 1.79-1.90 (m, 1H), 3.29 (s, 3H), 3.61 (t, J=7.70 Hz, 1H), 7.01-7.10 (m, 4H), 7.20-7.31 (m, 3H), 7.59-7.67 (m, 4H); Calcd for C27H25F6NO2 (M+H) 510.18. Found 510.1.

EXAMPLE 3

2-{5-[(3,5-Difluoro-phenyl)-methyl-amino]-4'-trifluoromethyl-biphenyl-3-yl}-4-methyl-pentanoic acid

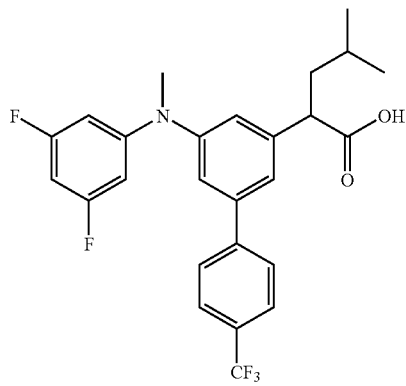

Replacing 3-trifluoromethyl-aniline with 3,5-difluoro-aniline following the same procedure as in Example 2 gave the title compound 3; 1H NMR (400 MHz, MeOD) δ ppm 0.83 (d, J=6.60 Hz, 6H), 1.35-1.46 (m, 1H), 1.55-1.64 (m, 1H), 1.80-1.90 (m, 1H), 3.23 (s, 3H), 3.64 (t, J=7.83 Hz, 1H), 6.14-6.20 (m, 1H), 6.25 (dd, J=10.52, 1.96 Hz, 2H), 7.13 (s, 1H), 7.28 (t, J=1.83 Hz, 1H), 7.35 (s, 1H), 7.60-7.69 (m, 4H); Calcd for C26H24F5NO2 (M+H) 478.17. Found 478.2.

EXAMPLE 4

2-{5-[(4-Chloro-3-trifluoromethyl-phenyl)-methyl-amino]-4'-trifluoromethyl-biphenyl-3-yl}-2,4-dimethyl-pentanoic acid

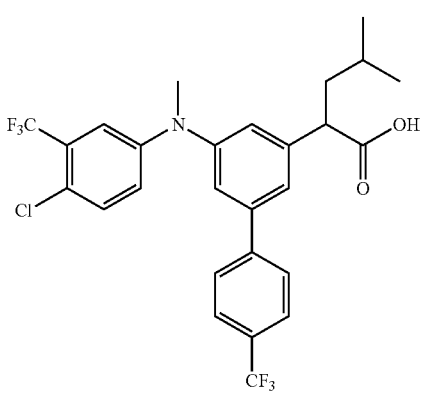

A mixture of compound 1g (60 mg, 0.117 mmol), 4-chloro-3-trifluoromethyl-aniline (28 mg, 0.143 mmol), Pd(OAc)$_2$ (6.6 mg, 0.029 mmol), racemic-2-(di-t-butylphosphino)-1,1'-binaphthyl (35 mg, 0.088 mmol) and NaOt-Bu (14.6 mg, 0.14 mmol) in toluene (1.5 mL) was heated to 150° C. under microwave irradiation (300 w, 250 psi) for 20 min. After cooling to room temperature, the solution was partitioned in EtOAc and H$_2$O. The organic layer was dried (Na$_2$SO$_4$), concentrated and purified by column chromatography to give an intermediate.

To a solution of the above intermediate (30 mg, 0.053 mmol) and parafomaldehyde (20 mg) in CH$_2$Cl$_2$-TFA (0.3 mL-0.3 mL) was added NaBH$_4$ (20 mg, 0.53 mmol). The reaction mixture was stirred at room temperature for 15 h and concentrated. The residue was purified by preparative TLC to give an ester intermediate.

The above intermediate was hydrolyzed following the same the procedure as in Example 1 to give the title compound 4; 1H NMR (400 MHz, MeOD) δ ppm 0.78-0.88 (m, 6H), 1.42-1.53 (m, 1H), 1.80-1.91 (m, 1H), 2.15 (s, 3H), 3.22 (s, 3H), 3.90-3.97 (m, 1H), 6.86 (d, J=2.45 Hz, 1H), 6.93 (dd, J=8.93, 2.81 Hz, 1H), 7.04-7.15 (m, 2 H), 7.23-7.33 (m, 1H), 7.39 (d, J=8.07 Hz, 2H), 7.60-7.70 (m, 3H); Calcd for C28H26ClF6NO2 (M+H) 558.16. Found 558.2.

EXAMPLE 5

2-(5-{[(3,4-Difluoro-benzyl)-(3-methyl-butyl)-amino]-methyl}-4'-trifluoromethyl-biphenyl-3-yl)-4-methyl-pentanoic acid

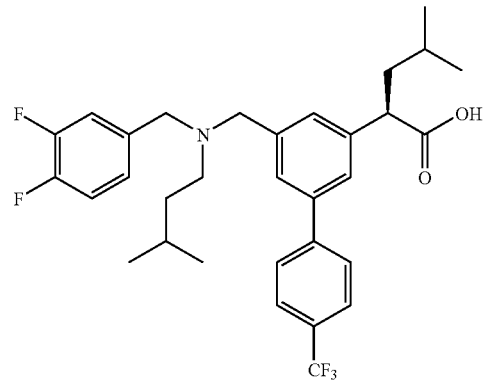

a) 2-(5-Cyano-4'-trifluoromethyl-biphenyl-3-yl)-4-methyl-pentanoic acid ethyl ester

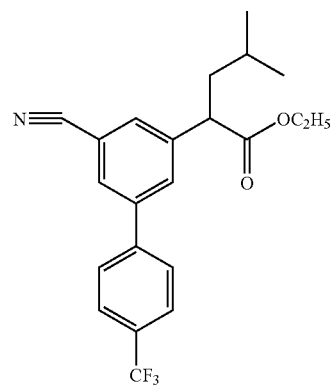

Following a literature procedure (Chackal-Catoen, S. et al. Bioorg. Med. Chem. 2006, 14, 7434), solution of compound 1g (2.18 g, 4.21 mmol) in 19.5 mL of DMF was added to a sealed tube, and zinc cyanide (1.04 g, 8.84 mmol) was added.

The resulting suspension was degassed with argon for 10 min, and then tetrakis(triphenylphosphine) palladium (0) (0.49 g, 0.421 mmol) was added. The reaction flask was placed in a preheated 150° C. oil bath and was heated 24 hours. After this period, the reaction mixture was cooled and saturated aqueous $NaHCO_3$ solution was added. The aqueous layer was extracted with EtOAc three times. The organic extracts were combined and washed five times with brine. After drying over $MgSO_4$ and filtration, the resulting solution was concentrated in vacuo to provide 2.05 g of a golden brown oil. This material was purified on an ISCO chromatographic system using pure hexanes to 2:1 hexanes:ethyl acetate gradient as eluent to yield 0.93 g (57%) of 2-(5-isocyano-4'-trifluoromethyl-biphenyl-3-yl)-4-methyl-pentanoic acid ethyl ester as a colorless oil.

MH+ 390.3

$^1$H NMR (300 MHz, $CDCl_3$): δ0.94 (dd, J=6.6, 1.6 Hz, 6H), 1.25 (t, J=7.2 Hz, 3H), 1.42-1.55 (m, 1H), 1.63-1.76 (m, 1H), 1.96-2.10 (m, 1H), 3.75 (t, J=7.8 Hz, 1H), 4.04-4.28 (m, 2H), 7.62-7.71 (m, 3H), 7.73 (br s, 1H), 7.74-7.79 (m, 3H).

b) 2-(5-Aminomethyl-4'-trifluoromethyl-biphenyl-3-yl)-4-methyl-pentanoic acid ethyl ester

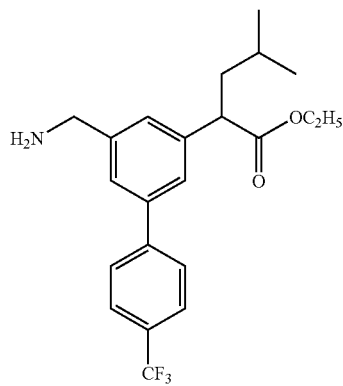

Following a literature procedure (Suh, Y.-G. et al. *J. Med. Chem.* 2005, 18, 7434), solution of compound 5a (0.28 g, 0.719 mmol) was dissolved in 20 mL of ethanol in a Parr hydrogenation bottle. The solution was cooled in ice, and 10% palladium on carbon (0.026 g) and concentrated (12 N) hydrochloric acid solution (0.48 mL) was added. The flask was shaken on a Parr hydrogenation apparatus at 14.5 psi for 5.25 h. After the reaction was terminated, the reaction mixture was filtered through Celite® 545 filter aid. The filtrate was concentrated in vacuo to afford a cream-colored solid. This material was dissolved in dichloromethane, and the resulting solution was washed twice with saturated aqueous $Na_2CO_3$ solution. After drying over $Na_2SO_4$ and subsequent filtration, the resulting solution was concentrated in vacuo to provide 0.28 g (quantitative yield) of 2-(5-aminomethyl-4'-trifluoromethyl-biphenyl-3-yl)-4-methyl-pentanoic acid ethyl ester as a light grey oil.

MH+ 394.4

$^1$H NMR (300 MHz, $CDCl_3$): δ0.93 (br d, J=6.2 Hz, 6H), 1.23 (br t, J=7.0 Hz, 3H), 1.42-1.60 (m, 1H), 1.62-1.78 (m, 1H), 1.95-2.12 (m, 1H), 2.40-2.85 (br s, 2H), 3.75 (m, 1H), 3.96 (br s, 2H), 3.96-4.23 (br m, 2H), 7.34 (br s, 1H), 7.45 (br s, 1H), 7.48 (br s, 1H), 7.68 (br s, 4H).

c) 4-Methyl-2-{5-[(3-methyl-butylamino)-methyl]-4'-trifluoromethyl-biphenyl-3-yl}-pentanoic acid ethyl ester

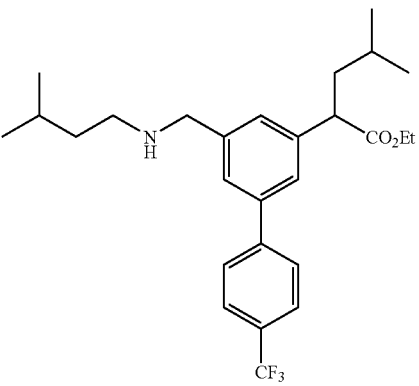

To a solution of compound 5b (0.24 g, 0.610 mmol) in 10 mL of anhydrous methanol, was added isovaleroaldehyde (0.058 g, 0.07 mL, 0.671 mmol). The solution was stirred 45 minutes, and then sodium borohydride (0.046 g, 1.22 mmol) was added. After 20 h of stirring, the reaction mixture was cooled in ice, and HCl (1 N solution, 1 mL) was added. The reaction mixture was stirred for one minute, and then saturated aqueous $Na_2CO_3$ solution was added until the pH was basic. The solution was extracted three times with dichloromethane. The organic extracts were combined and washed with saturated aqueous $Na_2CO_3$ solution, dried ($Na_2SO_4$), and filtered. The filtrate was concentrated to provide a 0.27 g of a pale yellow glass. Purification on a flash silica gel column using 95:4.5:0.5 $CH_2Cl_2$:MeOH:$NH_4OH$ provided 0.25 g (89%) of 4-methyl-2-{5-[(3-methyl-butylamino)-methyl]-4'-trifluoromethyl-biphenyl-3-yl}-pentanoic acid ethyl ester as a colorless oil.

MH+ 464.4

$^1$H NMR (300 MHz, $CDCl_3$): δ0.89 (d, J=6.7 Hz, 6H), 0.93 (d, J=6.6 Hz, 6H), 1.23 (t, J=7.1 Hz, 3H), 1.39-1.59 (m, 3H), 1.58-1.75 (m, 2H), 1.96-2.08 (m, 2H), 2.68 (br t, J=7.5 Hz, 2H), 3.71 (dd, J=7.3, 1.1 Hz 1H), 3.87 (s, 2H), 3.96 (br s, 2H), 4.02-4.23 (br m, 2H), 7.32 (br s, 1H), 7.45 (br d, J=1.5 Hz, 1H), 7.49 (br s, 1H), 7.69 (AB quartet, J=9.1 Hz, 4H).

f) 2-(5-{[(3,4-Difluoro-benzyl)-(3-methyl-butyl)-amino]-methyl}-4'-trifluoromethyl-biphenyl-3-yl)-4-methyl-pentanoic acid ethyl ester

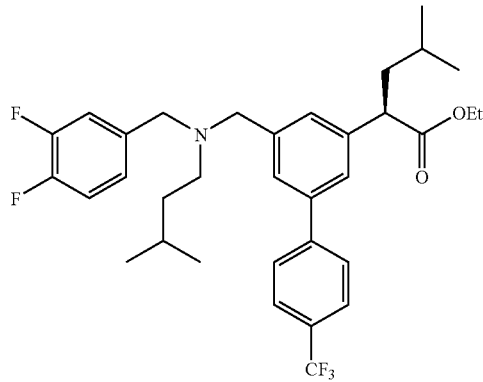

To a solution of compound 5c (0.037 g, 0.091 mmol) in 5 mL of anhydrous dichloromethane was added 4,5-difluorobenzaldehyde (0.029 g, 0.182 mmol). The reaction mixture was stirred 30 minutes, and then sodium triacetoxyborohydride (0.0385 g, 0.182 mmol) was added. After 18 h, 1N NaOH solution was added to the reaction mixture. The resulting mixture was extracted three times with dichloromethane. The organic extracts were combined and washed with 1N NaOH solution, dried (Na$_2$SO$_4$), filtered, and concentrated to yield a cloudy film. Purification on a flash silica gel column using 1% (5% NH$_4$OH in MeOH): CH$_2$Cl$_2$ yielded the title compound e) 4-Methyl-2-(5-{[(3-methyl-butyl)-(4,5-trifluoro-benzyl)-amino]-methyl}-4'-trifluoromethyl-biphenyl-3-yl)-pentanoic acid To a solution of compound 5d in 5 mL of methanol was added 3N NaOH solution (0.1 mL). The mixture was heated to 60° C. for 3 h. After cooling to ambient temperature, the reaction mixture was concentrated in vacuo. To the residue was added 3N HCl solution. This solution was extracted three times with dichloromethane. The organic extracts were combined, dried (Na$_2$SO$_4$), filtered, and concentrated to provide a milky film. Analysis by LC-MS indicated this material was a 1:2 mixture of the desired acid and the corresponding methyl ester. This material was resubjected to the reaction conditions described above for 4 h and then the reaction mixture was heated to 80° C. for 6 h. After cooling, the workup described before provided the title compound.

EXAMPLE 6

2-{5-[(5-Chloro-pyridin-2-yl)-(3-methyl-butyl)-amino]-4'-trifluoromethyl-biphenyl-3-yl}-4-methyl-pentanoic acid

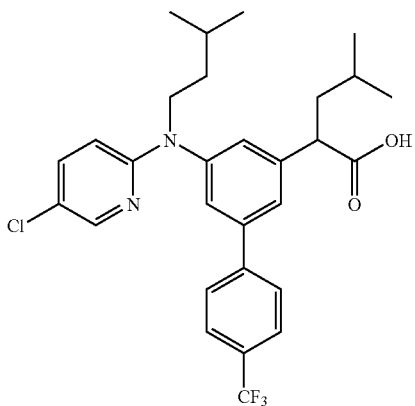

Replacing 4-chloro-aniline with 2-amino-5-chloro-pyridine and MeI with 1-iodo-3-methyl-butane following the same procedure as in the preparation of Example 1 gave the title compound; 1H NMR (400 MHz, CHLOROFORM-D) δ 0.86-0.96 (m, 12H), 1.48-1.58 (m, 3H), 1.58-1.67 (m, 1H), 1.68-1.78 (m, 1H), 2.00 (dt, J=13.69, 7.58 Hz, 1H), 3.73 (t, J=7.83 Hz, 1H), 3.91-4.00 (m, 2H), 6.43 (d, J=9.05 Hz, 1H), 7.21-7.26 (m, 1H), 7.34-7.41 (m, 2H), 7.67 (q, J=8.56 Hz, 5H), 8.14 (d, J=2.20 Hz, 1H); Calcd for C29H32ClF3N2O2 (M+H) 533.21. Found 533.1.

2-{5-[(5-Chloro-pyridin-2-yl)-isobutyl-amino]-4'-trifluoromethyl-biphenyl-3-yl}-4-methyl-pentanoic acid

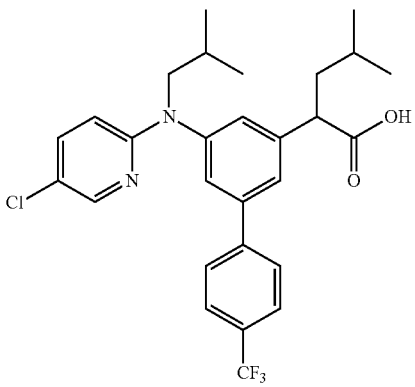

EXAMPLE 7

2-{5-[(4-Isopropyl-phenyl)-methyl-amino]-4'-trifluoromethyl-biphenyl-3-yl}-4-methyl-pentanoic acid

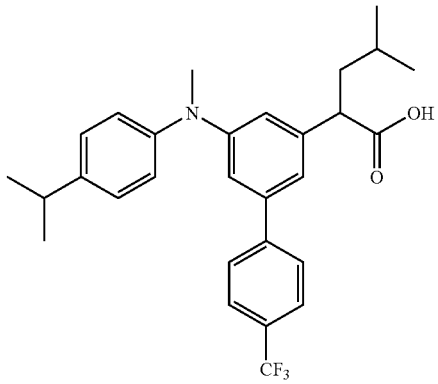

Replacing 3-trifluoromethyl-aniline with 4-isopropyl-aniline following the same procedure as Example 2 gave the title compound 7; 1H NMR (400 MHz, MeOD) δ ppm 0.76-0.85 (m, 6H), 1.10-1.22 (m, 6H), 1.42 (dt, J=13.45, 6.72 Hz, 1H), 1.49-1.59 (m, 1H), 1.81 (dt, J=13.45, 7.58 Hz, 1H), 2.74-2.85 (m, 1H), 3.24 (s, 3H), 3.53 (t, J=7.83 Hz, 1H), 6.79-6.82 (m, 1H), 6.92-7.00 (m, 4H), 7.06-7.15 (m, 2H), 7.55-7.65 (m, 4H); Calcd for C29H32F3NO2 (M+H) 484.24. Found 484.2.

EXAMPLE 8

2-{5-[(4-Cyano-phenyl)-methyl-amino]-4'-trifluoromethyl-biphenyl-3-yl}-4-methyl-pentanoic acid

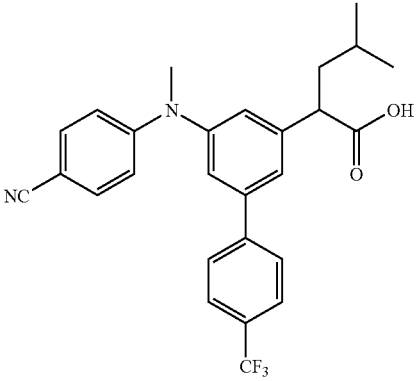

Replacing 3-trifluoromethyl-aniline with 4-cyano-aniline following the same procedure as in the preparation of Example 2 gave the title compound 8; 1H NMR (400 MHz, MeOD) δ ppm 0.76-0.87 (m, 6H), 1.43 (dt, J=13.39, 6.63 Hz, 1H), 1.59 (ddd, J=13.63, 7.09, 6.91 Hz, 1H), 1.81-1.93 (m, 1H), 3.26-3.33 (s, 3H), 3.67 (t, J=7.70 Hz, 1H), 6.77 (d, J=8.80 Hz, 2H), 7.18 (d, J=1.47 Hz, 1H), 7.35 (d, J=1.71 Hz, 1H), 7.37 (d, J=9.05 Hz, 2H), 7.44 (d, J=1.47 Hz, 1H), 7.60-7.72 (m, 4H); Calcd for C27H25F3N2O2 (M+H) 467.19. Found 467.3.

EXAMPLE 9

2-{5-[(4-Chloro-3-trifluoromethyl-phenyl)-methyl-amino]-4'-trifluoromethyl-biphenyl-3-yl}-4-methyl-pentanoic acid

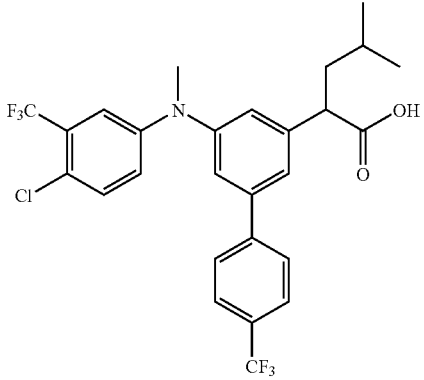

Replacing 3-trifluoromethyl-aniline with 4-chloro-3-trifluoromethyl-aniline following the same procedure as in Example 2 gave the title compound 9; 1H NMR (400 MHz, MeOD) δ ppm 0.75-0.86 (m, 6H), 1.41 (dt, J=13.45, 6.72 Hz, 1H), 1.54-1.63 (m, 1H), 1.79-1.91 (m, 1H), 3.20 (ddd, J=3.30, 1.59, 1.47 Hz, 2H) 3.29 (s, 3H), 3.63 (t, J=7.83 Hz, 1H), 7.01 (dd, J=8.93, 2.81 Hz, 1H), 7.11 (dd, J=9.54, 2.20 Hz, 2H), 7.22-7.33 (m, 3H), 7.59-7.70 (m, 4H); Calcd for C27H24ClF6NO2 (M+H) 544.14. Found 544.2.

EXAMPLE 10

2-{5-[(3,5-Bis-trifluoromethyl-phenyl)-methyl-amino]-4'-trifluoromethyl-biphenyl-3-yl}-4-methyl-pentanoic acid

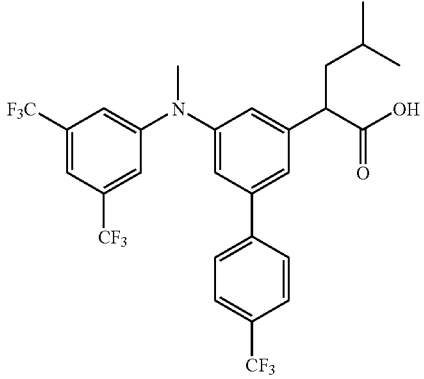

Replacing 3-trifluoromethyl-aniline with 3,5-bis-trifluoromethyl-aniline following the same procedure as in Example 2 gave the title compound 10; 1H NMR (400 MHz, MeOD) δ ppm 0.75-0.86 (m, 6H), 1.41 (dt, J=13.39, 6.63 Hz, 1H), 1.56-1.66 (m, 1H), 1.80-1.91 (m, 1H), 3.35 (s, 3H), 3.66 (t, J=7.83 Hz, 1H), 7.12-7.21 (m, 4H), 7.37 (d, J=1.47 Hz, 1H), 7.43 (s, 1H), 7.62-7.73 (m, 4H); Calcd for C28H24F9NO2 (M+H) 578.17. Found 578.1.

EXAMPLE 11

2-{5-[(4-Fluoro-2-trifluoromethyl-phenyl)-methyl-amino]-4'-trifluoromethyl-biphenyl-3-yl}-4-methyl-pentanoic acid

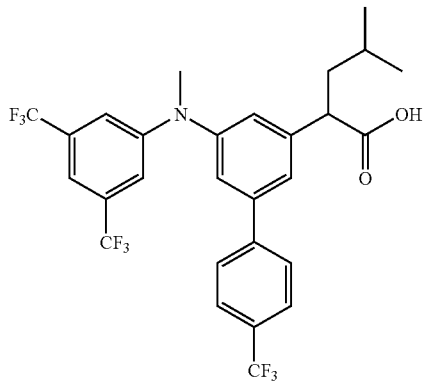

Replacing 3-trifluoromethyl-aniline with 4-fluoro-2-trifluoromethyl-aniline following the same procedure as in Example 2 gave the title compound 11; 1H NMR (400 MHz, MeOD) δ ppm 0.80 (d, J=6.60 Hz, 6H), 1.37 (dt, J=13.27, 6.69 Hz, 1H), 1.44-1.55 (m, 1H), 1.69-1.81 (m, 1H), 3.13 (s, 3H), 3.48 (t, J=7.83 Hz, 1H), 6.41 (s, 1H), 6.57 (s, 1H), 6.89 (s, 1H), 7.24-7.35 (m, 1H), 7.39 (td, J=8.25, 2.81 Hz, 1H), 7.49-7.61 (m, 5H); Calcd for C27H24F7NO2 (M+H) 528.17. Found 528.2.

EXAMPLE 12

2-{5-[(2,5-Bis-trifluoromethyl-phenyl)-methyl-amino]-4'-trifluoromethyl-biphenyl-3-yl}-4-methyl-pentanoic acid

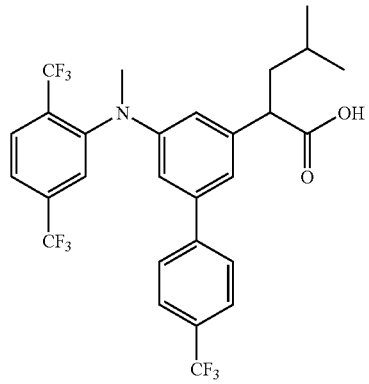

Replacing 3-trifluoromethyl-aniline with 2,5-bis-trifluoromethyl-aniline following the same procedure as in Example 2 gave the title compound 12; 1H NMR (400 MHz, MeOD) δ ppm 0.74-0.85 (m, 6H), 1.35 (ddd, J=13.33, 6.85, 6.72 Hz, 1H), 1.43-1.54 (m, 1H), 1.74 (ddd, J=13.57, 7.58, 7.46 Hz, 1H), 3.19 (s, 3H), 3.48 (t, J=7.83 Hz, 1H), 6.39 (s, 1H), 6.68 (d, J=1.71 Hz, 1H), 6.96 (s, 1H), 7.61 (s, 5H), 7.78 (d, J=8.07 Hz, 1 H), 7.98 (d, J=8.31 Hz, 1H); Calcd for C28H24F9NO2 (M+H) 578.17. Found 578.1.

EXAMPLE 13

2-{5-[Ethyl-(3-trifluoromethyl-phenyl)-amino]-4'-trifluoromethyl-biphenyl-3-yl}-4-methyl-pentanoic acid

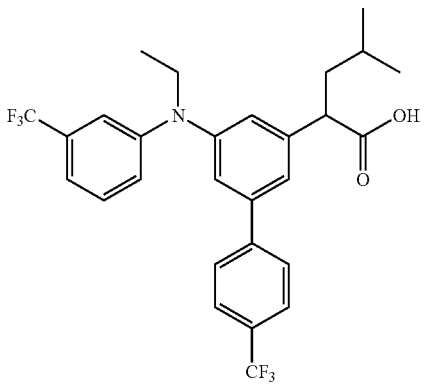

Replacing methyl iodide with ethyl iodide following the same procedure as in Example 2 gave the title compound; 1H NMR (400 MHz, MeOD) δ ppm 0.76-0.87 (m, 6H), 1.13-1.24 (m, 3H), 1.38-1.49 (m, 1H), 1.56-1.64 (m, 1H), 1.79-1.90 (m, 1 H), 3.62 (t, J=7.83 Hz, 1H), 3.82 (q, J=7.09 Hz, 2H), 6.99-7.10 (m, 4H), 7.25-7.33 (m, 3H), 7.66 (q, J=8.64 Hz, 4H); Calcd for C28H27F6NO2 (M+H) 524.19. Found 524.1.

EXAMPLE 14

2-{5-[(4-Chloro-phenyl)-ethyl-amino]-4'-trifluoromethyl-biphenyl-3-yl}-4-methyl-pentanoic acid

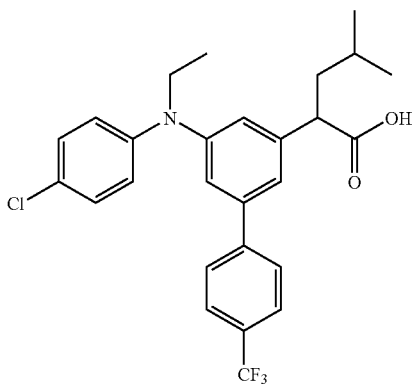

Replacing 3-trifluoromethyl-aniline with 4-chloro-aniline, methyl iodide with ethyl iodide following the same procedure as in Example 2 gave the title compound 14; 1H NMR (400 MHz, MeOD) δ ppm 0.76-0.87 (m, 6H), 1.12-1.23 (m, 3H), 1.42 (dt, J=13.39, 6.63 Hz, 1H), 1.50-1.61 (m, 1H), 1.78-1.90 (m, 1H), 3.54-3.60 (m, 1H), 3.75 (q, J=7.09 Hz, 2H), 6.88- 6.96 (m, 3H), 7.03-7.08 (m, 1H), 7.09-7.18 (m, 3H), 7.57-7.65 (m, 4H); Calcd for C28H27F6NO2 (M+H) 524.19. Found 524.1.

EXAMPLE 15

4-Methyl-2-{5-[methyl-(6-trifluoromethyl-pyridin-3-yl)-amino]-4'-trifluoromethyl-biphenyl-3-yl}-pentanoic acid

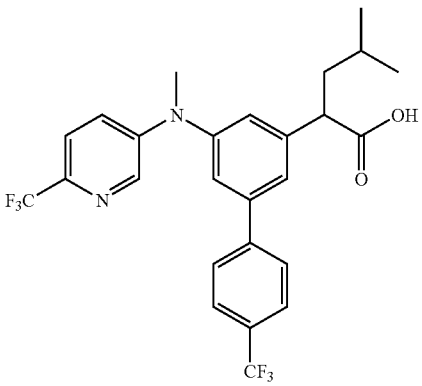

Replacing 3-trifluoromethyl-aniline with 6-trifluoromethyl-3-amino-pyridine following the same procedure as in Example 2 gave the title compound 15; 1H NMR (400 MHz, MeOD) δ ppm 0.79-0.89 (m, 6H), 1.14-1.24 (m, 1H), 1.44 (dt, J=13.21, 6.60 Hz, 1H), 1.61 (ddd, J=13.82, 7.09, 6.97 Hz, 1H), 1.88 (ddd, J=13.57, 7.70, 7.58 Hz, 1H), 3.36 (s, 3H), 3.69 (t, J=7.83 Hz, 1H), 7.21-7.28 (m, 2H), 7.40-7.44 (m, 1 H), 7.47 (s, 1H), 7.51 (d, J=9.05 Hz, 1H), 7.62-7.68 (m, 2H), 7.68-7.76 (m, 2H), 8.06 (d, J=2.93 Hz, 1H); Calcd for C26H24F6N2O2 (M+H) 511.17. Found 511.2.

EXAMPLE 16

4-{[5-(1-Carboxy-3-methyl-butyl)-4'-trifluoromethyl-biphenyl-3-yl]-methyl-amino}-1-methyl-pyridinium

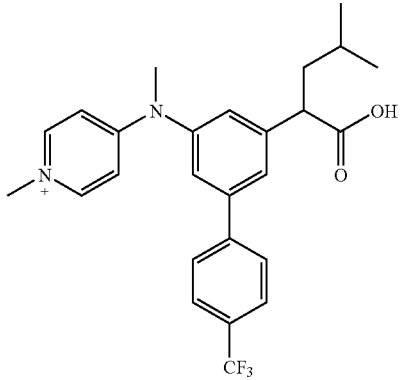

Replacing 3-trifluoromethyl-aniline with 4-amino-pyridine following the same procedure as in Example 2 gave the title compound 16; 1H NMR (400 MHz, MeOD) δ ppm 0.99 (d, J=6.60 Hz, 6H), 1.53-1.61 (m, 1H), 1.72-1.80 (m, 1H), 1.99-2.09 (m, 1H), 3.62 (s, 3H), 3.89 (t, J=7.83 Hz, 1H), 4.01 (s, 3H), 6.96 (m, 2H), 7.44 (s, 1H), 7.64 (s, 1H), 7.76-7.84 (m, 3H), 7.84-7.90 (m, 2H), 8.16 (s, 2H); Calcd for C26H28F3N2O2 (M+H) 458.21. Found 458.3.

EXAMPLE 17

4-Methyl-2-{5-[(3-methyl-butyl)-(3-trifluoromethyl-phenyl)-amino]-4'-trifluoromethyl-biphenyl-3-yl}-pentanoic acid

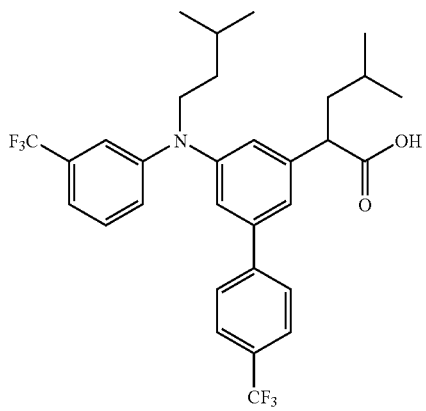

Replacing methyl iodide with 1-iodo-3-methyl-butane following the same procedure as in Example 2 gave the title compound 17; 1H NMR (400 MHz, MeOD) δ ppm 0.84-0.94 (m, 12H), 1.41-1.75 (m, 5H), 1.81-1.85 (m, 1H), 3.62 (t, J=7.83 Hz, 1H), 3.73-3.79 (m, 2H), 6.90-7.10 (m, 4H), 7.20 (s, 1H), 7.28-7.31 (m, 2H), 7.66 (d, J=4.40 Hz, 4H); Calcd for C31H33F6NO2 (M+H) 566.24. Found 566.2.

EXAMPLE 18

2-{5-[(4-Chloro-phenyl)-(3-methyl-butyl)-amino]-4'-trifluoromethyl-biphenyl-3-yl}-4-methyl-pentanoic acid

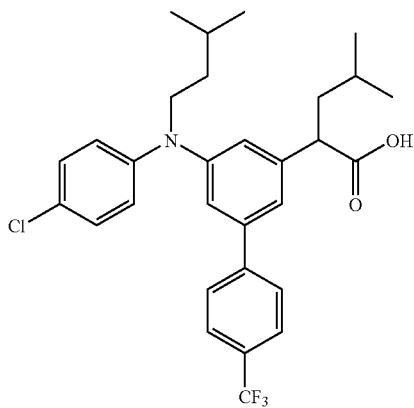

Replacing 3-trifluoromethyl-aniline with 4-chloroaniline and then replacing methyl iodide with 1-iodo-3-methyl-butane following the same procedure as in Example 2 gave the title compound 18; ¹H NMR (400 MHz, MeOD) δ ppm 0.78-0.89 (m, 12H), 1.41-1.53 (m, 3H), 1.56-1.64 (m, 2H), 1.83 (dt, J=13.51, 7.55 Hz, 1H), 3.59 (t, J=7.83 Hz, 1H), 3.68-3.74 (m, 2H), 6.91-6.96 (m, 3H), 7.04 (s, 1H), 7.11 (s, 1H), 7.15-7.19 (m, 2H), 7.63 (s, 4H); Calcd for C30H33ClF3NO2 (M+H) 532.22. Found 532.

EXAMPLE 19

4-Methyl-2-{5-[methyl-(4-trifluoromethyl-phenyl)-amino]-4'-trifluoromethyl-biphenyl-3-yl}-pentanoic acid

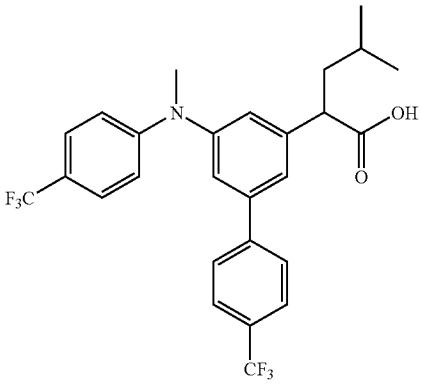

a) 4-Methyl-2-[4'-trifluoromethyl-5-(4-trifluoromethyl-phenylamino)-biphenyl-3-yl]-pentanoic acid ethyl ester

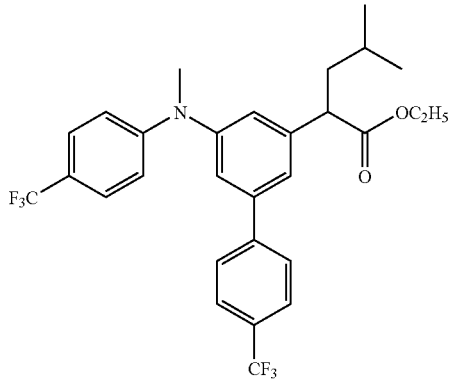

A mixture of compound 1g (50 mg, 0.098 mmol), 4-trifluoromethyl-aniline (25 mg, 0.156 mmol), Pd(OAc)₂ (6.6 mg, 0.029 mmol), racemic-2-(di-t-butylphosphino)-1,1'-binaphthyl (35 mg, 0.088 mmol) and NaOt-Bu (11.3 mg, 0.12 mmol) in toluene (1.5 mL) was heated to 150° C. under microwave irradiation (300 w, 250 psi) for 20 min. After cooling to room temperature, the solution was partitioned between EtOAc and H₂O. The organic layer was dried (Na₂SO₄), concentrated and purified by column chromatography to give the title compound.

b) 4-Methyl-2-{5-[methyl-(4-trifluoromethyl-phenyl)-amino]-4'-trifluoromethyl-biphenyl-3-yl}-pentanoic acid To a solution of the above aniline ester intermediate (40 mg, 0.076 mmol) in acetonitrile (1 mL) was added methyl iodide (0.048 mL, 0.76 mmol) and Et₃N (0.032 mL, 0.228 mmol). The mixture was heated to 85° C. for 17 h. After cooling to room temperature, the solution was partitioned between EtOAc and H₂O. The organic layer was dried (Na₂SO₄), concentrated and purified by column chromatography to give an ethyl ester intermediate.

A mixture of the above intermediate and NaOH solution (2N in H₂O, 0.114 mL, 0.228 mmol) in THF-MeOH (0.6 mL-0.6 mL) was stirred for 18 h and concentrated. CH₂Cl₂ and water were added, and the mixture was acidified with 1N HCl. The organic phase was separated and the aqueous phase was extracted with $CH_2Cl_2$. The combined organic layers were dried, concentrated, and purified by column chromatography to give 30 mg (60%, 3 steps) of the title compound as a white solid; 1H NMR (400 MHz, MeOD) δ 0.86 (d, J=6.60 Hz, 6H), 1.41-1.50 (m, 1H), 1.57-1.65 (m, 1H), 1.84-1.92 (m, 1H), 3.22 (s, 3H), 3.62-3.70 (m, 1H), 6.88 (d, J=8.80 Hz, 2H), 7.17 (d, J=1.71 Hz, 1H), 7.30-7.39 (m, 4H), 7.62-7.72 (m, 4H); Calcd for C27H25F6NO2 (M+H) 510.18. Found 510.

EXAMPLE 20

4-Methyl-2-{5-[(3-methyl-butyl)-(4-trifluoromethyl-phenyl)-amino]-4'-trifluoromethyl-biphenyl-3-yl}-pentanoic acid

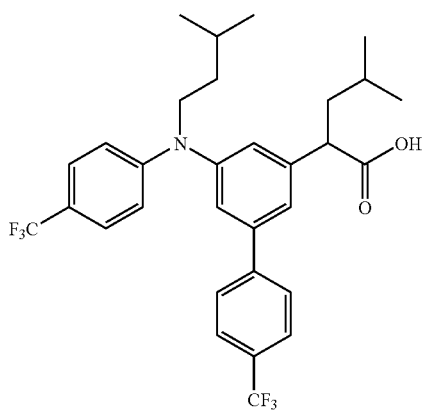

Following the procedure of Example 19, reaction of compound 19a with 1-iodo-3-methyl-butane and $Cs_2CO_3$ in $CH_3CN$ and followed the ester hydrolysis gave the title compound; 1H NMR (400 MHz, MeOD) δ 0.87-0.96 (m, 12H), 1.51-1.74 (m, 5H), 1.96 (dt, J=13.69, 7.58 Hz, 1H), 3.75 (t, J=7.83 Hz, 1H), 3.80-3.86 (m, 2H), 6.92 (d, J=8.56 Hz, 2H), 7.22-7.26 (m, 1H), 7.36-7.46 (m, 4H), 7.70-7.78 (m, 4H); Calcd for C31H33F6NO2 (M+H) 566.24. Found 566.

EXAMPLE 21

(R*)2-{5-[(4-Chloro-phenyl)-methyl-amino]-4'-trifluoromethyl-biphenyl-3-yl}-4-methyl-pentanoic acid

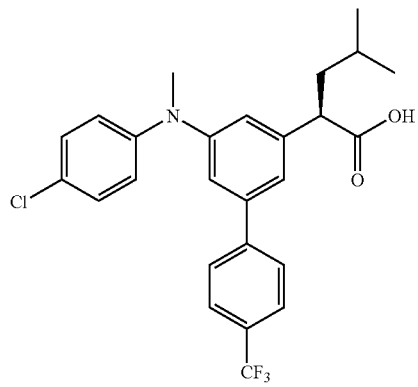

Racemic compound 1 was separated with a chiralpad AD-H column using heptane-ethanol-TFA (0.1%) to give the two enantiomers. The first peak eluted from the chiral column was assigned as R* isomer (absolute stereo chemistry of C-2 has not been determined).

EXAMPLE 22

(S*)2-{5-[(4-Chloro-phenyl)-methyl-amino]-4'-trifluoromethyl-biphenyl-3-yl}-4-methyl-pentanoic acid

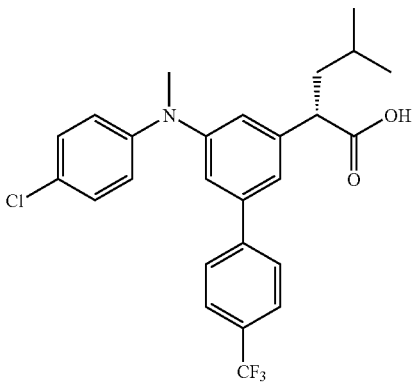

Racemic compound 1 was separated with a chiralpad AD-H column using heptane-ethanol-TFA (0.1%) to give the two enantiomers. The second peak eluted from the chiral column was assigned as S* isomer (absolute stereo chemistry of C-2 has not been determined).

EXAMPLE 23

2-{5-[(4-Chloro-phenyl)-(3-methyl-butyryl)-amino]-4'-trifluoromethyl-biphenyl-3-yl}-4-methyl-pentanoic acid

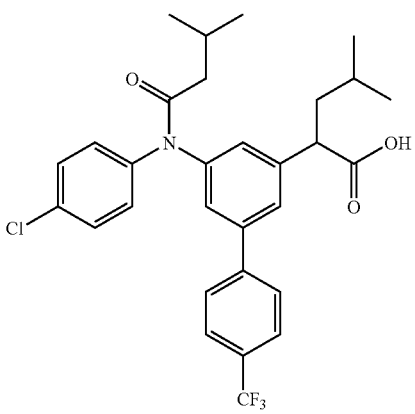

To a solution of 2-[5-(4-chloro-phenylamino)-4'-trifluoromethyl-biphenyl-3-yl]-4-methyl-pentanoic acid (51.1 mg, 0.11 mmol), sodium acetate 40 mg, 1.1 mmol) and toluene (0.5 mL) was added isovaleryl chloride (60 μL, 0.55 mmol) and the resulting mixture was stirred at RT for 48 hr. The mixture was treated with water (10 mL) and extracted with EtOAc (2×25 mL). The combined organic layers were dried with $MgSO_4$, filtered and the solvent was concentrated in vacuo and the residue was purified by flash chromatography on silica gel (gradient 0% to 30% EtOAc/heptane) to afford 16.3 mg (27%) of the title compound as a solid. $^1$H-NMR (CDCl$_3$; 300 MHz): δ 7.6-7.7 (m, 4H), 6.98-7.45 (m, 7H), 3.7

(m, 1H), 2.2 (m, 2H), 2.0 (m, 1H), 1.7 (m, 1H), 1.5 (m, 1H), 1.25 (bs, 1H), 0.85-1.0 (m, 12H). Mass spectrum (ESI, m/z): Calcd. for $C_{30}H_{31}ClF_3NO_3$, 546.03 (M+H), found 548.26, 546.29.

EXAMPLE 24

2-[5-(2,3-Dihydro-indol-1-yl)-4'-trifluoromethyl-biphenyl-3-yl]-4-methyl-pentanoic acid

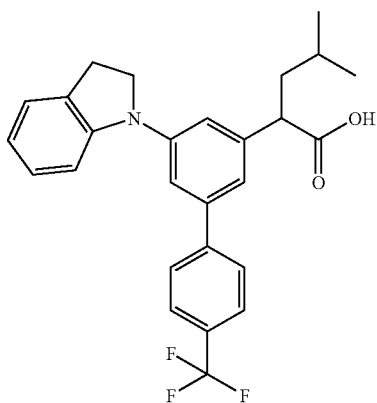

a) 2-[5-(2,3-Dihydro-indol-1-yl)-4'-trifluoromethyl-biphenyl-3-yl]-4-methyl-pentanoic acid methyl ester

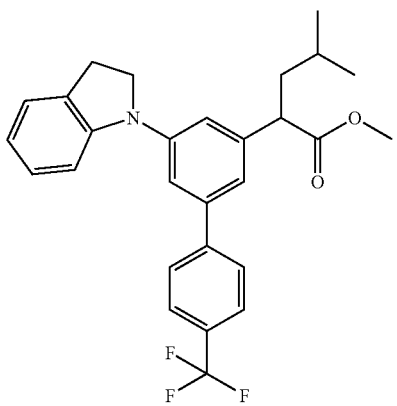

A solution of $Pd(OAc)_2$ (6 mg, 0.025 mmol) and rac-BINAP (23 mg, 0.037 mmol) in THF (2.5 mL) was stirred under nitrogen for 10 min. $Cs_2CO_3$ (95 mg, 0.29 mmol), 4-methyl-2-(5-trifluoromethanesulfonyloxy-4'-trifluoromethyl-biphenyl-3-yl)-pentanoic acid methyl ester (100 mg, 0.21 mmol) and indoline (0.028 mL, 0.25 mmol) were added and the reaction mixture was stirred under nitrogen at 65° C. for 48 h. The solution was then partitioned between EtOAc (10 mL) and $H_2O$ (10 mL). The aqueous layer was extracted with EtOAc (2×10 mL). The organic layers were washed with brine, dried ($MgSO_4$) and concentrated to yield an oil. The residue was purified by flash chromatography (0 to 10% EtOAc in petroleum ether) to give the title compound. The resulting oil was used crude in the next step.

b) 2-[5-(2,3-Dihydro-indol-1-yl)-4'-trifluoromethyl-biphenyl-3-yl]-4-methyl-pentanoic acid A solution of 2-[5-(2,3-dihydro-indol-1-yl)-4'-trifluoromethyl-biphenyl-3-yl]-4-methyl-pentanoic acid methyl ester, MeOH (1 mL), THF (1 mL) and 10% aq. LiOH solution (0.5 mL) was stirred at 40° C. overnight. The solution was then acidified with aq. 2M HCl and extracted with DCM (3×1 mL). The organic layers were filtered through PTFE filter and concentrated to yield an oil. The residue was purified using reverse phase preparative HPLC ($H_2O$: MeCN) to give the title product in 8% yield as a yellow oil.
$^1$H-NMR (400 MHz, $CD_3Cl$): δ 7.68 (s, 4H), 7.31 (s, 1H), 7.25 (s, 1H), 7.20-7.07 (m, 4H), 6.78 (t, 1H), 4.01 (t, 2H), 3.73 (t, 1H), 3.15 (t, 2H), 2.05-1.98 (m, 1H), 1.80-1.73 (m, 1H), 1.62-1.55 (m, 1H), 0.95 (d, 6H).

EXAMPLE 25

2-[5'-Fluoro-5-(N-[3,5-bis-(trifluoromethyl)phenyl]-N-methylamino)-3'-trifluoromethyl-biphenyl-3-yl]-4-methyl-pentanoic acid

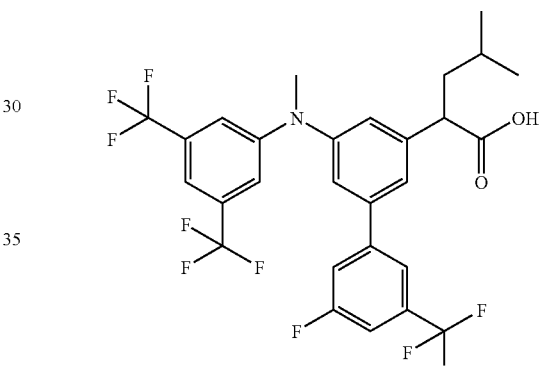

a) 2-(3'-Fluoro-5-trifluoromethanesulfonyloxy-5'-trifluoromethyl-biphenyl-3-yl)-4-methyl-pentanoic acid methyl ester

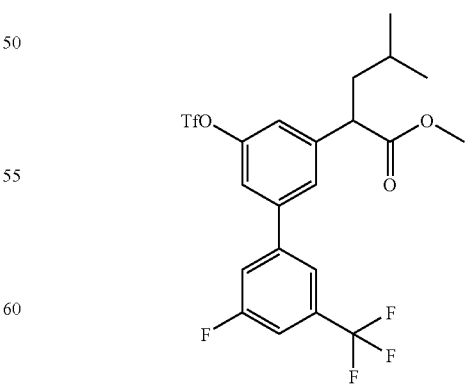

The title compound was prepared in 66% yield from 2-(3-benzyloxy-5-trifluoromethanesulfonyloxy-phenyl)-4-methyl-pent-4-enoic acid methyl ester (prepared in Example 1, step (d)) under the conditions described in Example 1, step (e-g)) using 3-fluoro-5-trifluoromethylphenylboronic acid in step (e).

¹H-NMR (400 MHz, CD₃Cl): δ ¹H-NMR (400 MHz, CDCl₃): δ 7.58 (s, 1H), 7.53 (m, 1H), 7.44 (dm, 1H, J=9.1 Hz), 7.39 (m, 1H), 7.36 (m, 1H), 7.33 (m, 1H), 3.78 (m, 1H), 3.70 (s, 3H), 2.03 (m, 1H), 1.71 (m, 1H), 1.49 (m, 1H), 0.94 (d, 6H, J=6.8 Hz). RT=4.10 min b) 2-[5'-Fluoro-5-(3,5-bis-trifluoromethyl-phenylamino)-3'-trifluoromethyl-biphenyl-3-yl]-4-methyl-pentanoic acid methyl ester

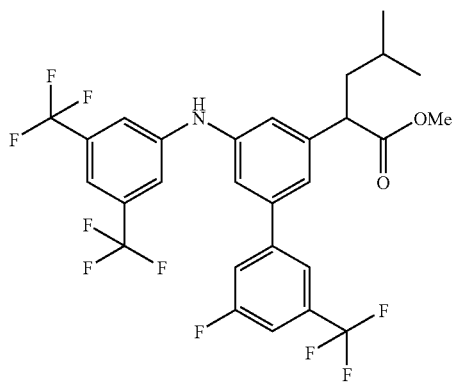

A mixture of 2-(3'-fluoro-5-trifluoromethanesulfonyloxy-5'-trifluoromethyl-biphenyl-3-yl)-4-methyl-pentanoic acid methyl ester (48 mg, 0.10 mmol), 3,5-bis-(trifluoromethyl) aniline (18 μL, 0.12 mmol), sodium tert-butoxide (9.8 mg, 0.10 mmol), Pd(OAc)₂ (2.5 mg, 0.01 mmol), 2-(di-tert-butylphosphino-1,1'-binaphthyl (3.5 mg, 0.01 mmol) and toluene (1 mL) was stirred under microwave irradiation at 130° C. for 3×10 min. The mixture was diluted with toluene (9 mL), washed with 1M HCl (2×10 mL) and brine (10 mL), dried (MgSO₄), concentrated in vacuo and purified by flash column chromatography (Et₂O-petroleum ether) to afford the title product as a colourless powder (28 mg, 44%). RT=4.97 min.

c) 2-[5'-Fluoro-5-(N-[3,5-bis-(trifluoromethyl)phenyl]-N-methylamino)-3'-trifluoromethyl-biphenyl-3-yl]-4-methyl-pentanoic acid methyl ester

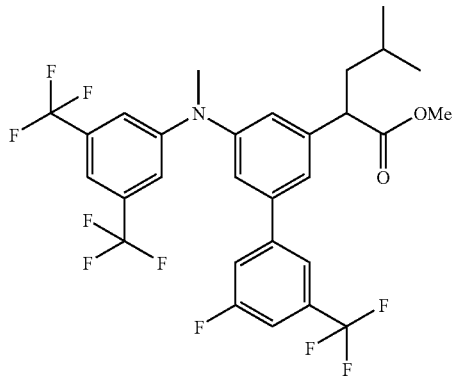

A mixture of 2-[5'-fluoro-5-(3,5-bis-trifluoromethyl-phenylamino)-3'-trifluoromethyl-biphenyl-3-yl]-4-methyl-pentanoic acid methyl ester (57 mg, 0.096 mmol), potassium tert-butoxide (58 mg, 0.52 mmol), methyl iodide (60 μL, 0.11 mmol), dioxane (2 mL) and N-methylpyrrolidinone (0.2 mL) was stirred with microwave irradiation for 15 min at 130° C. The mixture was concentrated in vacuo, suspended in 1M HCl (20 mL) and extracted with diethyl ether (2×20 mL). The combined organic layer was washed with brine, dried (MgSO₄), concentrated in vacuo and purified by flash column chromatography (silica, 0-5% diethyl ether in petroleum ether) to afford the title product as a colourless solid (33 mg, 56%). RT=5.24 min.

d) 2-[5'-Fluoro-5-(N-[3,5-bis-(trifluoromethyl)phenyl]-N-methylamino)-3'-trifluoromethyl-biphenyl-3-yl]-4-methyl-pentanoic acid The title compound was prepared in 52% yield from 2-[5'-fluoro-5-(N-[3,5-bis-(trifluoromethyl)phenyl]-N-methylamino)-3'-trifluoromethyl-biphenyl-3-yl]-4-methyl-pentanoic acid methyl ester under the conditions described in Example 24, step (b).

¹H-NMR (400 MHz, CDCl₃): δ 7.70 (d, 1H), 7.58 (m, 2H), 7.42 (d, 1H), 7.32 (d, 1H), 7.20 (m, 3H), 6.31 (br s, 1H), 3.75 (m, 1H), 1.98 (m, 1H), 1.75 (m, 1H), 1.55 (m, 1H), 0.93 (m, 6H); RT=4.25 min. Mass spectrum (ESI, m/z): 596 (M+H);

EXAMPLE 26

4-Methyl-2-[4'-trifluoromethyl-5-(7-trifluoromethyl-3,4-dihydro-2H-quinolin-1-yl)-biphenyl-3-yl]-pentanoic acid

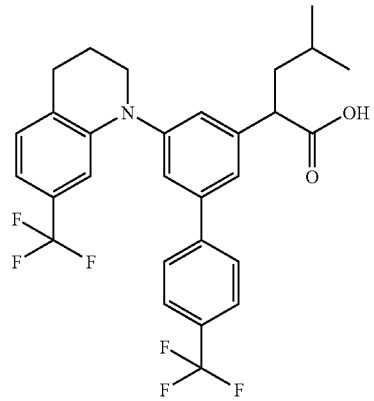

a) 4-Methyl-2-[4'-trifluoromethyl-5-(7-trifluoromethyl-3,4-dihydro-2H-quinolin-1-yl)-biphenyl-3-yl]-pentanoic acid methyl ester

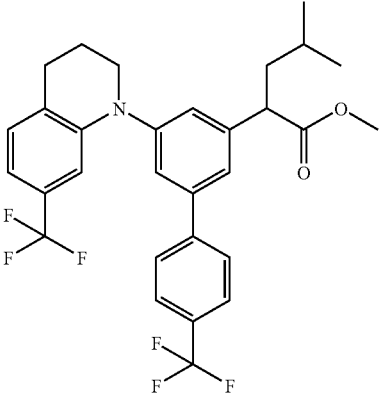

The title compound was prepared in 8% yield from 4-methyl-2-(5-trifluoromethanesulfonyloxy-4'-trifluoromethylbiphenyl-3-yl)-pentanoic acid methyl ester and 7-(trifluoromethyl)-1,2,3,4-tetrahydroquinoline under the conditions described in Example 24, step (a).

b) 4-Methyl-2-[4'-trifluoromethyl-5-(7-trifluoromethyl-3,4-dihydro-2H-quinolin-1-yl)-biphenyl-3-yl]-pentanoic acid The title compound was prepared in 67% yield from 4-methyl-2-[4'-trifluoromethyl-5-(7-trifluoromethyl-3,4-dihydro-2H-quinolin-1-yl)-biphenyl-3-yl]-pentanoic acid methyl ester under the conditions described in Example 24, step (b).
$^1$H-NMR (400 MHz, CD$_3$Cl): δ 7.66 (quartet, 4H), 7.34 (t, 1H), 7.28 (d, 2H), 7.14 (d, 1H), 7.08 (s, 1H), 6.94 (d, 1H), 3.71 (t, 3H), 2.89 (t, 2H), 2.07 (quintet, 2H), 2.02-1.94 (m, 1H), 1.78-1.71 (m, 1H), 1.59-1.54 (m, 1H), 0.93 (d, 6H); RT=4.31 min

EXAMPLE 27

2-[4'-Chloro-5-(N-[3,5-bis-(trifluoromethyl)phenyl]-N-methylamino)-3'-trifluoromethyl-biphenyl-3-yl]-4-methyl-pentanoic acid

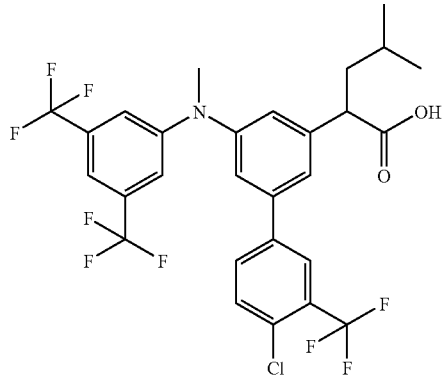

a) 2-(4'-Chloro-5-trifluoromethanesulfonyloxy-3'-trifluoromethyl-biphenyl-3-yl)-4-methyl-pentanoic acid methyl ester

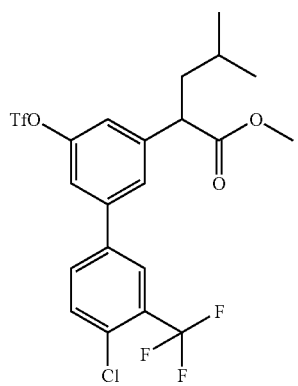

The title compound was prepared in 70% yield from 2-(3-benzyloxy-5-trifluoromethanesulfonyloxy-phenyl)-4-methyl-pent-4-enoic acid methyl ester (prepared in Example 1, step (d)) under the conditions described in Example 1, step (e-g)) using 4-chloro-5-trifluoromethylphenylboronic acid in step (e). RT=4.31 min b) 2-[4'-Chloro-5-(N-[3,5-bis-(trifluoromethyl)phenyl]-N-methylamino)-3'-trifluoromethyl-biphenyl-3-yl]-4-methyl-pentanoic acid The title product was prepared in 15% yield from 2-(4'-chloro-5-trifluoromethanesulfonyloxy-3'-trifluoromethyl-biphenyl-3-yl)-4-methyl-pentanoic acid methyl ester under the conditions described in Example 24, step (a-b). RT=4.53 min. Mass spectrum (ESI, m/z): 612, 614 (M+H).

EXAMPLE 28

2-[5-(3,4-Dihydro-2H-quinolin-1-yl)-4'-trifluoromethyl-biphenyl-3-yl]-4-methyl-pentanoic acid

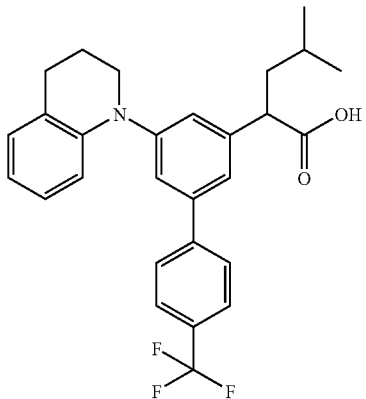

a) 2-[5-(3,4-Dihydro-2H-quinolin-1-yl)-4'-trifluoromethyl-biphenyl-3-yl]-4-methyl-pentanoic acid methyl ester

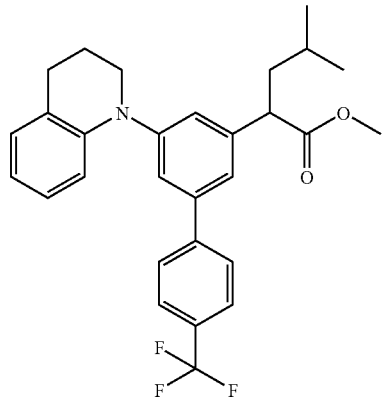

The title compound was prepared in 25% yield from 4-methyl-2-(5-trifluoromethanesulfonyloxy-4'-trifluoromethyl-biphenyl-3-yl)-pentanoic acid methyl ester and 1,2,3,4-tetrahydroquinoline under the conditions described in Example 24, steps (a).

b) 2-[5-(3,4-Dihydro-2H-quinolin-1-yl)-4'-trifluoromethyl-biphenyl-3-yl]-4-methyl-pentanoic acid The title compound was prepared in 69% yield from 2-[5-(3,4-dihydro-2H-quinolin-1-yl)-4'-trifluoromethyl-biphenyl-3-yl]-4-methyl-pentanoic acid methyl ester under the conditions described in Example 24, step (b).

$^1$H-NMR (400 MHz, CD$_3$Cl): δ 7.65 (s, 4H), 7.37 (d, 1H), 7.24 (s, 2H), 7.07 (d, 1H), 6.95 (t, 1H), 6.88 (d, 1H), 6.74 (t, 1H), 3.73-3.66 (m, 3H), 2.85 (t, 2H), 2.08-1.95 (m, 3H), 1.77-1.70 (m, 1H), 1.60-1.53 (m, 1H), 0.94 (d, 6H); RT=4.20 min.

EXAMPLE 29

2-{5-[1-(3,5-Difluoro-phenyl)-4-methyl-pentylamino]-4'-trifluoromethyl-biphenyl-3-yl}-4-methyl-pentanoic acid

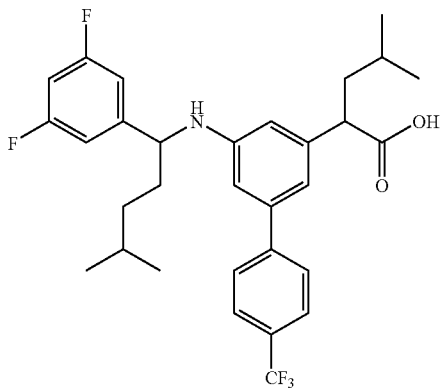

a) 3-methyl-1-butyl magnesium bromide

To a dry 100 ml three-neck flask equipped with a dry ice condenser and under N$_2$ was added Mg turning (1.5 g, 0.0625 mol), HgCl$_2$ (0.1 g), ether (60 ml) and 1-Br-3-methylbutane (8 g, 0.053 mol). The resulting mixture was stirred at room temperature 20 min and then heated to reflux for 30 min. The obtained Grignard reagent was used for the subsequent reaction.

b) 3,5-Difluoro-N-methoxy-N-methyl-benzamide

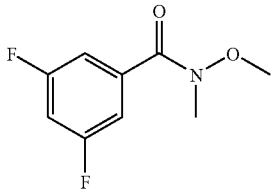

To an ice cooled mixture of 3,5 difluoro benzoic acid (2.0 g, 0.012 mol), 1-hydroxy-benzotriazole (HOBT, 2.5 g, 0.018 mol) and N,O-dimethylhydroxylamine HCl (2.35 g, 0.025 mol) in CH$_2$Cl$_2$(100 mL) was added triethylamine (5.0 mL, 0.036 mol) and followed by addition of 1,3-dimethylamino propyl-3-ethylcarbodiimide (EDC, 3.8 g, 0.019 mol). The mixture was allowed to warm to room temperature and continuously stir overnight. The reaction mixture was added EtOAc (300 mL) and then washed by diluted HCl solution, NaHCO$_3$ and NaCl solution. The organic layer was collected and dried with Mg$_2$SO$_4$ and evaporated. The crude product was purified by column (0-50% EtOAc/Heptane) to give the title compound, 2.6 gm colorless oil. (100%)

c) 1-(3,5-Difluoro-phenyl)-4-methyl-pentan-1-one

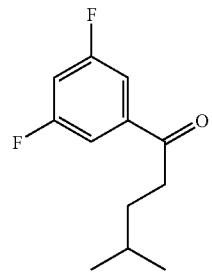

To a solution of compound 29 b (2.6 g, 0.012 mol) in THF (50 mL) at 0° C. with stirring was added the Grignard solution as prepared above (30 mL, 0.026 mol) dropwise. After the addition, the reaction solution was stirred at room temperature for 20 min and then EtOAc (100 mL) was added and then was basified with NaHCO$_3$. The EtOAc layer was collected and washed by NaCl aq. The solvent was then concentrated and the crude product was purified by column (0-30% EtOAc/heptane) to give the title compound, 2.16 gm colorless oil. (79%).

d) 1-(3,5-Difluoro-phenyl)-4-methyl-pentylamine

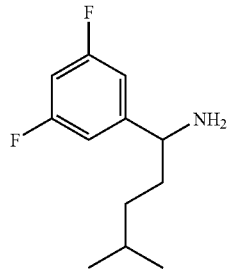

To a sodium ethoxide solution, prepared from sodium (0.26 g, 0.011 mol) in ethanol (10 mL), was added a solution of hydroxylamine hydrochloride (0.785 g, 0.011 mol) in water (5 mL). The resulting solution was stirred at room temperature for 30 min. The precipitate was filtered off and washed with alcohol (5 mL). To the combined filtrate was added compound 29 c (2.16 g, 0.01 mol) and heated for refluxing for 1 hour. The reaction mixture was diluted with EtOAc (100 mL) and then was washed by NaCl aq. The EtOAc layer was dried with Mg$_2$SO$_4$ and evaporated. The crude hydroxyl imine was then placed in a hydrogenation bottle with MeOH (30 mL), NH$_4$OH (1 mL) and Pd—C 10% (0.2 g) and subjected to hydrogenation under 5 psi for two hrs. The catalyst was filtered out and MeOH was removed by vacuum to give the title compound, 2.0 g oil. (88% yield at 95% purity).

MH$^+$ 214.2 e) 2-{5-[1-(3,5-Difluoro-phenyl)-4-methyl-pentylamino]-4'-trifluoromethyl-biphenyl-3-yl}-4-methyl-pentanoic acid ethyl ester

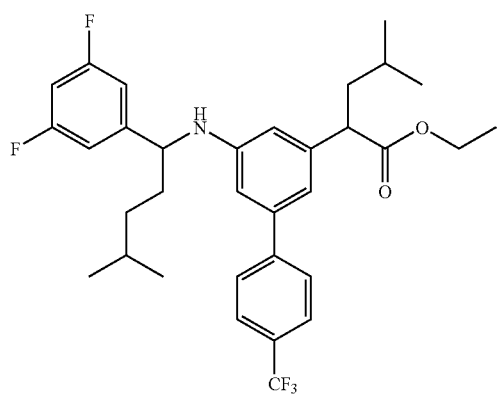

A solution of compound 29 d (0.5 g, 2 mmol), triflate from Example 1, step (g) (0.5 g, 1 mmol), Pd$_2$(dba)$_3$ (0.09 g), dppbiphenyl (0.03 g), potassium phosphate tribasic (0.25 g, 1.2 mmol), DME (10 mL) in a microwave reaction tube was subjected to microwave reaction (100° C., 20 min). The solvent was removed by vacuum and the crude product was purified by column to give the title compound, 0.35 gm oil (62%).
MH$^+$ 576.3 f) 2-{5-[1-(3,5-Difluoro-phenyl)-4-methyl-pentylamino]-4'-trifluoromethyl-biphenyl-3-yl}-4-methyl-pentanoic acid A solution of compound 29 e (0.08 g), 1N NaOH (1 mL) in THF/MeOH (10/10 mL) was stirred at room temperature for two days. EtOAc (50 mL) added. The organic layer was washed with citric acid aq., NaCl aq., dried with Mg$_2$SO$_4$ and evaporated. The crude product was purified by prep TLC (40% EtOAc/Heptane) to give the title compound, 0.012 g acid product (16%)
MH$^+$ 648.3
$^1$H NMR (300 MHz, CD$_3$OD): δ0.66 (m, 3H), δ0.74 (m, 3H), δ0.81 (m, 6H), δ1.2-1.8 (m, 8H), δ3.4 (m, 1H), δ4.5 (m, 1H), δ6.4 (m, 1H), δ6.7 (m, 2H), δ7.4 (s, 4H), δ7.7 (s, 1H), δ7.9 (s, 2H).

EXAMPLE 30

2-{5-[1-(3,5-Bis-trifluoromethyl-phenyl)-4-methyl-pentylamino]-4'-trifluoromethyl-biphenyl-3-yl}-4-methyl-pentanoic acid

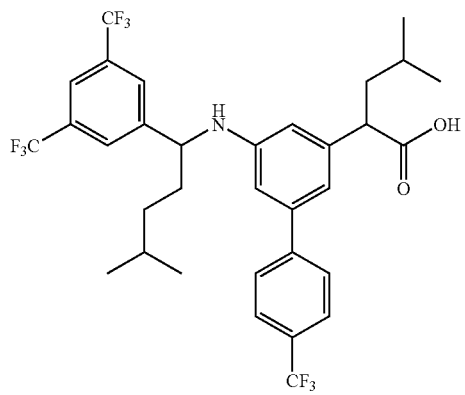

a) N-Methoxy-N-methyl-3,5-bis-trifluoromethyl-benzamide

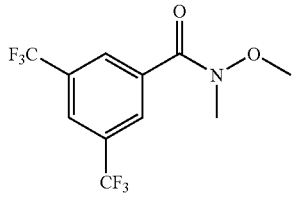

The title compound was prepared by the same procedure as the described in Example 29, step (b).

b) 1-(3,5-Bis-trifluoromethyl-phenyl)-4-methyl-pentan-1-one

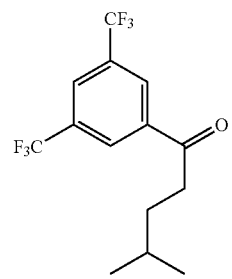

The title compound was prepared via the same procedure as the described in Example 29, step (c) starting with compound 30 a.

c) 1-(3,5-Bis-trifluoromethyl-phenyl)-4-methyl-pentylamine

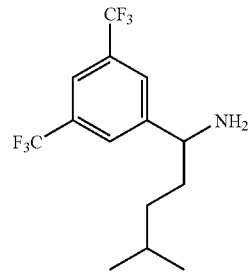

The title compound was prepared via the same procedure as the described in Example 29, step (d) starting with compound 30 b.
MH$^+$ 314.3 d) 2-{5-[1-(3,5-Bis-trifluoromethyl-phenyl)-4-methyl-pentylamino]-4'-trifluoromethyl-biphenyl-3-yl}-4-methyl-pentanoic acid ethyl ester

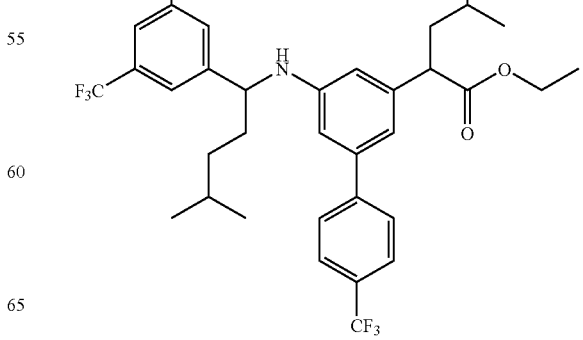

A solution of compound 30 c, as prepared above, (0.2 g, 0.64 mmol), triflate from Example 1, step (g) (0.11 g, 0.21 mmol), Pd$_2$(dba)$_3$ (0.03 g), dppbiphenyl (0.01 g), potassium phosphate tribasic (0.11 g, 0.5 mmol), DME (3 mL) in a microwave reaction tube was subjected to microwave reaction (100° C., 20 min). The solvent was removed by vacuum to give the title compound, 0.08 g crude product. (55%)
MH$^+$ 676.3 e) 2-{5-[1-(3,5-Bis-trifluoromethyl-phenyl)-4-methyl-pentylamino]-4'-trifluoromethyl-biphenyl-3-yl}-4-methyl-pentanoic acid A solution of compound 30 d, as prepared above (0.08 g), 1N NaOH (1 mL) in THF/MeOH (10/10 mL) was stirred at room temperature for two days. EtOAc (50 mL) added. The organic layer was washed by citric acid aq., NaCl aq., dried with Mg$_2$SO$_4$ and evaporated. The crude product was purified by prep TLC (40% EtOAc/Heptane) to give the title compound, 0.012 g (16%)
MH$^+$ 648.3
$^1$H NMR (300 MHz, CD$_3$OD): δ0.66 (m, 3H), δ0.74 (m, 3H), δ0.81 (m, 6H), δ1.2-1.8 (m, 8H), δ3.4 (m, 1H), δ4.5 (m, 1H), δ6.4 (m, 1H), δ6.7 (m, 2H), δ7.4 (s, 4H), δ7.7 (s, 1H), δ7.9 (s, 2H).

EXAMPLE 31

4-Methyl-2-{5-[4-methyl-1-(4-trifluoromethyl-phenyl)-pentylamino]-4'-trifluoromethyl-biphenyl-3-yl}-pentanoic acid

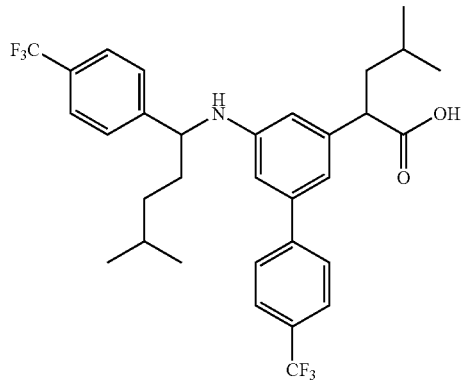

a)
N-Methoxy-N-methyl-4-trifluoromethyl-benzamide

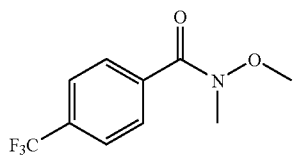

Following the procedure of Example 29, step (b), reaction of α,α,α-trifluoro-toluric acid with N,O-dimethylhydroxylamine HCl in present of HOBT, EDA, TEA in DCM followed the column purification gave the title compound; (96% yield) Calcd MW 233.19; Found MH$^+$ 234.1.

b) 4-Methyl-1-(4-trifluoromethyl-phenyl)-pentan-1-one

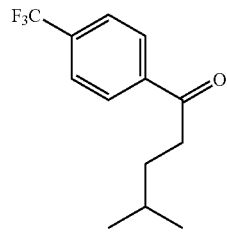

With the similar conditions of Example 29, steps (a) and (c), reaction of N-Methoxy-N-methyl-4-trifluoromethyl-benzamide, compound 31 a, with 3-methyl-1-butyl magnesium bromide, compound 29a, in THF gave the title compound in 77% yield; Calcd MW 244.26. Found MH$^+$ 245.2.

c)
4-Methyl-1-(4-trifluoromethyl-phenyl)-pentylamine

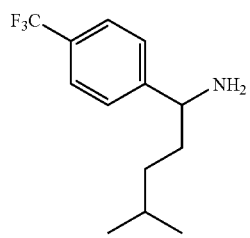

Following the procedure of Example 29, step (d), reaction of compound 32a as prepared above with hydroxylamine hydrochloride followed by hydrogenation gave the title compound; The crude product used as it. Calcd MW 245.29. Found MH$^+$ 246.1.

d) 4-Methyl-2-{5-[4-methyl-1-(4-trifluoromethyl-phenyl)-pentylamino]-4'-trifluoromethyl-biphenyl-3-yl}-pentanoic acid ethyl ester

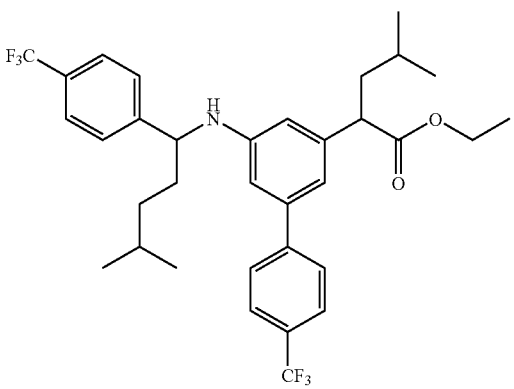

Following the procedure of Example 30, step (d)], reaction of compound 31c as prepared above with triflate compound 1g gave the title compound; Calcd MW 607.69. Found MH$^+$ 608.3.

e) 4-Methyl-2-{5-[4-methyl-1-(4-trifluoromethyl-phenyl)-pentylamino]-4'-trifluoromethyl-biphenyl-3-yl}-pentanoic acid Following the procedure of Example 29, step (f), hydrolysis of compound 32c as prepared above gave the title compound in 47% yield; Calcd MW 579.62. Found MH+ 580.3.
¹H NMR (300 MHz, CD₃OD): δ0.65-0.82 (m, 12H), δ1.08-1.86 (m, 8H), δ3.36-3.43 (m, 1H), δ4.32-4.37 (m, 1H), δ6.41 (s, 1H), δ6.5-6.66 (m, 2H), δ7.48-7.54 (m, 8H).

EXAMPLE 32

5-[4-Methyl-1-(4-trifluoromethyl-phenyl)-pentylamino]-4'-trifluoromethyl-biphenyl-3-yl}-acetic acid

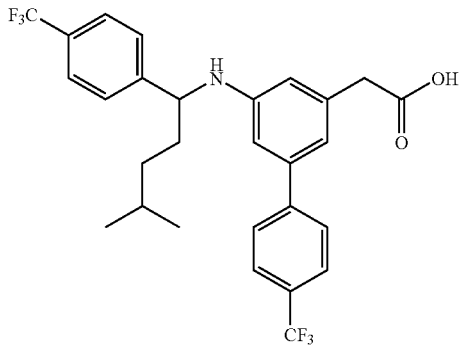

a) (5-Trifluoromethanesulfonyloxy-4'-trifluoromethyl-biphenyl-3-yl)-acetic acid ethyl ester

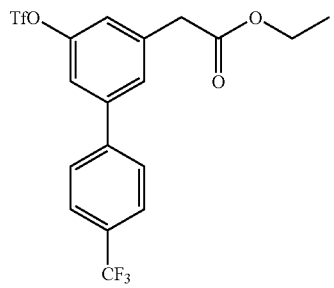

Using the procedure described for the preparation of compound 1f, compound 1d was hydrogenated and then converted to triflate as described in Example 1, steps (f) and (g).

b) {5-[4-Methyl-1-(4-trifluoromethyl-phenyl)-pentylamino]-4'-trifluoromethyl-biphenyl-3-yl}-acetic acid ethyl ester

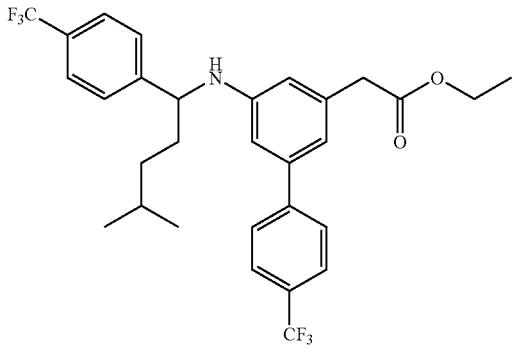

Following the procedure of Example 30, step (d), reaction of 4-Methyl-1-(4-trifluoromethyl-phenyl)-pentylamine, compound 31b, and compound 32a gave the title compound in 69% yield; Calcd MW 551.58. Found MH+ 552.2.

c) 5-[4-Methyl-1-(4-trifluoromethyl-phenyl)-pentylamino]-4'-trifluoromethyl-biphenyl-3-yl}-acetic acid Following the procedure of Example 29, step (f), hydrolysis of compound 32b as prepared above gave the title compound in 55% yield; Calcd MW 523.51. Found MH+ 524.3.
¹H NMR (300 MHz, CD₃OD): δ0.65-0.79 (m, 6H), δ1.1 (m, 1H), δ1.14-1.26 (m, 1H), δ1.43-1.50 (m, 1H), δ1.63-1.78 (m, 2H), δ3.24 (m, 2H), δ4.3 (t, 1H, J=6.83 Hz), δ6.45 (s, 1H), δ6.57 (s, 1H), δ6.65 (s, 1H), δ7.48 (m, 8H).

EXAMPLE 33

5-[1-(3,5-Difluoro-phenyl)-4-methyl-pentylamino]-4'-trifluoromethyl-biphenyl-3-yl}-acetic acid

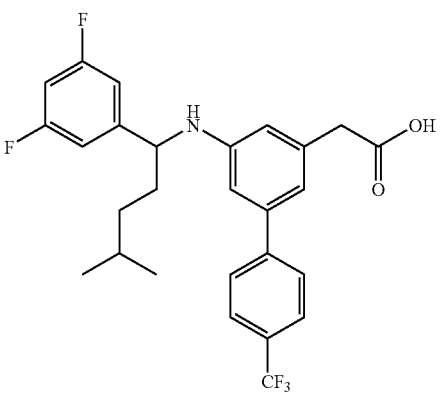

a) {5-[1-(3,5-Difluoro-phenyl)-4-methyl-pentylamino]-4'-trifluoromethyl-biphenyl-3-yl}-acetic acid ethyl ester

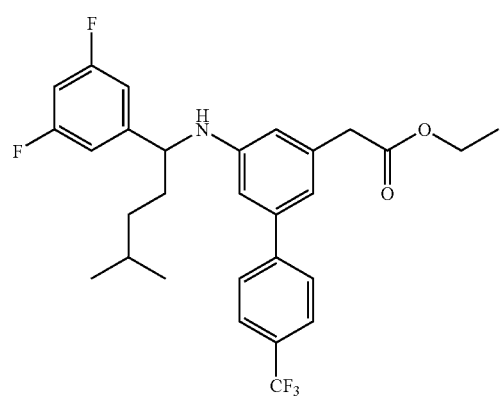

Following the procedure of Example 29, step (e), reaction of 1-(3,5-Difluoro-phenyl)-4-methyl-pentylamine with triflate compound 32a gave the title compound in 45% yield; Calcd MW 519.56. Found MH+ 520.3.

b) {5-[1-(3,5-Difluoro-phenyl)-4-methyl-pentylamino]-4'-trifluoromethyl-biphenyl-3-yl}-acetic acid Following the procedure of Example 29, step (f), hydrolysis of compound 33a gave the title compound in 25% yield;

Calcd MW 491.49. Found MH⁺ 492.3. ¹H NMR (300 MHz, CD₃OD): δ0.81 (t, 6H, J=6.23 Hz), δ1.07-1.79 (m, 5H), δ3.4 (s, 2H), δ4.3 (t, 1H, J=6.72 Hz), δ6.44 (s, 1H), δ6.6 (s, 1H), δ6.64 (t, 1H, J=2.2 Hz), δ6.68 (s, 1H), δ6.9 (d, 2H, J=6.46 Hz), δ7.56 (m, 4H).

EXAMPLE 34

4-Methyl-2-[5-(1,2,3,4-tetrahydro-naphthalen-1-ylamino)-4'-trifluoromethyl-biphenyl-3-yl]-pentanoic acid

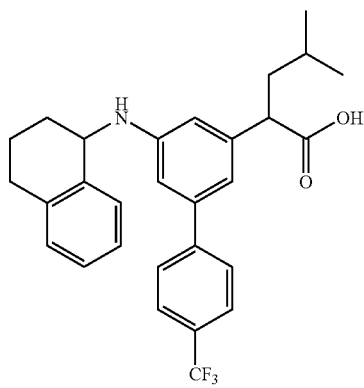

a) -Methyl-2-[5-(1,2,3,4-tetrahydro-naphthalen-1-ylamino)-4'-trifluoromethyl-biphenyl-3-yl]-pentanoic acid ethyl ester

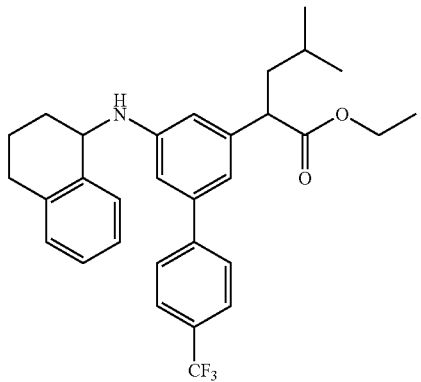

Following the procedure of Example 29, step (e), reaction of 1,2,3,4-tetrahydro-1-phthyl amine with triflate compound 1g gave the title compound; Calcd MW 509.62. Found MH 510.4.

b) 4-Methyl-2-[5-(1,2,3,4-tetrahydro-naphthalen-1-ylamino)-4'-trifluoromethyl-biphenyl-3-yl]-pentanoic acid Following the procedure of Example 29, step (f), hydrolysis of compound 34a as prepared above gave the title compound; Calcd MW 481.55. Found MH⁺ 482.3.

¹H NMR (300 MHz, CD₃OD): δ0.85 (d, 6H, J=6.16 Hz), δ1.19 (m, 2H), δ1.49 (m, 2H), δ1.7-1.88 (m, 3H), δ2.71 (m, 2H), δ3.46 (m, 1H), δ4.61 (m, 1H), δ6.70 (m, 2H), δ6.88 (s, 1H), δ7.0 (m, 3H,), δ7.23 (m, 1H), δ7.55 (d, 2H, J=8.4 Hz), δ7.68 (d, 2H, J=8.0 Hz).

EXAMPLE 35

4-Methyl-2-[5-(5,6,7,8-tetrahydro-isoquinolin-5-ylamino)-4'-trifluoromethyl-biphenyl-3-yl]-pentanoic acid

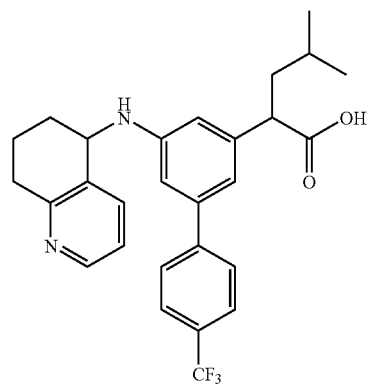

a) 4-Methyl-2-[5-(5,6,7,8-tetrahydro-isoquinolin-5-ylamino)-4'-trifluoromethyl-biphenyl-3-yl]-pentanoic acid ethyl ester

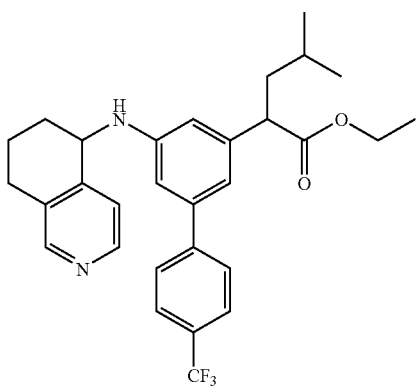

Following the procedure of Example 29, step (e), reaction of 5-amino-5,6,7,8-1,2,3,4-tetrahydro-quinoline with compound 1g gave the title compound; Calcd MW 510.60. Found MH⁺ 511.4.

b) 4-Methyl-2-[5-(5,6,7,8-tetrahydro-isoquinolin-5-ylamino)-4'-trifluoromethyl-biphenyl-3-yl]-pentanoic acid Following the procedure of Example 29, step (f), hydrolysis of compound 35a as prepared above gave the title compound; Calcd MW 482.54. Found MH⁺ 483.2

¹H NMR (300 MHz, CD₃OD): δ0.85 (d, 6H, J=6.07 Hz), δ1.15 (m, 2H), δ1.49 (m, 2H), δ1.8-1.95 (m, 3H), δ2.52-2.83 (m, 2H), δ3.45 (m, 1H), δ4.71 (m, 1H), δ6.71 (d, 2H, J=4.2 Hz), δ6.89 (s, 1H), δ7.13 (d, 1H, J=4.6 Hz), δ7.58 (d, 2H, J=8.5 Hz), δ7.68 (d, 2H, J=8.3 Hz). δ7.78 (d, 1H, J=7.6 Hz), δ8.21 (d, 1H, J=5.02 Hz).

EXAMPLE 36

[5-(5,6,7,8-Tetrahydro-isoquinolin-5-ylamino)-4'-trifluoromethyl-biphenyl-3-yl]-acetic acid

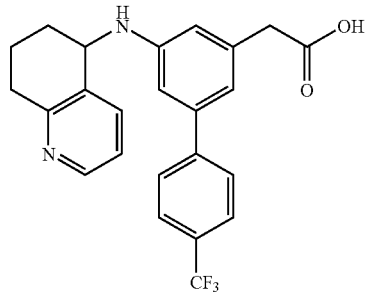

a) [5-(5,6,7,8-Tetrahydro-isoquinolin-5-ylamino)-4'-trifluoromethyl-biphenyl-3-yl]-acetic acid ethyl ester

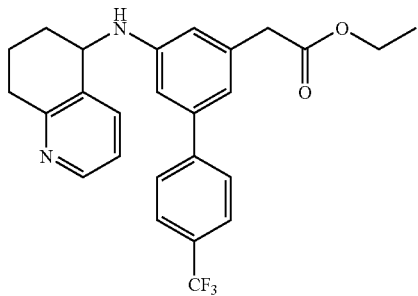

Following the procedure of Example 29, step (e), reaction of 5-amino-5,6,7,8-1,2,3,4-tetrahydro-quinoline with triflate compound 32a gave the title compound.

b) [5-(5,6,7,8-Tetrahydro-isoquinolin-5-ylamino)-4'-trifluoromethyl-biphenyl-3-yl]-acetic acid Following the procedure of Example 29, step (f), hydrolysis of compound 36a as prepared above gave the title compound; $^1$H NMR (300 MHz, CD$_3$OD): δ1.7-1.88 (m, 3H), δ2.35-2.78 (m, 3H), δ3.36 (s, 2H), δ4.60 (m, 1H), δ6.68 (d, 2H, J=7.2 Hz), δ6.81 (s, 1H), δ6.98-7.05 (m, 2H), δ7.2 (d, 1H, J=2.2 Hz), δ7.5 (d, 2H, J=8.23 Hz). δ7.68 (d, 2H, J=8.23 Hz).

EXAMPLE 37

2-[5-(4-tert-Butyl-benzylamino)-4'-trifluoromethyl-biphenyl-3-yl]-4-methyl-pentanoic acid

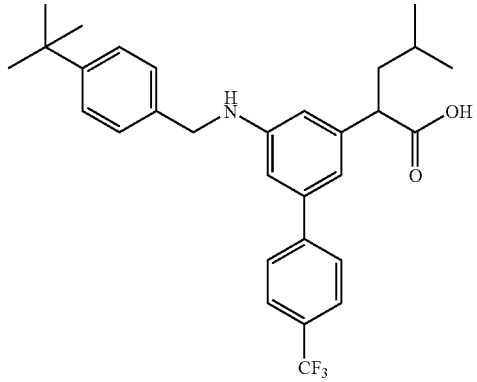

a) 2-[5-(4-tert-Butyl-benzylamino)-4'-trifluoromethyl-biphenyl-3-yl]-4-methyl-pentanoic acid ethyl ester

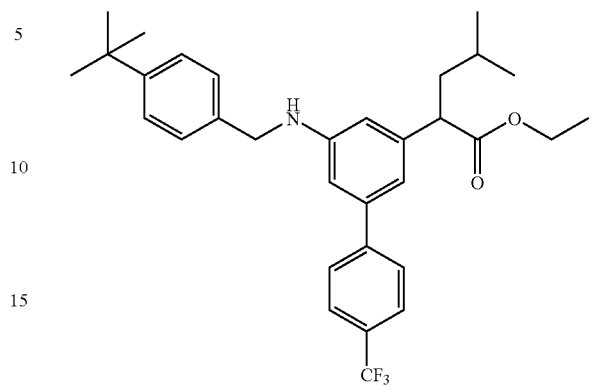

Following the procedure of Example 29, step (e), reaction of 4-tButyl-benzylamine with triflate compound 1g, gave the title compound; Calcd MW 525.66. Found MH$^+$ 526.3.

b) 2-[5-(4-tert-Butyl-benzylamino)-4'-trifluoromethyl-biphenyl-3-yl]-4-methyl-pentanoic acid Following the procedure of Example 29, step (f), hydrolysis of compound 37 a as prepared above gave the title compound; Calcd MW 497.59. Found MH$^+$ 498.3.

$^1$H NMR (300 MHz, CD$_3$OD): δ0.76-0.8 (m, 15H), δ1.38-1.49 (m, 2H), δ1.79 (m, 1H), δ3.21 (m, 1H), δ4.24 (s, 2H), δ6.62 (m, 1H), δ6.65 (m, 1H), δ6.86 (m, 1H), δ7.3 (m, 4H,), δ7.5 (d, 2H, J=8.25 Hz). δ7.62 (d, 2H, J=8.25 Hz).

EXAMPLE 38

4-Methyl-2-{5-[4-methyl-1-(3,4,5-trifluoro-phenyl)-pentylamino]-4'-trifluoromethyl-biphenyl-3-yl}-pentanoic acid

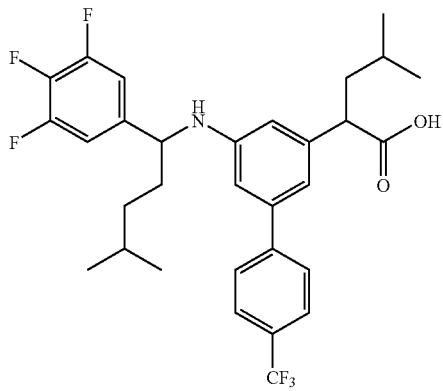

a) 3,4,5-Trifluoro-N-methoxy-N-methyl-benzamide

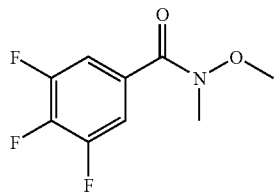

Following the procedure of Example 29, step (b), reaction of 3,4,5-trifluoro-benzoic acid with N,O-dimethylhydroxylamine HCl in present of HOBT, EDA, TEA in DCM followed the column purification gave the title compound; Calcd MW 219.16. Found MH+ 220.1.

b) 4-Methyl-1-(3,4,5-trifluoro-phenyl)-pentyl-propan-1-one

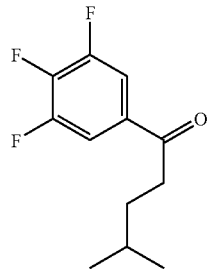

Following the procedure of Example 29, step (c), reaction of compound 38a as prepared above with 3-methyl-1-butyl magnesium bromide from Example 29, step (a) in THF followed by column gave the title compound (81% yield).

c) 4-Methyl-1-(3,4,5-trifluoro-phenyl)-pentylamine

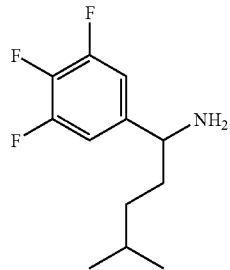

Following the procedure of Example 29, reaction of compound 38 b with hydroxylamine hydrochloride followed by hydrogenation gave the title compound; (35% yield) Calcd MW 231.26. Found MH+ 232.2.

d) 4-Methyl-2-{5-[4-methyl-1-(3,4,5-trifluoro-phenyl)-pentylamino]-4'-trifluoromethyl-biphenyl-3-yl}-pentanoic acid ethyl ester

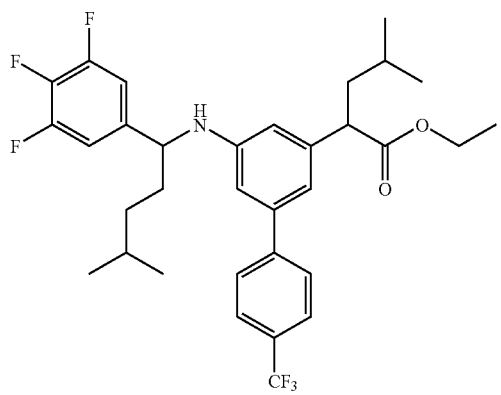

Following the procedure of Example 29, step (e), reaction of compound 38c as prepared above with triflate compound 1g gave the title compound; Calcd MW 593.66. Found MH+ 594.3 d) 4-Methyl-2-{5-[4-methyl-1-(3,4,5-trifluoro-phenyl)-pentylamino]-4'-trifluoromethyl-biphenyl-3-yl}-pentanoic acid Following the procedure of Example 29, step (f), hydrolysis of compound 38d gave the title compound; Calcd MW 565.59. Found MH+ 566.4; $^1$H NMR (300 MHz, CD$_3$OD): δ0.71-0.83 (m, 12H), δ1.26-1.33 (m, 2H), δ1.40-1.48 (m, 2H), δ1.56-1.64 (m, 4H), δ3.31-3.36 (m, 1H), δ4.3 (m, 1H), δ6.48-6.57 (m, 2H), δ6.8 (d, 1H, J=16 Hz), δ7.04-7.09 (m, 2H), δ7.50 (m, 4H).

EXAMPLE 39

2-{5-[(4-tert-Butyl-benzyl)-(3-methyl-butyl)-amino]-4'-trifluoromethyl-biphenyl-3-yl}-4-methyl-pentanoic acid

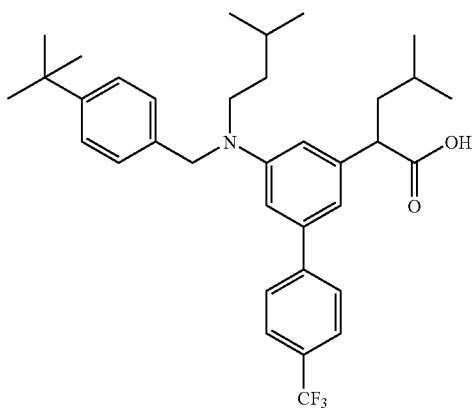

a) 2-{5-[(4-tert-Butyl-benzyl)-(3-methyl-butyl)-amino]-4'-trifluoromethyl-biphenyl-3-yl}-4-methyl-pentanoic acid ethyl ester

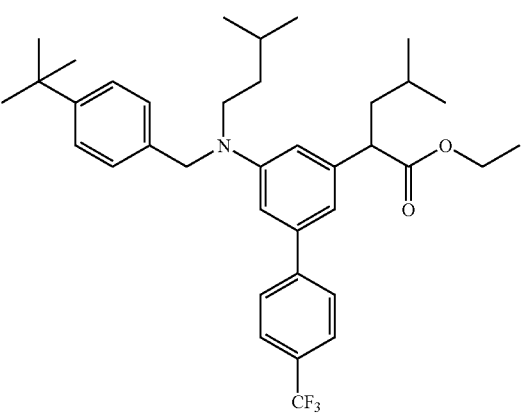

A solution of 2-[5-(4-tert-Butyl-benzylamino)-4'-trifluoromethyl-biphenyl-3-yl]-4-methyl-pentanoic acid ethyl ester, compound 37a, (0.06 g, 0.11 mmol), isovaleraldehyde (0.36 mL, 3.3 mmol), AcOH (0.01 mL) in DCM (10 mL) was stirred at room temperature overnight. NaCNBH$_4$ (0.01 g, 0.16 mmol) added and resulting solution was stirred 30 min.

The crude product was purified by TLC plate to give the title compound at 50% yield. Calcd MW 595.8. Found MH+ 596.4.

b) 2-{5-[(4-tert-Butyl-benzyl)-(3-methyl-butyl)-amino]-4'-trifluoromethyl-biphenyl-3-yl}-4-methyl-pentanoic acid Following the procedure of Example 29, step (f), hydrolysis of compound 39a as prepared above gave the title compound; Calcd MW 567.72. Found MH+ 568.5.

$^1$H NMR (300 MHz, CDCl$_3$): δ0.77-0.81 (m, 6H), α0.81-0.94 (m, 6H), δ1.18 (m, 1H), δ1.23 (s, 9H), δ1.41-1.62 (m, 6H), δ1.76-1.83 (m, 1H), δ3.37 (m, 2H), δ3.56 (m, 1H), δ6.58 (s, 1H), δ6.7 (s, 1H), δ6.73 (s, 1H), δ7.1 (d, 2H, J=8.2 Hz), δ7.2 (d, 2H, J=8.2 Hz), δ7.50 (m, 4H).

EXAMPLE 40

2-{5-[(3,5-Difluoro-benzyl)-(3-methyl-butyl)-amino]-4'-trifluoromethyl-biphenyl-3-yl}-4-methyl-pentanoic acid

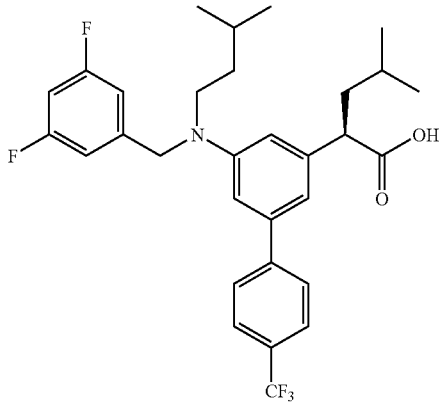

a) 2-(5-Amino-4'-trifluoromethyl-biphenyl-3-yl)-4-methyl-pentanoic acid methyl ester

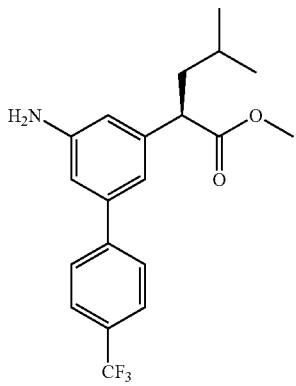

A solution of benzophenone imine (2.9 mL, 16 mmol), triflate compound 1g (R isomer, 4 g, 8 mmol), Pd$_2$(dba)$_3$ (0.73 g), dppbiphenyl (0.25 g), potassium phosphate tribasic (2 g, 9.4 mmol), DME (20 mL) was equally placed into four microwave reaction tubes. The reaction mixtures were heated in a microwave reactor (100° C., 20 min). LC/MS of the reaction mixture indicated a mixture of 1:1 of the aniline product and imine intermediate. The solid was removed and the filtrate was concentrated on a rotator evaporator to give a residue. The crude was then dissolved in MeOH and then was added NaOAc (2 g) and NH$_2$OH—HCl (1 g) and the resulting mixture was stirred at room temperature for 20 min. The imine intermediate was converted to the product as expected. The solvent was removed and the residue was re-dissolved in EtOAc and the solution was washed with water and dried over Na2SO4. The crude product was purified by column chromatography (0-30% EtOAc/Heptane) to give the title compound, 2.5 g brown oil. (42% yield), Calcd MW 365.4, MH+ 366.1 b) 2-[5-(3,5-Difluoro-benzylamino)-4'-trifluoromethyl-biphenyl-3-yl]-4-methyl-pentanoic acid methyl ester

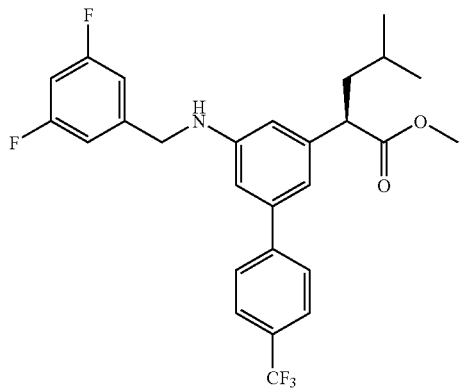

A solution of 3,5-difluor-benzaldehyde (0.09 g, 0.6 mmol), compound 40a, as prepared above (0.23 g, 0.6 mmol) in MeOH (10 mL) was stirred at room temperature for one hour and then NaBH$_4$ (0.05 g, 13 mmol) was added. The solution was stirred another 30 min. After removing of the solvent, the crude oil was purified by column chromatography (0-30% EtOAc/heptane) to give the title compound, 0.15 g colorless oil. (50%). Calcd. MW 491.51. Found MH+ 492.1.

c) 2-{5-[(3,5-Difluoro-benzyl)-(3-methyl-butyl)-amino]-4'-trifluoromethyl-biphenyl-3-yl}-4-methyl-pentanoic acid methyl ester

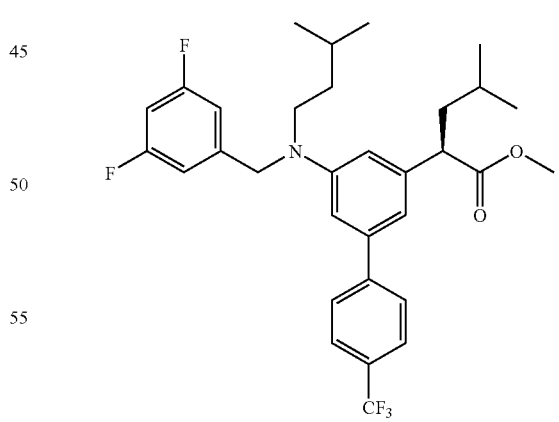

A solution of compound 40b, as prepared above (0.08 g, 0.16 mmol), isovaleraldehyde (0.17 mL, 1.6 mmol) and AcOH (one drop) in DCM (10 mL) was stirred at room temperature overnight. NaBH(OAc)$_3$ (0.07 g, 0.33 mmol) added and the solution was stirred another 30 min. The solution was added with EtOAc (50 mL), washed by NaOH (1N) solution and saturated aq. NaCl. The organic layer was dried with Mg₂SO₄ and evaporated. The crude was purified by column chromatography to give the title compound, 0.07 (76%) Calcd. MW 561.64. Found MH⁺ 562.3.

d) 2-{5-[(3,5-Difluoro-benzyl)-(3-methyl-butyl)-amino]-4'-trifluoromethyl-biphenyl-3-yl}-4-methyl-pentanoic acid A solution of compound 40c (0.07 g) in MeOH/THF/NaOH (1N) (5 mL/5 mL/0.5 mL) was stirred overnight. The reaction solution was concentrate and the residue was purified by Gilson reverse phase HPLC purification. The obtained TFA salt was then converted to Na salt to the title compound, 40 mg (56%). Calcd. MW 547.61, MH⁺ 548.4.
¹H NMR (300 MHz, CD₃OD): δ0.85 (dd, J=6.45 Hz, J=1.12 Hz, 6H), δ0.99 (d, 6H, J=6.3 Hz), δ1.5-1.8 (m, 6H), δ3.55 (m, 3H), δ4.6 (s, 2H), δ6.75 (m, 3H), δ6.88 (d, 2H, J=6.5 Hz), δ7.0 (s, 1H), 67.5 (m, 4H).

EXAMPLE 41

4-Methyl-2-[5-(4-trifluoromethoxy-benzylamino)-4'-trifluoromethyl-biphenyl-3-yl]-pentanoic acid

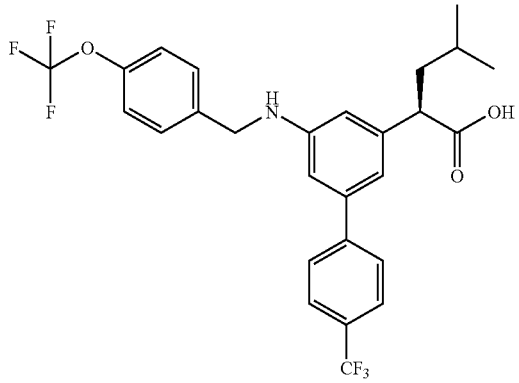

a) 4-Methyl-2-[5-(4-trifluoromethoxy-benzylamino)-4'-trifluoromethyl-biphenyl-3-yl]-pentanoic acid methyl ester

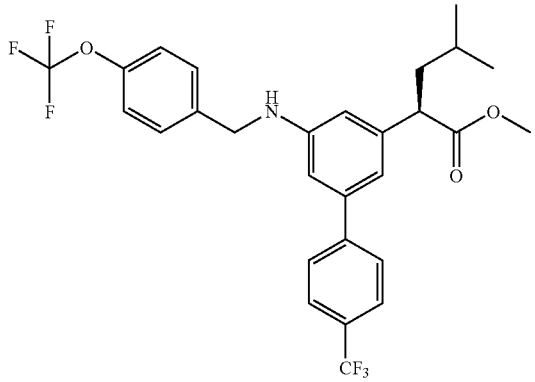

Following the procedure of Example 40, steps (a) and (b), reaction of 2-(5-Amino-4'-trifluoromethyl-biphenyl-3-yl)-4-methyl-pentanoic acid methyl ester, compound 40a, with 4-trifluoromethoxy benzaldehyde gave the title compound in 44% yield; Calcd MW 539.52. Found MH⁺ 540.3.

b) 4-Methyl-2-[5-(4-trifluoromethoxy-benzylamino)-4'-trifluoromethyl-biphenyl-3-yl]-pentanoic acid Following the procedure of Example 29, step (f), hydrolysis of compound 41a as prepared above gave the title compound; Calcd MW 525.5. Found MH⁺ 526.2.
¹H NMR (300 MHz, CDCl₃): δ0.76-0.79 (m, 6H), δ1.33-1.52 (m, 2H), δ1.71-1.81 (m, 1H), δ3.44 (t, 1H, J=7.4 Hz), δ4.31 (s, 2H), δ6.57 (s, 1H), δ6.64 (s, 1H), δ6.79 (s, 1H), δ7.1 (d, 2H, J=8.25 Hz), δ7.37 (d, 2H, J=8.5 Hz), δ7.57 (m, 4H).

EXAMPLE 43

(R) 4-Methyl-2-{5-[(3-methyl-butyl)-(4-trifluoromethoxy-benzyl)-amino]-4'-trifluoromethyl-biphenyl-3-yl}-pentanoic acid

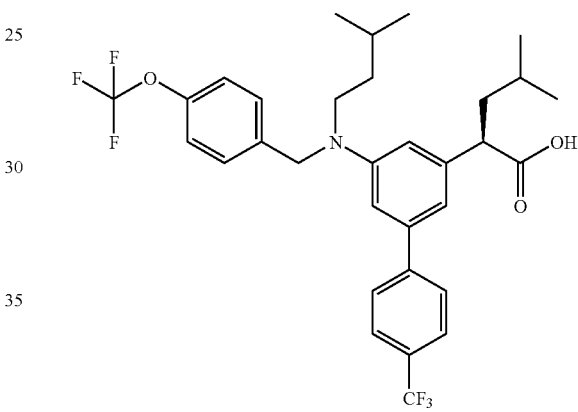

a) (R) 4-Methyl-2-{5-[(3-methyl-butyl)-(4-trifluoromethoxy-benzyl)-amino]-4'-trifluoromethyl-biphenyl-3-yl}-pentanoic acid methyl ester

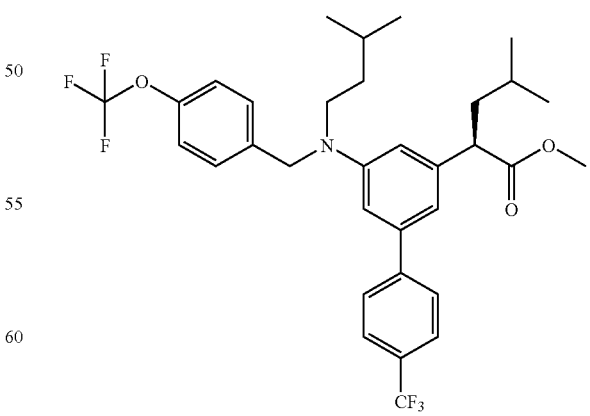

Following the procedure of Example 39, step (a) reaction of compound 41a with isovaleraldehyde gave the title compound; Calcd MW 609.66. Found MH⁺ 610.3.

b) -Methyl-2-{5-[(3-methyl-butyl)-(4-trifluoromethoxy-benzyl)-amino]-4'-trifluoromethyl-biphenyl-3-yl}-pentanoic acid Following the procedure of Example 29, step (f), hydrolysis of compound 42a as prepared above gave the title compound; Calcd MW 595.63. Found MH+ 596.4.

$^1$H NMR (300 MHz, CDCl$_3$): δ0.86 (dd, 6H, J=1 Hz, J=6.28 Hz), 0.98 (d, 6H, J=6.28 Hz), δ1.5-1.7 (m, 6H), δ3.5 (m, 3H), δ4.63 (s, 2H), δ6.74 (s, 1H), δ6.75 (s, 1H), δ6.91 (s, 1H), δ7.2 (d, 2H, J=8.02 Hz), δ7.36 (d, 2H, J=8.6 Hz), δ7.65 (s, 4H).

EXAMPLE 43

(R) 2-[5-(3,5-Difluoro-benzylamino)-4'-trifluoromethyl-biphenyl-3-yl]-4-methyl-pentanoic acid

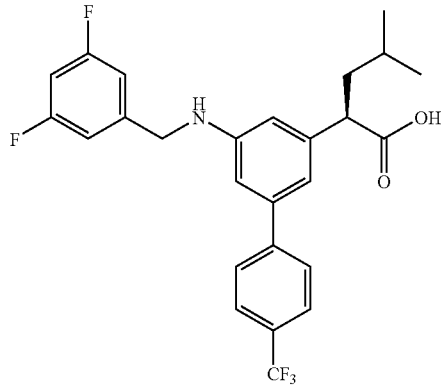

Following the procedure of Example 29, step (f), hydrolysis of 2-[5-(3,5-Difluoro-benzylamino)-4'-trifluoromethyl-biphenyl-3-yl]-4-methyl-pentanoic acid methyl ester, compound 40b, gave the title compound; Calcd MW 477.47. Found MH+ 478.2.

$^1$H NMR (300 MHz, CDCl$_3$): δ0.86-0.89 (m, 6H), δ1.50 (m, 1H), δ1.6 (m, 1H), δ1.83 (m, 1H), δ3.53 (t, 1H, J=7.6 Hz), δ4.41 (s, 2H), δ6.6 (s, 1H), δ6.7-6.9 (m, 2H), δ6.92 (s, 1H), δ7.0 (m, 2H), δ7.67 (m, 4H).

EXAMPLE 44

(R) 4-Methyl-2-[4'-trifluoromethyl-5-(4-trifluoromethyl-benzylamino)-biphenyl-3-yl]-pentanoic acid

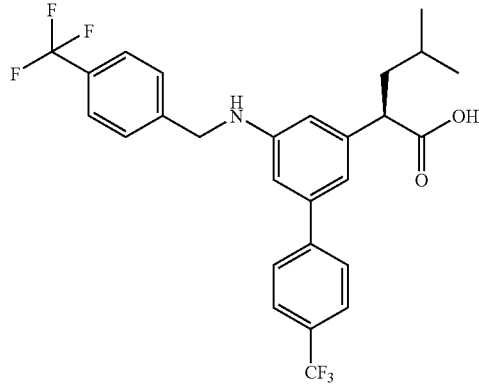

a) (R) 4-Methyl-2-[4'-trifluoromethyl-5-(4-trifluoromethyl-benzylamino)-biphenyl-3-yl]-pentanoic acid ethyl ester

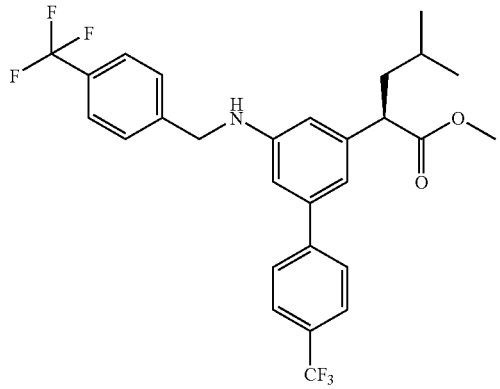

Following the procedure of Example 40, steps (a) and (b), reaction of 2-(5-Amino-4'-trifluoromethyl-biphenyl-3-yl)-4-methyl-pentanoic acid methyl ester, compound 40a, with ααα-trifluoro-p-tolualdehyde gave the title compound in 50% yield; Calcd MW 523.52. Found MH+ 524.3.

b) (R) 4-Methyl-2-[4'-trifluoromethyl-5-(4-trifluoromethyl-benzylamino)-biphenyl-3-yl]-pentanoic acid Following the procedure of Example 29, step (f), hydrolysis of compound 44a as prepared above gave the title compound; Calcd. MW 509.48. Found MH+ 510.3.

$^1$H NMR (300 MHz, CDCl$_3$): δ0.84 (m, 6H), δ1.4-1.59 (m, 1H), δ1.79-1.89 (m, 1H), δ3.5 (t, 1H, J=7.6 Hz), δ4.48 (s, 2H), δ6.7 (s, 1H), δ6.73 (s, 1H), δ6.93 (s, 1H), δ7.59 (s, 4H), δ7.62-7.7 (m, 4H).

EXAMPLE 45

4-Methyl-2-{5-[(3-methyl-butyl)-(4-trifluoromethyl-benzyl)-amino]-4'-trifluoromethyl-biphenyl-3-yl}-pentanoic acid

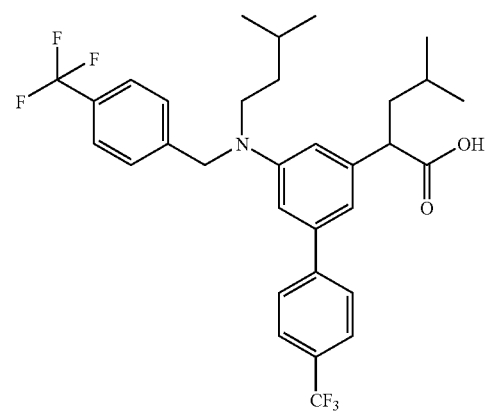

a) 4-Methyl-2-{5-[(3-methyl-butyl)-(4-trifluoromethyl-benzyl)-amino]-4'-trifluoromethyl-biphenyl-3-yl}-pentanoic acid methyl ester

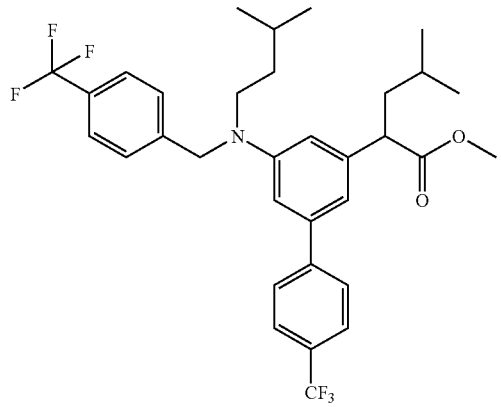

Following the procedure of Example 39, step (a), reaction of 4-Methyl-2-[4'-trifluoromethyl-5-(4-trifluoromethyl-benzylamino)-biphenyl-3-yl]-pentanoic acid methyl ester, compound 44a with isovaleraldehyde gave the title compound; Calcd.MW 593.66. Found MH+ 594.3.

b) 4-Methyl-2-{5-[(3-methyl-butyl)-(4-trifluoromethyl-benzyl)-amino]-4'-trifluoromethyl-biphenyl-3-yl}-pentanoic acid Following the procedure of Example 29, step (f), hydrolysis of compound 45a as prepared above gave the title compound; Calcd.MW 579.26. Found MH+ 580.3.
¹H NMR (300 MHz, CDCl₃): δ0.82 (m, 6H), δ0.96 (d, 6H, J=6.6 Hz), δ1.21-1.81 (m, 5H), δ3.5 (m, 4H), δ4.69 (s, 2H), δ6.73 (s, 1H), δ6.78 (s, 1H), δ6.99 (s, 1H), δ7.28 (d, 2H, J=8.14 Hz), δ7.58 (d, 2H, J=8.2 Hz), δ7.63-7.69 (m, 4H).

EXAMPLE 46

(R) 2-[5-(3,5-Bis-trifluoromethyl-benzylamino)-4'-trifluoromethyl-biphenyl-3-yl]-4-methyl-pentanoic acid

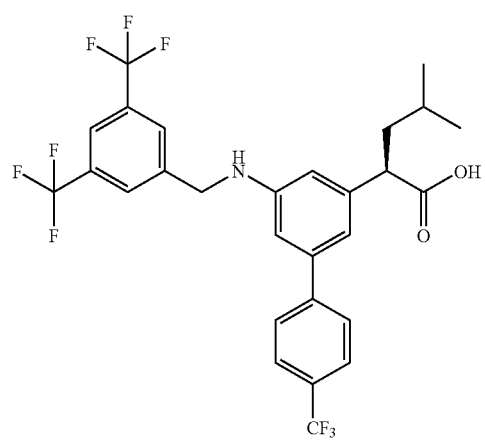

a) (R) 2-[5-(3,5-Bis-trifluoromethyl-benzylamino)-4'-trifluoromethyl-biphenyl-3-yl]-4-methyl-pentanoic acid methyl ester

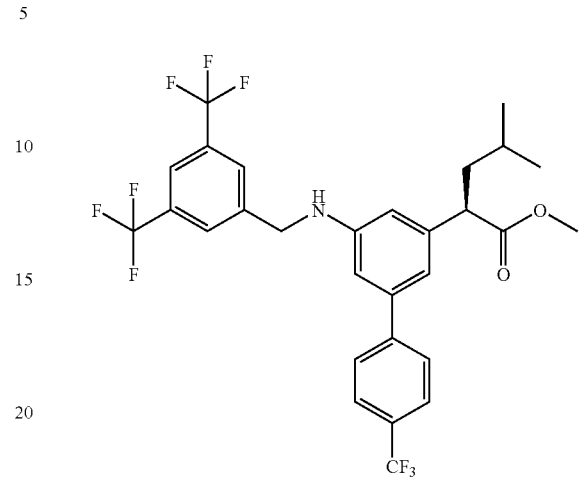

Following the procedure of Example 40, step (b), reaction of 2-(5-Amino-4'-trifluoromethyl-biphenyl-3-yl)-4-methyl-pentanoic acid methyl ester, compound 40a, with 3,5-bis(trifluoromethyl)benzaldehyde gave the title compound in 47% yield; Calcd.MW 591.52. Found MH+ 592.3.

b) 2-[5-(3,5-Bis-trifluoromethyl-benzylamino)-4'-trifluoromethyl-biphenyl-3-yl]-4-methyl-pentanoic acid Following the procedure of Example 29, step (f), hydrolysis of compound 46a as prepared above gave the title compound; Calcd. MW 577.48. Found MH+ 578.1.
¹H NMR (300 MHz, CD₃OD): δ0.84 (m, 6H), δ1.44 (m, 1H), δ1.57 (m, 1H), δ1.81 (m, 1H), δ3.52 (t, 1H, J=7.64 Hz), δ4.57 (s, 2H), δ6.65 (d, 1H, J=1.4 Hz), δ6.76 (t, 1H, J=1.8 Hz), δ6.94 (s, 1H), δ7.68 (m, 4H), δ7.81 (s, 1H), δ8.0 (s, 2H).

EXAMPLE 47

(R) 2-[5-(4-Cyano-benzylamino)-4'-trifluoromethyl-biphenyl-3-yl]-4-methyl-pentanoic acid

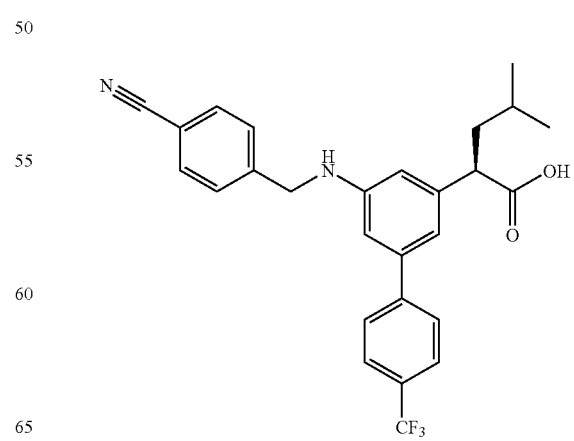

a) (R) 2-[5-(4-Cyano-benzylamino)-4'-trifluoromethyl-biphenyl-3-yl]-4-methyl-pentanoic acid methyl ester

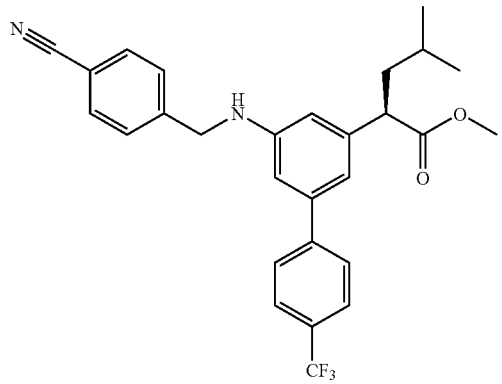

Following the procedure of Example 40, step (b), reaction of 2-(5-Amino-4'-trifluoromethyl-biphenyl-3-yl)-4-methyl-pentanoic acid methyl ester, compound 40a, with 4-cyanobenzaldehyde gave the title compound in 65% yield; Calcd. MW 480.53. Found MH⁺ 481.4.

b) (R) 2-[5-(4-Cyano-benzylamino)-4'-trifluoromethyl-biphenyl-3-yl]-4-methyl-pentanoic acid Following the procedure of Example 29, step (f), hydrolysis of compound 47a as prepared above gave the title compound; Calcd. MW 466.49. Found MH⁺ 467.1.

$^1$H NMR (300 MHz, CD$_3$OD): δ0.86 (m, 6H), δ1.46 (m, 2H), δ1.83 (m, 1H), δ3.48 (t, 1H, J=7.6 Hz), δ4.48 (s, 2H), δ6.66 (s, 1H), δ6.68 (s, 1H), δ6.95 (s, 1H), δ7.56-7.7 (m, 8).

EXAMPLE 48

(R) 2-{5-[(4-Cyano-benzyl)-(3-methyl-butyl)-amino]-4'-trifluoromethyl-biphenyl-3-yl}-4-methyl-pentanoic acid

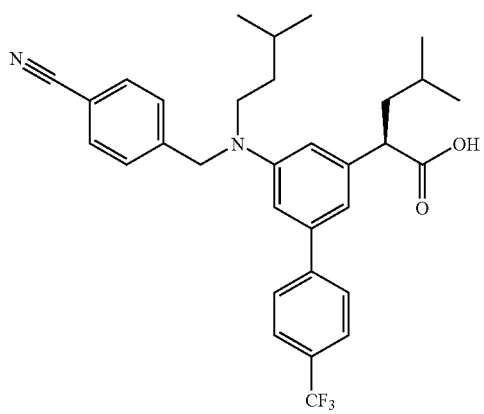

a) (R) 2-{5-[(4-Cyano-benzyl)-(3-methyl-butyl)-amino]-4'-trifluoromethyl-biphenyl-3-yl}-4-methyl-pentanoic acid methyl ester

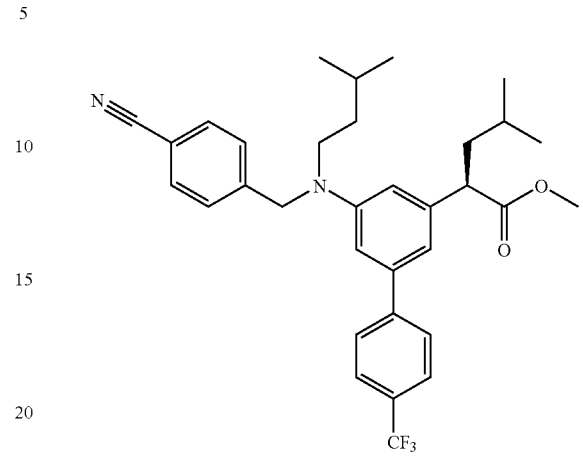

Following the procedure of Example 39, step (a), reaction of 2-[5-(4-Cyano-benzylamino)-4'-trifluoromethyl-biphenyl-3-yl]-4-methyl-pentanoic acid methyl ester, compound 47a with isovaleraldehyde gave the title compound; Calcd. MW 550.67. Found MH⁺ 551.4.

b) (R) 2-{5-[(4-Cyano-benzyl)-(3-methyl-butyl)-amino]-4'-trifluoromethyl-biphenyl-3-yl}-4-methyl-pentanoic acid Following the procedure of Example 29, step (f), hydrolysis of compound 48a as prepared above gave the title compound; Calcd. MW 536.63. Found MH⁺ 537.5.

$^1$H NMR (300 MHz, CD$_3$OD): δ0.86 (m, 6H), δ0.98 (m, 6H), δ1.4-1.8 (m, 5H), δ3.5 (m, 4H), δ4.63 (s, 2H), δ6.7 (s, 1H), δ6.77 (s, 1H), δ7.0 (s, 1H), δ7.4 (d, 2H, J=8.23 Hz), δ7.65 (m, 6H).

EXAMPLE 49

(R) 2-{5-[(3,5-Bis-trifluoromethyl-benzyl)-(3-methyl-butyl)-amino]-4'-trifluoromethyl-biphenyl-3-yl}-4-methyl-pentanoic acid

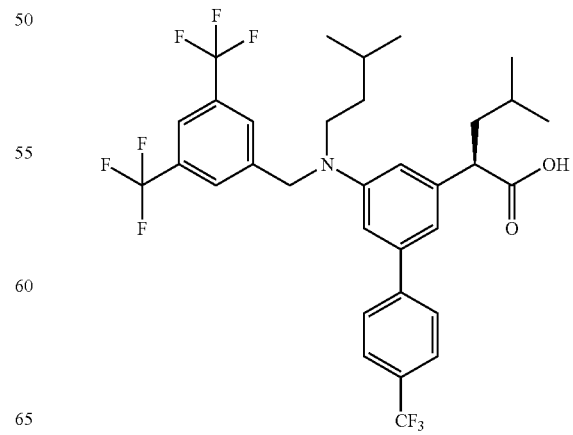

a) (R) 2-{5-[(3,5-Bis-trifluoromethyl-benzyl)-(3-methyl-butyl)-amino]-4'-trifluoromethyl-biphenyl-3-yl}-4-methyl-pentanoic acid methyl ester

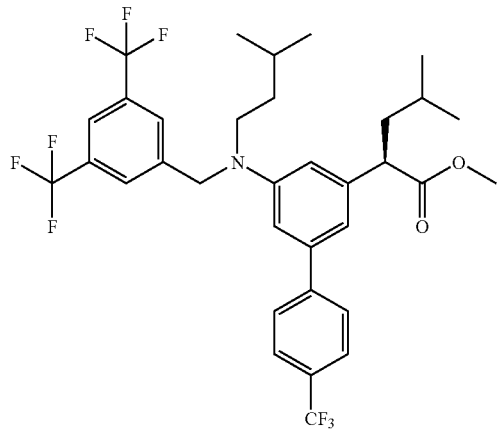

Following the procedure of Example 39, step (a), reaction of 2-[5-(3,5-Bis-trifluoromethyl-benzylamino)-4'-trifluoromethyl-biphenyl-3-yl]-4-methyl-pentanoic acid methyl ester, compound 46a with isovaleraldehyde gave the title compound; Calcd. MW 661.66. Found MH+ 662.4.

b) (R) 2-{5-[(3,5-Bis-trifluoromethyl-benzyl)-(3-methyl-butyl)-amino]-4'-trifluoromethyl-biphenyl-3-yl}-4-methyl-pentanoic acid Following the procedure of Example 29, step (f), hydrolysis of compound 49a as prepared above gave the title compound; Calcd. MW 647.63. Found MH+ 648.2.
$^1$H NMR (300 MHz, CD$_3$OD): δ0.82 (m, 6H), δ0.98 (d, 6H, J=6 Hz), δ61.4-1.77 (m, 5H), δ3.5 (m, 4H), δ4.77 (s, 2H), δ6.71 (s, 1H), δ6.77 (s, 1H), δ7.03 (s, 1H), δ7.66 (m, 4H), δ7.81 (s, 1H), δ7.86 (s, 2H).

EXAMPLE 50

2-(5-{[1-(3,5-Difluoro-phenyl)-4-methyl-pentyl]-methyl-amino}-4'-trifluoromethyl-biphenyl-3-yl)-4-methyl-pentanoic acid

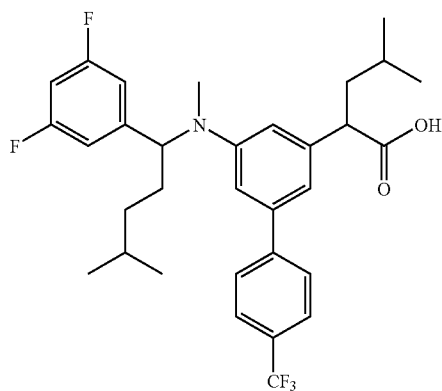

a) 2-(5-{[1-(3,5-Difluoro-phenyl)-4-methyl-pentyl]-methyl-amino}-4'-trifluoromethyl-biphenyl-3-yl)-4-methyl-pentanoic acid

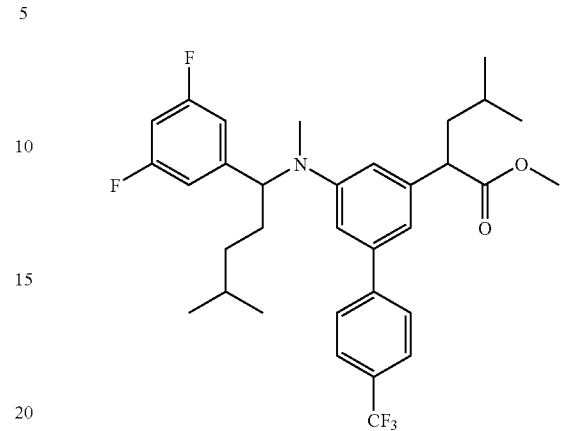

A solution of 2-(5-{[1-(3,5-Difluoro-phenyl)-4-methyl-pentyl]-methyl-amino}-4'-trifluoromethyl-biphenyl-3-yl)-4-methyl-pentanoic acid methyl ester, compound 29e, (0.25 g, 0.4 mmol), MeI (0.3 ml, 4 mmol), Cs$_2$CO$_3$ (0.72 g) and acetonitrile in a sealed reaction tube was heated to 80° C. overnight. The solvent was removed by vacuum and the crude was purified by preparative TLC to give the title compound (50% yield). Calcd. MW 575.67 Found MH+ 576.3.

b) 2-(5-{[1-(3,5-Difluoro-phenyl)-4-methyl-pentyl]-methyl-amino}-4'-trifluoromethyl-biphenyl-3-yl)-4-methyl-pentanoic acid Following the procedure of Example 29, step (f), hydrolysis of compound 50a as prepared above gave the title compound; Calcd. MW 561.64 Found MH+ 562.3. $^1$H NMR (300 MHz, CD$_3$OD): δ0.81 (m, 12H), δ1.17 (m, 2H),), δ1.4-1.54 (m, 3H), δ1.9-1.9 (m, 3H), δ2.7 (d, 3H, J=5.7 Hz), δ3.46 (t, 1H, J=7.7 Hz), δ4.95 (t, 1H, J=7.91 Hz), δ6.66 (t, 1H, J=2.26 Hz), δ6.78 (m, 3H), δ6.89 (s, 1H), δ7.06 (s, 1H), δ7.59 (d, 2H, J=8.2 Hz), δ7.68 (d, 2H, J=8.2 Hz).

EXAMPLE 51

2-(5-(4-fluoro-2-(trifluoromethyl)benzylamino)-4'-(trifluoromethyl)biphenyl-3-yl)-4-methylpentanoic acid

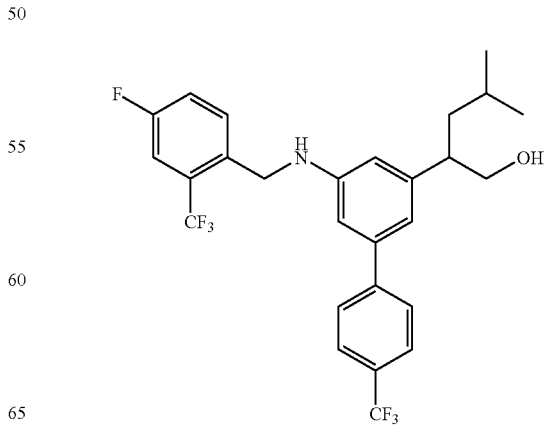

a) 2-(5-(4-fluoro-2-(trifluoromethyl)benzylamino)-4'-(trifluoromethyl)biphenyl-3-yl)-4-methylpentanoic acid ethyl ester

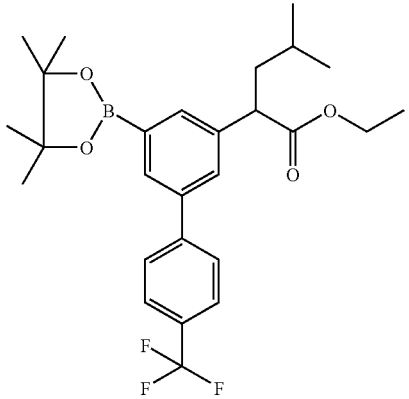

2-(5-trifluoromethanesulfonyloxy-3'-trifluoromethyl-biphenyl-3-yl)-4-methyl-pentanoic acid ethyl ester (3.69 g, 7 mmol) (prepared as in Example 1 in toluene (40 ml) was treated with bispinocolatodiborane (1.94 g, 7.7 mmol), potassium acetate (1.37 g, 14 mmol), diphenylphosphinoferrocene palladium dichloride (0.7 mmol) and heated in a microwave at 150° C. for 15 min. The mixture was filtered and washed with water and EtOAc then the organics were dried and concentrated to afford a yellow oil. This oil was purified by flash column chromatography (0-10% EtOAc) to afford the desired white solid.

¹H-NMR (400 MHz, CD₃Cl): δ 7.42-7.37 (m, 5H), 7.32-7.26 (m, 3H), 7.12-7.08 (m, 1H), 7.00-6.94 (m, 1H), 3.39-3.33 (m, 2H), 2.79-2.66 (m, 2H), 1.31 (d, 6H); RT=3.83 min. Mass spectrum (ESI, m/z): 528 (M+H);

b) 2-(5-(4-fluoro-2-(trifluoromethyl)benzylamino)-4'-(trifluoromethyl)biphenyl-3-yl)-4-methylpentanoic acid ethyl ester

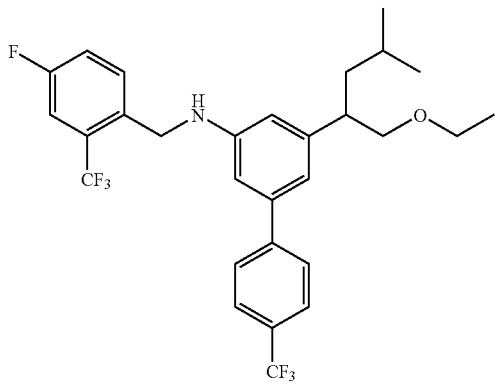

A mixture of 2-(5-(4-fluoro-2-(trifluoromethyl)benzylamino)-4'-(trifluoromethyl)biphenyl-3-yl)-4-methylpentanoic acid ethyl ester (100 mg, 0.20 mmol), as prepared above, 2-trifluoromethyl-4-fluorobenzylamine (20 µL, 0.1 mmol), copper acetate (36 mg, 0.2 mmol), triethylamine (43 µL, 0.3 mmol) and powdered 4 Å molecular sieves in DCM (10 mL) were stirred at room temperature for 2 days. The reaction mixture was concentrated in vacuo. Purification by flash chromatography (EtOAc: petroleum ether) give the title compound.

RT=3.68 min, Mass spectrum (ESI, m/z): 541(M+H);

c) 2-(5-(4-fluoro-2-(trifluoromethyl)benzylamino)-4'-(trifluoromethyl)biphenyl-3-yl)-4-methylpentanoic acid

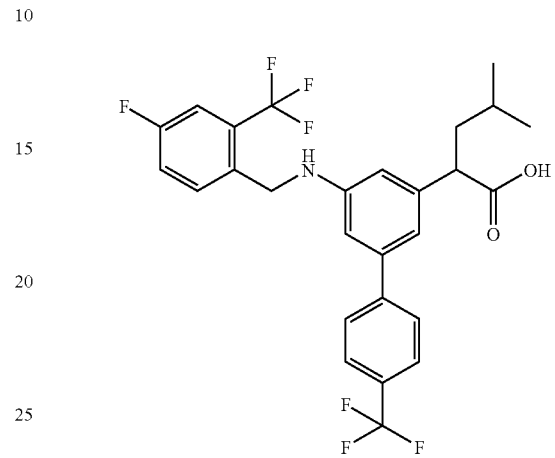

The title compound was prepared from) 2-(5-(4-fluoro-2-(trifluoromethyl)benzylamino)-4'-(trifluoromethyl)biphenyl-3-yl)-4-methylpentanoic acid ethyl ester under the conditions described in Example 24, step (b).

¹H-NMR (400 MHz, CD₃Cl): δ7.42-7.37 (m, 5H), 7.32-7.26 (m, 3H), 7.12-7.08 (m, 1H), 7.00-6.94 (m, 1H), 3.39-3.33 (m, 2H), 2.79-2.66 (m, 4H), 1.31 (d, 6H); RT=3.83 min. Mass spectrum (ESI, m/z): 528 (M+H)

EXAMPLE 52

2-(5-(2,4-difluorobenzylamino)-4'-(trifluoromethyl) biphenyl-3-yl)-4-methyl pentanoic acid

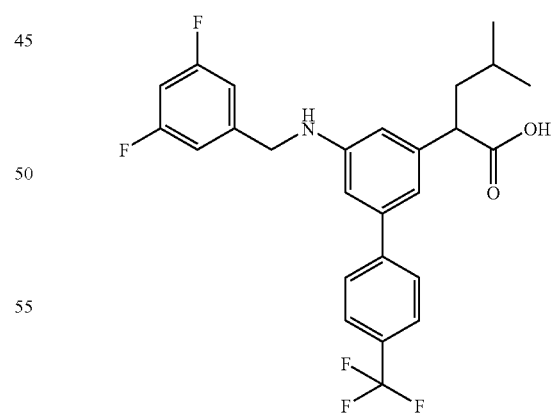

a) 2-(5-(2,4-difluorobenzylamino)-4'-(trifluoromethyl)biphenyl-3-yl)-4-methyl pentanoic acid The title compound was prepared in 56% yield using 2,4-difluorobenzylamine under the conditions described in Example 51, steps (b-c).

¹H-NMR (400 MHz, CD₃Cl): δ 7.61-7.52 (m, 4H), 7.19 (m, 2H), 6.91-6.81 (m, 2H), 6.65-6.54 (m, 2H), 3.70-3.54 (m, 2H), 1.90-1.78 (m, 2H), 1.64-1.59 (m, 1H), 1.47-1.42 (m, 1H), 0.83 (d, 6H); Mass spectrum (ESI, m/z): 478 (M+H), RT=3.62 min.

EXAMPLE 53

4-Methyl-2-[-5-(3,4-dihydroisoquinolin-2(1H)-yl)-4'-(trifluoromethyl) biphenyl-3-yl]-pentanoic acid

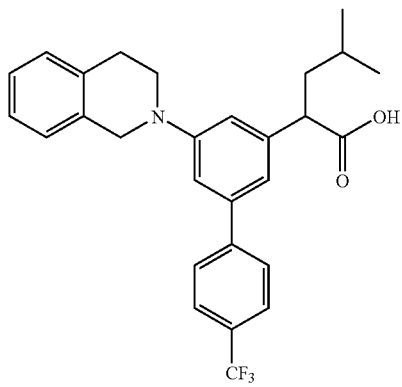

a) 4-Methyl-2-[-5-(3,4-dihydroisoquinolin-2(1H)-yl)-4'-(trifluoromethyl)biphenyl-3-yl]-pentanoic acid methyl ester

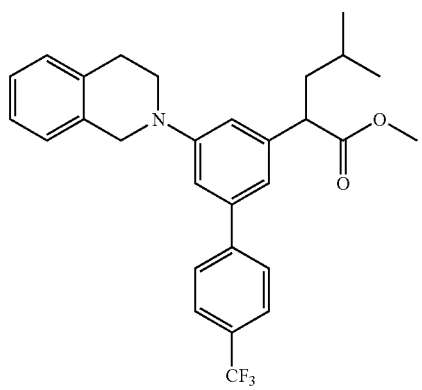

The title compound was prepared in 85% yield from 4-methyl-2-(5-trifluoromethanesulfonyloxy-4'-trifluoromethyl-biphenyl-3-yl)-pentanoic acid methyl ester and tetrahydroisoquinoline under the conditions described in Example 24, step (a).

b) 4-Methyl-2-[4'-trifluoromethyl-5-(7-trifluoromethyl-3,4-dihydro-2H-quinolin-1-yl)-biphenyl-3-yl]-pentanoic acid The title compound was prepared in 100% yield from 4-methyl-2-[4'-trifluoromethyl-5-(7-trifluoromethyl-3,4-dihydro-2H-quinolin-1-yl)-biphenyl-3-yl]-pentanoic acid methyl ester under the conditions described in Example 24, step (b).

¹H-NMR (400 MHz, CDCl₃): δ7.62 (m, 4H), 7.19 (m, 2H), 7.13 (m, 2H), 6.95 (m, 1H), 6.90 (m, 1H), 6.88 (m, 1H), 3.63 (t, 2H), 3.56 (t, 2H), 2.97 (m, 2H), 1.94 (m, 1H), 1.68-1.61 (m, 1H), 1.47-1.44 (m, 1H), 1.21-1.15 (m, 1H), 0.86 (d, 6H); RT=4.19 min

EXAMPLE 54

4-Methyl-2-(5-{[(3-methyl-butyl)-(3,4,5-trifluoro-benzyl)-amino]-methyl}-4'-trifluoromethyl-biphenyl-3-yl)-pentanoic acid

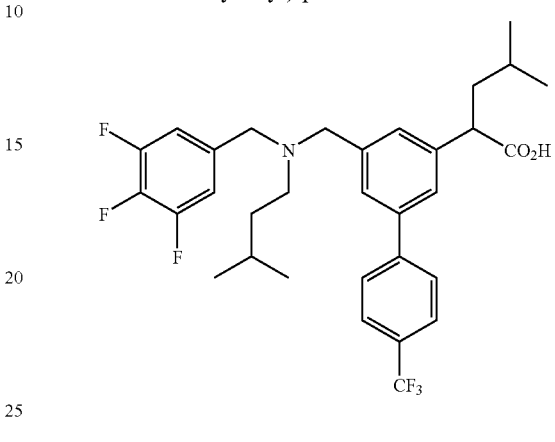

a) 2-(5-Cyano-4'-trifluoromethyl-biphenyl-3-yl)-4-methyl-pentanoic acid ethyl ester

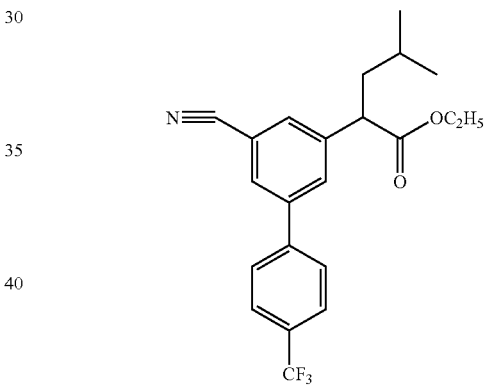

Following a literature procedure (Chackal-Catoen, S. et al. Bioorg. Med. Chem. 2006, 14, 7434), solution of compound 1g (2.18 g, 4.21 mmol) in 19.5 mL of DMF was added to a sealed tube, and zinc cyanide (1.04 g, 8.84 mmol) was added. The resulting suspension was degassed with argon for 10 min, and then tetrakis(triphenylphosphine) palladium (0) (0.49 g, 0.421 mmol) was added. The reaction flask was placed in a preheated 150° C. oil bath and was heated 24 hours. After this period, the reaction mixture was cooled and saturated aqueous NaHCO₃ solution was added. The aqueous layer was extracted with EtOAc three times. The organic extracts were combined and washed five times with brine. After drying over MgSO₄ and filtration, the resulting solution was concentrated in vacuo to provide 2.05 g of a golden brown oil. This material was purified on an ISCO chromatographic system using pure hexanes to 2:1 hexanes:ethyl acetate gradient as eluent to yield 0.93 g (57%) of 2-(5-isocyano-4'-trifluoromethyl-biphenyl-3-yl)-4-methyl-pentanoic acid ethyl ester as a colorless oil.

MH⁺ 390.3

¹H NMR (300 MHz, CDCl₃): δ0.94 (dd, J=6.6, 1.6 Hz, 6H), 1.25 (t, J=7.2 Hz, 3H), 1.42-1.55 (m, 1H), 1.63-1.76 (m,

1H), 1.96-2.10 (m, 1H), 3.75 (t, J=7.8 Hz, 1H), 4.04-4.28 (m, 2H), 7.62-7.71 (m, 3H), 7.73 (br s, 1H), 7.74-7.79 (m, 3H).

b) 2-(5-Aminomethyl-4'-trifluoromethyl-biphenyl-3-yl)-4-methyl-pentanoic acid ethyl ester

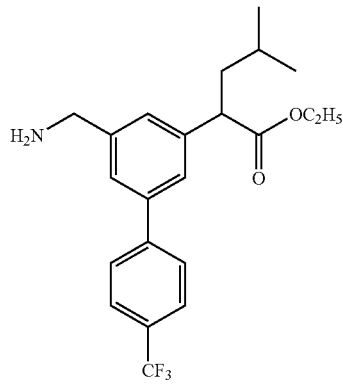

Following a literature procedure (Suh, Y.-G. et al. *J. Med. Chem.* 2005, 18, 7434), solution of compound 54a (0.28 g, 0.719 mmol) was dissolved in 20 mL of ethanol in a Parr hydrogenation bottle. The solution was cooled in ice, and 10% palladium on carbon (0.026 g) and concentrated (12 N) hydrochloric acid solution (0.48 mL) was added. The flask was shaken on a Parr hydrogenation apparatus at 14.5 psi for 5.25 h. After the reaction was terminated, the reaction mixture was filtered through Celite® 545 filter aid. The filtrate was concentrated in vacuo to afford a cream-colored solid. This material was dissolved in dichloromethane, and the resulting solution was washed twice with saturated aqueous $Na_2CO_3$ solution. After drying over $Na_2SO_4$ and subsequent filtration, the resulting solution was concentrated in vacuo to provide 0.28 g (quantitative yield) of 2-(5-aminomethyl-4'-trifluoromethyl-biphenyl-3-yl)-4-methyl-pentanoic acid ethyl ester as a light grey oil.

$MH^+$ 394.4

$^1$H NMR (300 MHz, $CDCl_3$): δ0.93 (br d, J=6.2 Hz, 6H), 1.23 (br t, J=7.0 Hz, 3H), 1.42-1.60 (m, 1H), 1.62-1.78 (m, 1H), 1.95-2.12 (m, 1H), 2.40-2.85 (br s, 2H), 3.75 (m, 1H), 3.96 (br s, 2H), 3.96-4.23 (br m, 2H), 7.34 (br s, 1H), 7.45 (br s, 1H), 7.48 (br s, 1H), 7.68 (br s, 4H).

c) 4-Methyl-2-{5-[(3-methyl-butylamino)-methyl]-4'-trifluoromethyl-biphenyl-3-yl}-pentanoic acid ethyl ester

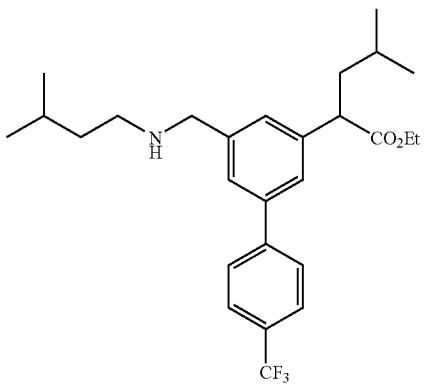

To a solution of compound 54b (0.24 g, 0.610 mmol) in 10 mL of anhydrous methanol, was added isovaleroaldehyde (0.058 g, 0.07 mL, 0.671 mmol). The solution was stirred 45 minutes, and then sodium borohydride (0.046 g, 1.22 mmol) was added. After 20 h of stirring, the reaction mixture was cooled in ice, and HCl (1 N solution, 1 mL) was added. The reaction mixture was stirred for one minute, and then saturated aqueous $Na_2CO_3$ solution was added until the pH was basic. The solution was extracted three times with dichloromethane. The organic extracts were combined and washed with saturated aqueous $Na_2CO_3$ solution, dried ($Na_2SO_4$), and filtered. The filtrate was concentrated to provide a 0.27 g of a pale yellow glass. Purification on a flash silica gel column using 95:4.5:0.5 $CH_2Cl_2$:MeOH:$NH_4OH$ provided 0.25 g (89%) of 4-methyl-2-{5-[(3-methyl-butylamino)-methyl]-4'-trifluoromethyl-biphenyl-3-yl}-pentanoic acid ethyl ester as a colorless oil.

$MH^+$ 464.4

$^1$H NMR (300 MHz, $CDCl_3$): δ0.89 (d, J=6.7 Hz, 6H), 0.93 (d, J=6.6 Hz, 6H), 1.23 (t, J=7.1 Hz, 3H), 1.39-1.59 (m, 3H), 1.58-1.75 (m, 2H), 1.96-2.08 (m, 2H), 2.68 (br t, J=7.5 Hz, 2H), 3.71 (dd, J=7.3, 1.1 Hz 1H), 3.87 (s, 2H), 3.96 (br s, 2H), 4.02-4.23 (br m, 2H), 7.32 (br s, 1H), 7.45 (br d, J=1.5 Hz, 1H), 7.49 (br s, 1H), 7.69 (AB quartet, J=9.1 Hz, 4H).

d) 4-Methyl-2-(5-{[(3-methyl-butyl)-(3,4,5-trifluoro-benzyl)-amino]-methyl}-4'-trifluoromethyl-biphenyl-3-yl)-pentanoic acid ethyl ester

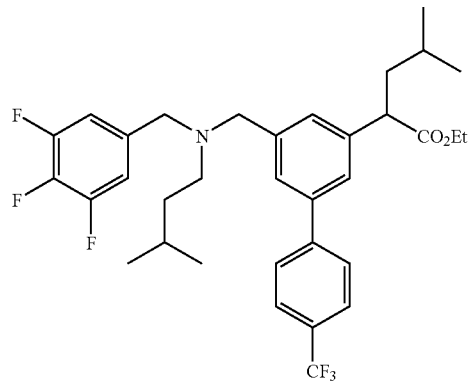

To a solution of compound 54c (0.037 g, 0.091 mmol) in 5 mL of anhydrous dichloromethane was added 3,4,5-trifluorobenzaldehyde (0.029 g, 0.182 mmol). The reaction mixture was stirred 30 minutes, and then sodium triacetoxyborohydride (0.0385 g, 0.182 mmol) was added. After 18 h, 1N NaOH solution was added to the reaction mixture. The resulting mixture was extracted three times with dichloromethane. The organic extracts were combined and washed with 1N NaOH solution, dried ($Na_2SO_4$), filtered, and concentrated to yield a cloudy film. Purification on a flash silica gel column using 1% (5% $NH_4OH$ in MeOH): $CH_2Cl_2$ yielded 0.07 g (quantitative yield) of 4-methyl-2-(5-{[(3-methyl-butyl)-(3,4,5-trifluoro-benzyl)-amino]-methyl}-4'-trifluoromethyl-biphenyl-3-yl)-pentanoic acid ethyl ester as a colorless glass.

$MH^+$ 608.4

$^1$H NMR (300 MHz, $CDCl_3$): δ0.75 (d, J=6.5 Hz, 6H), 0.85 (dd, J=6.6, 1.8 Hz, 6H), 1.15 (t, J=7.1 Hz, 3H), 1.28-1.68 (m, 5H), 1.86-1.99 (m, 1H), 2.38 (br t, J=7.4 Hz, 2H), 3.40 (br s, 2H), 3.53 (br s, 2H), 3.64 (t, J=7.7 Hz 1H), 3.96-4.16 (br m, 2H), 6.92 (dd, J=8.3, 6.8 Hz, 2H), 7.28 (br s, 1H), 7.34 (br d, J=1.4 Hz, 2H), 7.61 (AB quartet, J=8.9 Hz, 4H).

e) 4-Methyl-2-(5-{[(3-methyl-butyl)-(3,4,5-trifluoro-benzyl)-amino]-methyl}-4'-trifluoromethyl-biphenyl-3-yl)-pentanoic acid To a solution of compound 54d (0.07 g, 0.115 mmol) in 5 mL of methanol was added 3N NaOH solution (0.1 mL). The mixture was heated to 60° C. for 3 h. After cooling to ambient temperature, the reaction mixture was concentrated in vacuo. To the residue was added 3N HCl solution. This solution was extracted three times with dichloromethane. The organic extracts were combined, dried ($Na_2SO_4$), filtered, and concentrated to provide a milky film. Analysis by LC-MS indicated this material was a 1:2 mixture of the desired acid and the corresponding methyl ester. This material was resubjected to the reaction conditions described above for 4 h and then was worked up as before to yield 0.05 g of a white foam. LC-MS indicated this material was a 1:1 mixture of the desired acid and the corresponding methyl ester. The foam was dissolved in 10 mL of methanol, and 1 mL of N NaOH solution was added. The reaction mixture was heated to 80° C. for 6 h. After cooling, the workup described before provided 0.03 g (45%) of 4-methyl-2-(5-{[(3-methyl-butyl)-(3,4,5-trifluoro-benzyl)-amino]-methyl}-4'-trifluoromethyl-biphenyl-3-yl)-pentanoic acid as a pale pink foam.
$MH^+$ 580.3
$^1H$ NMR (300 MHz, $CDCl_3$): δ0.73 (d, J=6.4 Hz, 6H), 0.83 (d, J=6.6 Hz, 6H), 1.32-1.48 (m, 2H), 1.54-1.70 (m, 3H), 1.83-2.00 (m, 1H), 2.59-2.96 (br s, 2H), 3.68 (t, J=7.6 Hz, 1H), 3.83-4.62 (br s, 4H), 7.28-7.45 (br s, 2H), 7.44-7.49 (br s, 1H), 7.50-7.55 (br s, 1H), 7.61 (AB quartet, J=8.3 Hz, 4H), 7.77-7.89 (br s, 1H), 12.0-12.65 (br s, 1H).

EXAMPLE 55

2-(5-{[(3,5-Bis-trifluoromethyl-benzyl)-(3-methyl-butyl)-amino]-methyl}-4'-trifluoromethyl-biphenyl-3-yl)-4-methyl-pentanoic acid

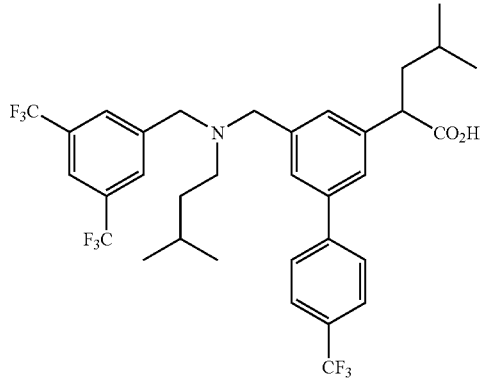

a) 2-(5-{[(3,5-Bis-trifluoromethyl-benzyl)-(3-methyl-butyl)-amino]-methyl}-4'-trifluoromethyl-biphenyl-3-yl)-4-methyl-pentanoic acid ethyl ester

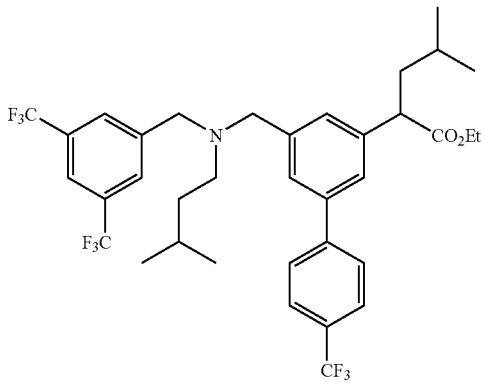

To a solution of compound 54c (0.028 g, 0.0697 mmol) in 5 mL of anhydrous dichloromethane was added 3,5-bis(trifluoromethyl)benzaldehyde (0.038 g, 0.139 mmol). The reaction mixture was stirred 30 minutes, and then sodium triacetoxyborohydride (0.0385 g, 0.182 mmol) was added. After 19 h of stirring, 1N NaOH solution was added to the reaction mixture. The resulting mixture was extracted three times with dichloromethane. The organic extracts were combined and washed with 1N NaOH solution, dried ($Na_2SO_4$), filtered, and concentrated to yield a cloudy film. Purification on a flash silica gel column using 99:0.5:0.5 $CH_2Cl_2$:MeOH:$NH_4OH$ as the eluent yielded 0.07 g (quantitative yield) of 2-(5-{[(3,5-bis-trifluoromethyl-benzyl)-(3-methyl-butyl)-amino]-methyl}-4'-trifluoromethyl-biphenyl-3-yl)-4-methyl-pentanoic acid ethyl ester as a milky glass.
$MH^+$ 690.3
$^1H$ NMR (300 MHz, $CDCl_3$): δ0.73 (d, J=6.5 Hz, 6H), 0.84 (dd, J=6.6, 1.9 Hz, 6H), 1.13 (t, J=7.1 Hz, 3H), 1.12-1.28 (m, 1H), 1.31-1.48 (m, 2H), 1.48-1.68 (m, 2H), 1.86-2.03 (m, 1H), 2.42 (br t, J=7.3 Hz, 2H), 3.56 (s, 2H), 3.60 (s, 2H), 3.51-3.68 (m, 1H), 3.94-4.18 (br m, 2H), 7.27 (br s, 1H), 7.36 (br s, 1H), 7.37 (br s, 1H), 7.60 (AB quartet, J=8.9 Hz, 4H), 7.62 (br s, 1H), 7.78 (br s, 2H).

b) 2-(5-{[(3,5-Bis-trifluoromethyl-benzyl)-(3-methyl-butyl)-amino]-methyl}-4'-trifluoromethyl-biphenyl-3-yl)-4-methyl-pentanoic acid To a solution of compound 55a (0.07 g, 0.115 mmol) in 5 mL of methanol was added 3N NaOH solution (0.06 mL). The mixture was heated to 55° C. for 4 h. After cooling to ambient temperature, the reaction mixture was concentrated in vacuo. To the residue was added 3N HCl solution, and the resulting solution was extracted three times with dichloromethane. The organic extracts were combined, dried ($Na_2SO_4$), filtered, and concentrated to provide a white foam. Analysis by LC-MS indicated this material was a 3:1 mixture of the desired acid and the corresponding methyl ester. This material was dissolved in MeOH (1 mL), and 3N NaOH solution (0.06 mL) was added. The mixture was heated to 55° C. for 4 h and then was worked up as before to yield 0.06 g (79%) of 2-(5-{[(3,5-bis-trifluoromethyl-benzyl)-(3-methyl-butyl)-amino]-methyl}-4'-trifluoromethyl-biphenyl-3-yl)-4-methyl-pentanoic acid as a white foam.
$M^+$ 662.4
$^1H$ NMR (300 MHz, $CDCl_3$): δ0.73 (d, J=6.3 Hz, 6H), 0.82 (d, J=6.5 Hz, 6H), 1.33-1.48 (m, 2H), 1.53-1.71 (m, 3H), 1.84-2.03 (m, 1H), 2.63-2.80 (br s, 2H), 3.70 (t, J=7.7 Hz, 1H), 3.65-4.38 (br s, 4H), 7.32-7.45 (br s, 1H), 7.45-7.52 (br s, 1H), 7.52 (br s, 1H), 7.61 (AB quartet, J=8.3 Hz, 4H), 7.75-7.85 (br s, 2H), 8.02-8.32 (br s, 2H), 12.20-12.82 (br s, 1H).

EXAMPLE 56

4-Methyl-2-(5-{[(3-methyl-butyl)-(4-trifluoromethyl-benzyl)-amino]-methyl}-4'-trifluoromethyl-biphenyl-3-yl)-pentanoic acid

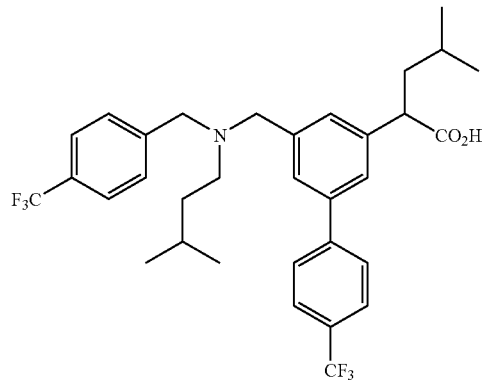

a) 4-Methyl-2-(5-{[(3-methyl-butyl)-(4-trifluorom-ethyl-benzyl)-amino]-methyl}-4'-trifluoromethyl-biphenyl-3-yl)-pentanoic acid ethyl ester

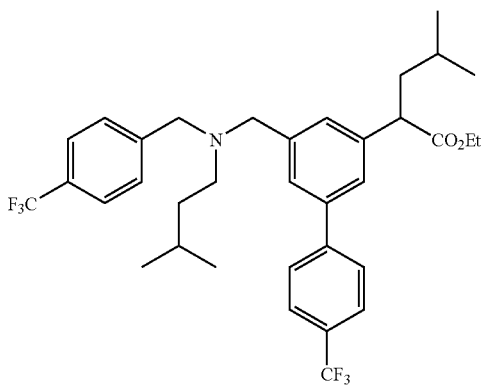

Using the procedure described for Example 54, except substituting 4-trifluoromethylbenzaldehyde for 3,4,5-trifluorobenzaldehyde, compound 54c was converted to 4-methyl-2-(5-{[(3-methyl-butyl)-(4-trifluoromethyl-benzyl)-amino]-methyl}-4'-trifluoromethyl-biphenyl-3-yl)-pentanoic acid ethyl ester as a milky glass.
MH+ 622.3
$^1$H NMR (300 MHz, CDCl$_3$): δ0.73 (d, J=6.6 Hz, 6H), 0.84 (dd, J=6.6, 2.1 Hz, 6H), 1.13 (t, J=7.1 Hz, 3H), 1.30-1.69 (m, 5H), 1.86-1.98 (m, 1H), 2.39 (br t, J=7.4 Hz, 2H), 3.54 (br s, 4H), 3.63 (t, J=7.7 Hz, 3H), 3.94-4.13 (br m, 2H), 7.44 (AB quartet, J=8.1 Hz, 4H), 7.61 (AB quartet, J=8.8 Hz, 4H).

b) 4-Methyl-2-(5-{[(3-methyl-butyl)-(4-trifluorom-ethyl-benzyl)-amino]-methyl}-4'-trifluoromethyl-biphenyl-3-yl)-pentanoic acid Using the procedure described for Example 54, compound 56a was converted to 4-methyl-2-(5-{[(3-methyl-butyl)-(4-trifluoromethyl-benzyl)-amino]-methyl}-4'-trifluoromethyl-biphenyl-3-yl)-pentanoic acid as a white solid.
MH+ 594.3
$^1$H NMR (300 MHz, CDCl$_3$): δ0.77 (d, J=6.6 Hz, 6H), 0.89 (d, J=6.5 Hz, 6H), 1.38-1.56 (m, 2H), 1.62-1.77 (m, 3H), 1.82-2.08 (m, 1H), 2.82-2.96 (br m, 2H), 3.76 (t, J=7.7 Hz, 1H), 4.17 (br s, 2H), 4.23 (br s, 2H), 7.52 (br s, 1H), 7.59 (br s, 1H), 7.60-7.68 (br m, 4H), 7.70 (br s, 1H), 7.76 (AB quartet, J=8.0 Hz, 4H), 7.92 (br s, 1H), 11.30-12.80 (br s, 1H).

EXAMPLE 57

(5-{[(4-Chloro-3-fluoro-benzyl)-(3-methyl-butyl)-amino]-methyl}-4'-trifluoromethyl-biphenyl-3-yl)-acetic acid

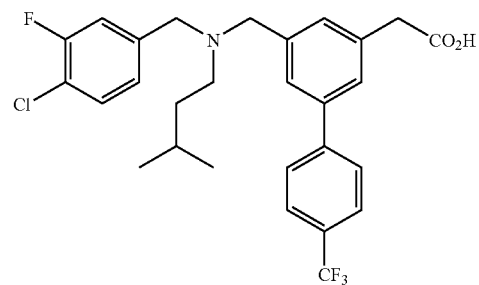

a) (5-Cyano-4'-trifluoromethyl-biphenyl-3-yl)-acetic acid ethyl ester

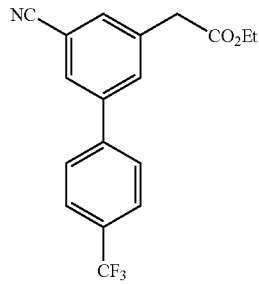

Using the procedure described for Example 54, compound 32a was converted to (5-cyano-4'-trifluoromethyl-biphenyl-3-yl)-acetic acid ethyl ester as a colorless oil.
MH+ not detected
$^1$H NMR (300 MHz, CDCl$_3$): δ1.27 (t, J=7.2 Hz, 3H), 3.73 (s, 2H), 4.21 (q, J=7.2 Hz, 2H), 7.62 (br s, 1H), 7.71 (AB quartet J=7.9 Hz, 4H), 7.74 (br s, 1H), 7.78 (br s, 1H).

b) (5-Aminomethyl-4'-trifluoromethyl-biphenyl-3-yl)-acetic acid ethyl ester

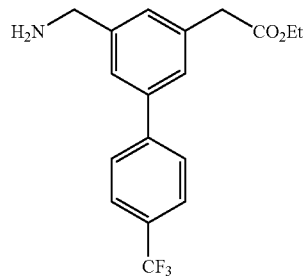

Using the procedure described for Example 54, compound 57a was converted to (5-aminomethyl-4'-trifluoromethyl-biphenyl-3-yl)-acetic acid ethyl ester as a golden-brown oil.
MH+ 338.3
$^1$H NMR (300 MHz, CDCl$_3$): δ0.98-1.68 (br m, 3H), 1.95-3.0 (br s, 2H), 3.58 (br s, 2H), 3.88 (br m, 2H), 4.10 (br s, 2H), 6.84-8.12 (br m, 7H).

c) {5-[(3-Methyl-butylamino)-methyl]-4'-trifluorom-ethyl-biphenyl-3-yl}-acetic acid ethyl ester

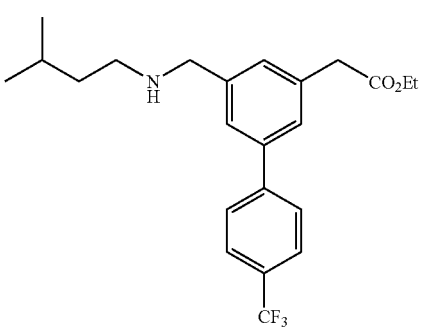

Using the procedure described for Example 54, compound 57b was converted to {5-[(3-methyl-butylamino)-methyl]-4'-trifluoromethyl-biphenyl-3-yl}-acetic acid ethyl ester as a colorless oil.

MH⁺ 408.3

¹H NMR (300 MHz, CDCl₃): δ0.90 (d, J=7.2 Hz, 6H), 1.27 (t, J=7.1 Hz, 6H), 1.38-1.49 (m, 3H), 1.56-1.72 (m, 1H), 2.68 (t, J=7.5 Hz, 2H), 3.66-3.72 (m, 2H), 3.85 (s, 2H), 4.17 (q, J=7.1 Hz, 2H), 7.30 (br s, 1H), 7.41 (br s, 1H), 7.47 (s, 1H), 7.68 (AB quartet, J=9.5 Hz, 4H).

d) (5-{[(4-Chloro-3-fluoro-benzyl)-(3-methyl-butyl)-amino]-methyl}-4'-trifluoromethyl-biphenyl-3-yl)-acetic acid ethyl ester

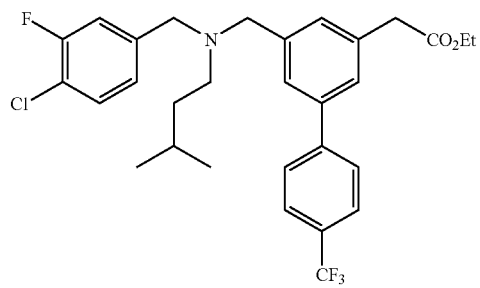

Using the procedure described for Example 54, except substituting compound 57c for compound 54c and 3-chloro-4-fluoromethylbenzaldehyde for 3,4,5-trifluorobenzaldehyde, compound 57c was converted to 2-(5-{[(4-chloro-3-fluoro-benzyl)-(3-methyl-butyl)-amino]-methyl}-4'-trifluoromethyl-biphenyl-3-yl)-4-methyl-pentanoic acid ethyl ester as a milky glass.

MH⁺ 550.3/552.3

¹H NMR (300 MHz, CDCl₃): δ0.74 (d, J=6.6 Hz, 6H), 1.19 (t, J=7.1 Hz, 3H), 1.28-1.41 (m, 2H), 1.43-1.57 (m, 1H), 2.38 (br t, J=7.4 Hz, 2H), 3.44 (br s, 2H), 3.53 (br s, 2H), 3.57-3.64 (m, 2H), 4.09 (t, J=7.1 Hz, 2H), 6.99 (br d, J=7.1 Hz, 1H), 7.11 (dd, J=10.1 Hz, 1.7 Hz, 1H), 7.18-7.27 (m, 2H), 7.31 (br s, 1H), 7.38 (br s, 1H), 7.44 (AB quartet, J=11.0 Hz, 4H).

e) 2-(5-{[(4-Chloro-3-fluoro-benzyl)-(3-methyl-butyl)-amino]-methyl}-4'-trifluoromethyl-biphenyl-3-yl)-4-methyl-pentanoic acid Using the procedure described for Example 54, compound 57d was converted to (5-{[(4-chloro-3-fluoro-benzyl)-(3-methyl-butyl)-amino]-methyl}-4'-trifluoromethyl-biphenyl-3-yl)-acetic acid as a white powder.

MH⁺ 522.3

¹H NMR (300 MHz, DMSO-d₆): δ0.86 (d, J=6.5 Hz, 6H), 1.44-1.62 (m, 1H), 1.65-1.78 (m, 2H), 2.95-3.07 (br m, 2H), 3.77 (s, 2H), 4.41-4.54 (br s, 4H), 7.50-7.61 (br m, 2H), 7.70-7.87 (br m, 4H), 7.96 (AB quartet, J=8.5 Hz, 4H), 10.93 (br s, 1H).

EXAMPLE 58

(5-{[(3-Methyl-butyl)-(4-trifluoromethyl-benzyl)-amino]-methyl}-4'-trifluoromethyl-biphenyl-3-yl)-acetic acid

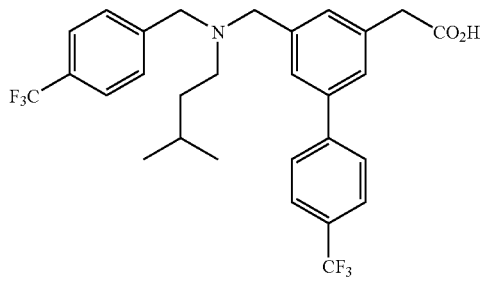

a) (5-{[(3-Methyl-butyl)-(4-trifluoromethyl-benzyl)-amino]-methyl}-4'-trifluoromethyl-biphenyl-3-yl)-acetic acid ethyl ester

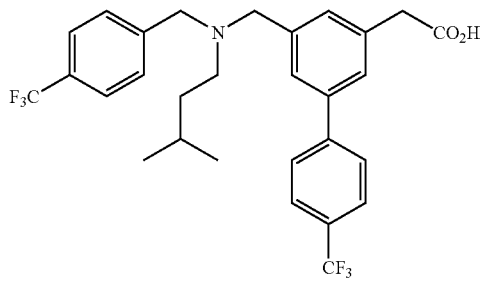

Using the procedure described for Example 54 except substituting compound 57c for compound 54c and 4-trifluoromethylbenzaldehyde for 3,4,5-trifluorobenzaldehyde, compounds 57c was converted to (5-{[(3-methyl-butyl)-(4-trifluoromethyl-benzyl)-amino]-methyl}-4'-trifluoromethyl-biphenyl-3-yl)-acetic acid ethyl ester as a milky glass. which was a milky glass.

MH⁺ 566.4

¹H NMR (300 MHz, CDCl₃): δ0.81 (d, J=6.6 Hz, 6H), 1.23 (t, J=7.1 Hz, 3H), 1.38-1.47 (m, 2H), 1.53-1.66 (m, 1H), 2.47 (br t, J=7.4 Hz, 2H), 3.62 (br s, 4H), 3.65-3.72 (m, 2H), 4.16 (t, J=7.1 Hz, 2H), 7.31 (br s, 1H), 7.38 (br s, 1H), 7.43-7.52 (m, 3H), 7.55 (d, J=8.2 Hz, 2H), 7.68 (AB quartet, J=8.9 Hz, 4H).

b) (5-{[(3-Methyl-butyl)-(4-trifluoromethyl-benzyl)-amino]-methyl}-4'-trifluoromethyl-biphenyl-3-yl)-acetic acid Using the procedure described for Example 54, compound 58a was converted to (5-{[(3-methyl-butyl)-(4-trifluoromethyl-benzyl)-amino]-methyl}-4'-trifluoromethyl-biphenyl-3-yl)-acetic acid as a white powder.

MH⁺ 538.3

¹H NMR (300 MHz, DMSO-d₆): δ0.86 (d, J=6.5 Hz, 6H), 1.47-1.72 (m, 1H), 1.67-1.80 (m, 2H), 2.98-3.12 (br m, 2H), 3.78 (s, 2H), 4.51 (br s, 2H), 4.57 (br s, 2H), 7.57 (br s, 1H), 7.8 (br s, 1H), 7.86-8.02 (br m, 9H), 10.68 (br s, 1H), 12.56 (br s, 1H).

EXAMPLE 59

2-(5-{[(3,5-Difluoro-benzyl)-(3-methyl-butyl)-amino]-methyl}-4'-trifluoromethyl-biphenyl-3-yl)-4-methyl-pentanoic acid

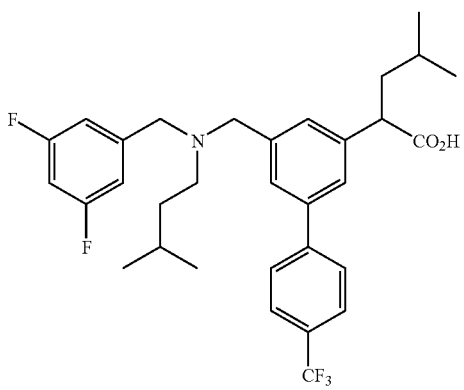

a) 2-(5-{[(3,5-Difluoro-benzyl)-(3-methyl-butyl)-amino]-methyl}-4'-trifluoromethyl-biphenyl-3-yl)-4-methyl-pentanoic acid ethyl ester

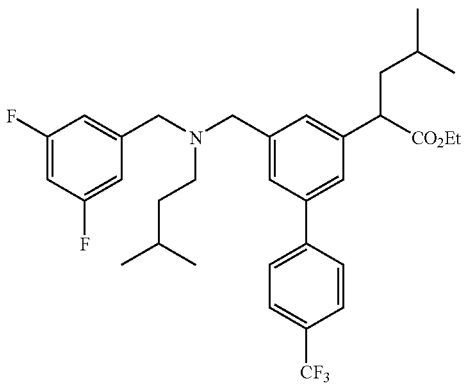

Using the procedure described for Example 54 except substituting 3,5-difluorobenzaldehyde for 3,4,5-trifluorobenzaldehyde, compound 54c was converted to 2-(5-{[(3,5-difluoro-benzyl)-(3-methyl-butyl)-amino]-methyl}-4'-trifluoromethyl-biphenyl-3-yl)-4-methyl-pentanoic acid ethyl ester as a milky glass.

MH⁺ 590.4

¹H NMR (300 MHz, CDCl₃): δ0.74 (d, J=6.5 Hz, 6H), 0.85 (dd, J=6.6, 1.8 Hz, 6H), 1.14 (t, J=7.1 Hz, 3H), 1.30-1.68 (m, 3H), 1.87-2.02 (m, 1H), 2.39 (br t, J=7.4 Hz, 2H), 3.45 (br s, 2H), 3.54 (Br s, 2H), 3.57-3.68 (br m, 1H), 3.94-4.17 (br m, 2H), 6.58 (tt, J=9.0, 2.3 Hz, 1H), 6.83 (dd, J=8.1, 1.9 Hz, 2H), 7.29 (br s, 1H), 7.35 (br s, 1H), 7.36 (br s, 1H), 7.61 (AB quartet, J=9.5 Hz, 4H).

b) 2-(5-{[(3,5-Difluoro-benzyl)-(3-methyl-butyl)-amino]-methyl}-4'-trifluoromethyl-biphenyl-3-yl)-4-methyl-pentanoic acid Using the procedure described for Example 54, compound 59a was converted to 2-(5-{[(3,5-Difluoro-benzyl)-(3-methyl-butyl)-amino]-methyl}-4'-trifluoromethyl-biphenyl-3-yl)-4-methyl-pentanoic acid as a white foam.

MH⁺ 562.3

¹H NMR (300 MHz, CDCl₃): δ0.81 (d, J=6.5 Hz, 6H), 0.92 (d, J=6.5 Hz, 6H), 1.42-1.57 (m, 2H), 1.54-1.82 (m, 3H), 1.94-2.12 (m, 1H), 2.85-3.01 (br m, 2H), 3.79 (br t, J=7.7 Hz, 1H), 4.03-4.16 (br m, 2H), 4.22-4.36 (br m, 2H), 6.87 (br t, J=8.7 Hz, 1H), 7.30 (br d, J=5.3 Hz, 1H), 7.54 (br s, 1H), 7.62 (br s, 1H), 7.69 (br s, 1H), 7.76 (AB quartet, J=8.3 Hz, 4H), 7.97 (br d, J=14.9 Hz, 1H), 12.38-12.62 (br s, 1H).

EXAMPLE 60

2-(5-{[(4-Fluoro-2-trifluoromethyl-benzyl)-(3-methyl-butyl)-amino]-methyl}-4'-trifluoromethyl-biphenyl-3-yl)-4-methyl-pentanoic acid

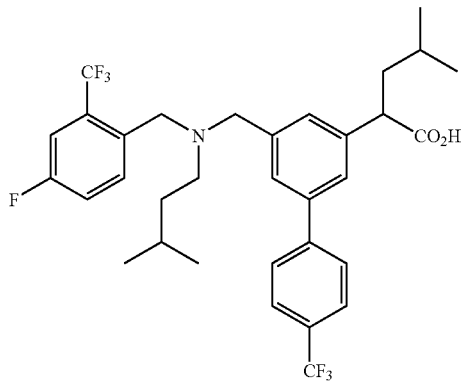

a) 2-(5-{[(4-Fluoro-2-trifluoromethyl-benzyl)-(3-methyl-butyl)-amino]-methyl}-4'-trifluoromethyl-biphenyl-3-yl)-4-methyl-pentanoic acid ethyl ester

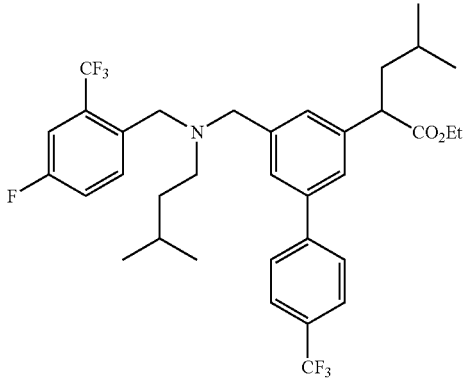

Using the procedure described for Example 54 except substituting 4-fluoro-2-trifluoromethylbenzaldehyde for 3,4,5-trifluorobenzaldehyde, compound 54c was converted to 2-(5-{[(4-Fluoro-2-trifluoromethyl-benzyl)-(3-methyl-butyl)-amino]-methyl}-4'-trifluoromethyl-biphenyl-3-yl)-4-methyl-pentanoic acid ethyl ester as a cloudy white film.

MH⁺ 640.3

$^1$H NMR (300 MHz, CDCl$_3$): δ0.72 (d, J=6.6 Hz, 6H), 0.84 (dd, J=6.6, 2.5 Hz, 6H), 1.13 (t, J=7.1 Hz, 3H), 1.28-1.67 (m, 5H), 1.85-1.99 (m, 1H), 2.39 (br t, J=7.4 Hz, 2H), 3.55-3.72 (m, 3H), 3.93-4.18 (br m, 2H), 7.13 (dd, J=8.3, 2.5 Hz, 1H), 7.23 (dd, J=9.1, 2.6 Hz, 1H), 7.29 (br s, 1H), 7.33 (br s, 1H), 7.36 (br s, 1H), 7.59 (AB quartet, 4H), 7.85 (dd, J=8.6, 5.9 Hz, 1H).

b) 2-(5-{[(4-Fluoro-2-trifluoromethyl-benzyl)-(3-methyl-butyl)-amino]-methyl}-4'-trifluoromethyl-biphenyl-3-yl)-4-methyl-pentanoic acid Using the procedure described for the preparation of Example 54, compound 60a was converted to 2-(5-{[(4-fluoro-2-trifluoromethyl-benzyl)-(3-methyl-butyl)-amino]-methyl}-4'-trifluoromethyl-biphenyl-3-yl)-4-methyl-pentanoic acid as a cloudy yellow gum.

MH$^+$ 612.3

$^1$H NMR (300 MHz, CDCl$_3$): δ0.81 (d, J=6.6 Hz, 6H), 0.92 (d, J=6.5 Hz, 6H), 1.16-1.32 (m, 1H), 1.44-1.55 (m, 2H), 1.62-1.83 (m, 2H), 1.95-2.12 (m, 1H), 2.82-3.12 (br m, 2H), 3.78 (t, J=7.7 Hz, 1H), 4.12-4.25 (br s, 2H), 4.32-4.44 (br s, 2H), 7.33-7.43 (m, 3H), 7.51 (br s, 1H), 7.61 (br s, 1H), 7.90 (br s, 1H), 8.86-9.97 (br s, 1H), 12.50-12.73 (br s, 1H).

EXAMPLE 61

4-Methyl-2-(5-{[(3-methyl-butyl)-(3-trifluoromethyl-benzyl)-amino]-methyl}-4'-trifluoromethyl-biphenyl-3-yl)-pentanoic acid

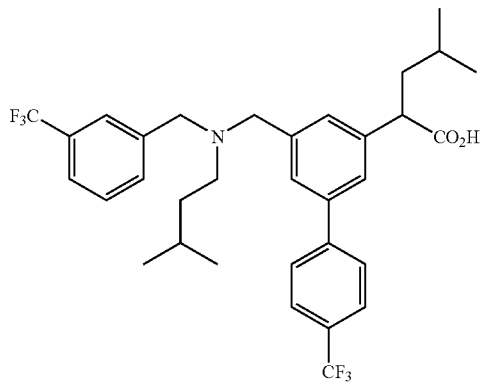

a) 4-Methyl-2-(5-{[(3-methyl-butyl)-(3-trifluoromethyl-benzyl)-amino]-methyl}-4'-trifluoromethyl-biphenyl-3-yl)-pentanoic acid ethyl ester

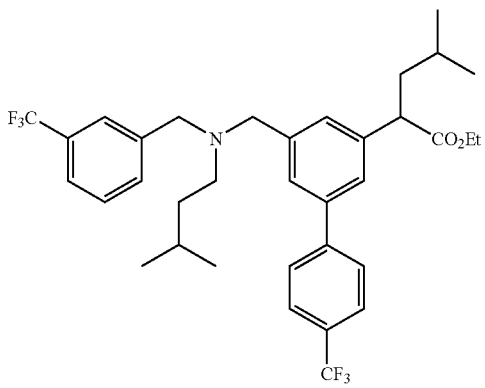

Using the procedure described for Example 54 except substituting 3-trifluoromethylbenzaldehyde for 3,4,5-trifluorobenzaldehyde, compound 54c was converted to 4-methyl-2-(5-{[(3-methyl-butyl)-(3-trifluoromethyl-benzyl)-amino]-methyl}-4'-trifluoromethyl-biphenyl-3-yl)-pentanoic acid ethyl ester as a milky glass.

MH$^+$ 622.3

$^1$H NMR (300 MHz, CDCl$_3$): δ0.69-0.77 (br m, 6H), 0.78-0.91 (br m, 6H), 1.09-1.22 (br m, 3H), 1.30-1.51 (m, 5H), 1.87-2.03 (m, 1H), 2.34-2.46 (m, 2H), 3.54 (br s, 4H), 3.52-3.70 (br m, 1H), 3.93-4.15 (br m, 2H), 7.19 (m, 1H), 7.26-7.52 (m, 5H) 7.56-7.72 (m, 5H).

b) 4-Methyl-2-(5-{[(3-methyl-butyl)-(3-trifluoromethyl-benzyl)-amino]-methyl}-4'-trifluoromethyl-biphenyl-3-yl)-pentanoic acid Using the procedure described for the preparation of Example 54, compound 61a was converted to 4-methyl-2-(5-{[(3-methyl-butyl)-(3-trifluoromethyl-benzyl)-amino]-methyl}-4'-trifluoromethyl-biphenyl-3-yl)-pentanoic acid as a yellow glass.

MH$^+$ 594.3

$^1$H NMR (300 MHz, CDCl$_3$): δ0.69 (d, J=6.2 Hz, 6H), 0.84 (d, J=6.3 Hz, 6H), 1.34-1.54 (m, 4H), 1.57-1.72 (m, 1H), 1.86-2.02 (m, 1H), 2.42-2.62 (br m, 2H), 3.53-3.82 (m, 5H), 7.27-7.49 (br m, 4H), 7.49-7.68 (br m, 7H).

EXAMPLE 62

2-(5-{[(4-Fluoro-benzyl)-(3-methyl-butyl)-amino]-methyl}-4'-trifluoromethyl-biphenyl-3-yl)-4-methyl-pentanoic acid

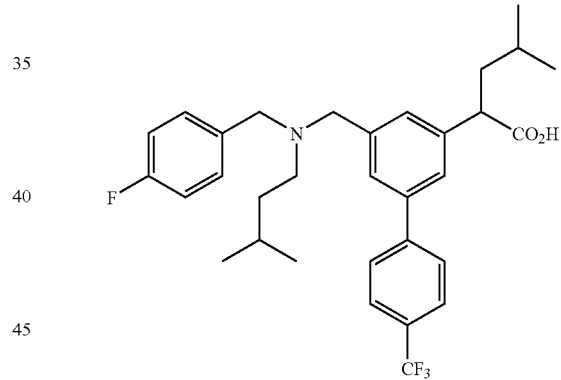

a) 2-(5-{[(4-Fluoro-benzyl)-(3-methyl-butyl)-amino]-methyl}-4'-trifluoromethyl-biphenyl-3-yl)-4-methyl-pentanoic acid ethyl ester

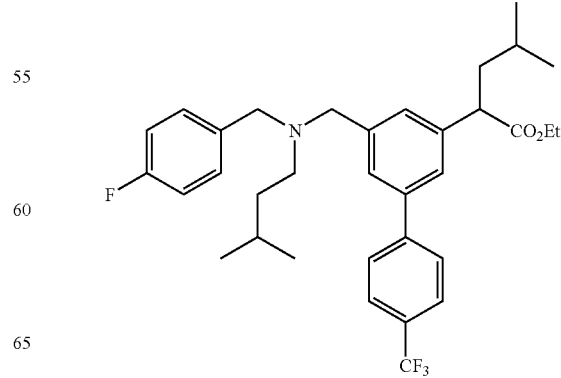

Using the procedure described Example 54 except substituting 4-fluorobenzaldehyde for 3,4,5-trifluorobenzaldehyde, compound 54c was converted to 2-(5-{[(4-fluoro-benzyl)-(3-methyl-butyl)-amino]-methyl}-4'-trifluoromethyl-biphenyl-3-yl)-4-methyl-pentanoic acid ethyl ester as a milky glass.

MH+ 572.4

¹H NMR (300 MHz, CDCl₃): δ0.72 (d, J=6.3 Hz, 6H), 0.84 (dd, J=6.6, 1.8 Hz, 6H), 1.13 (t, J=7.2 Hz, 3H), 1.20-1.70 (m, 5H), 1.86-1.99 (m, 1H), 2.37 (br t, J=7.3 Hz, 2H), 3.44 (br s, 2H), 3.51 (br s, 2H), 3.54-3.68 (m, 1H), 3.94-4.17 (br m, 2H), 6.91 (br t, J=8.8 Hz, 2H), 7.21-7.28 (m, 1H), 7.28 (br s, 1H), 7.33 (br s, 1H), 7.37 (br s, 1H), 7.44 (AB quartet J=8.1 Hz, 4H), 7.61 (AB quartet, J=9.5 Hz, 4H).

b) 2-(5-{[(4-Fluoro-benzyl)-(3-methyl-butyl)-amino]-methyl}-4'-trifluoromethyl-biphenyl-3-yl)-4-methyl-pentanoic acid Using the procedure described for the preparation of Example 54, compound 62a was converted to 2-(5-{[(4-Fluoro-benzyl)-(3-methyl-butyl)-amino]-methyl}-4'-trifluoromethyl-biphenyl-3-yl)-4-methyl-pentanoic acid as a white solid.

MH+ 544.3

¹H NMR (300 MHz, CDCl₃): δ0.71 (d, J=6.5 Hz, 6H), 0.83 (d, J=6.5 Hz, 6H), 1.29-1.51 (m, 2H), 1.54-1.72 (m, 3H), 1.86-2.02 (m, 1H), 2.73-2.87 (br m, 2H), 3.70 (t, J=7.7 Hz, 1H), 3.91-4.11 (br m, 2H), 4.13-4.28 (br m, 2H), 7.01 (br d, J=8.4 Hz, 2H), 7.43 (br s, 1H), 7.51-7.72 (br m, 7H), 7.88 (br d, J=12.5 Hz, 1H), 11.87-12.18 (br s, 1H).

EXAMPLE 63

4-Methyl-2-(5-{[(3-methyl-butyl)-(4-trifluoromethyl-phenyl)-amino]-methyl}-4'-trifluoromethyl-biphenyl-3-yl)-pentanoic acid

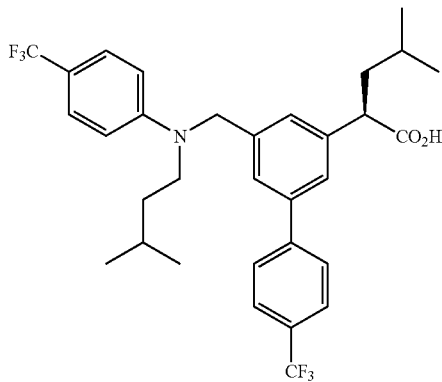

a) 2-(5-Cyano-4'-trifluoromethyl-biphenyl-3-yl)-4-methyl-pentanoic acid methyl ester

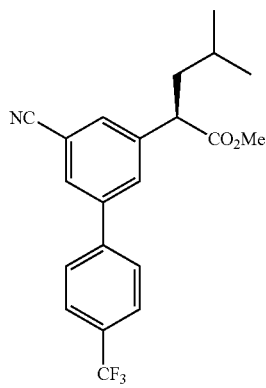

Using the procedure described for 54a, except substituting (R)-enantiomer of 4-methyl-2-(5-trifluoromethanesulfonyloxy-4'-trifluoromethyl-biphenyl-3-yl)-pentanoic acid methyl ester for 1g, 2-(5-cyano-4'-trifluoromethyl-biphenyl-3-yl)-4-methyl-pentanoic acid methyl ester was prepared as a white solid.

MH+ not detected

¹H NMR (300 MHz, CDCl₃): δ0.94 (dd, J=6.6, 0.9 Hz, 6H), 1.38-1.55 (m, 1H), 1.63-1.77 (m, 1H), 1.98-2.10 (m, 1H), 3.70 (s, 3H), 3.77 (t, J=7.8 Hz, 1H), 7.63-7.69 (m, 3H), 7.72-7.79 (m, 4H).

b) 2-(5-Aminomethyl-4'-trifluoromethyl-biphenyl-3-yl)-4-methyl-pentanoic acid methyl ester

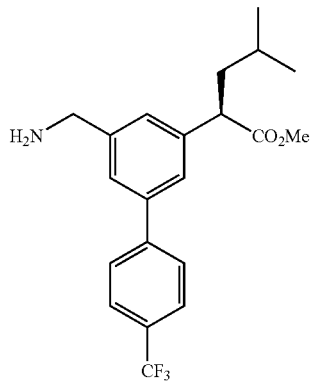

Using the procedure described for 54b, compound 63a was converted to 2-(5-aminomethyl-4'-trifluoromethyl-biphenyl-3-yl)-4-methyl-pentanoic acid methyl ester as a dark brown oil, containing ca. 30% of the corresponding ethyl ester.

MH+ 380.2

¹H NMR (300 MHz, CDCl₃): δ0.93 (br d, J=5.9 Hz, 6H), 1.38-1.56 (br m, 1H), 1.59-1.78 (br m, 1H), 1.95-2.12 (br m, 1H), 3.68 (s, 3H), 3.65-3.82 (br m, 1H), 3.95 (br s, 2H), 7.32 (br s, 1H), 7.43 (br s, 1H), 7.46 (br s, 1H), 7.69 (br s, 4H).

c) 4-Methyl-2-{5-[(3-methyl-butylamino)-methyl]-4'-trifluoromethyl-biphenyl-3-yl}-pentanoic acid methyl ester

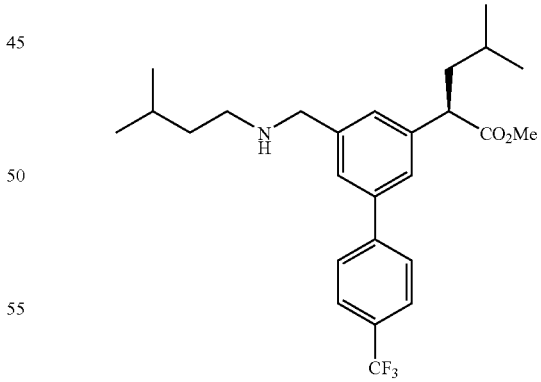

Using the procedure described for 54c, compound 63b was converted to 4-methyl-2-{5-[(3-methyl-butylamino)-methyl]-4'-trifluoromethyl-biphenyl-3-yl}-pentanoic acid methyl ester as a colorless oil, containing ca. 20% of the corresponding ethyl ester.

MH+ 450.3

¹H NMR (300 MHz, CDCl₃): δ0.87-0.97 (m, 12H), 1.37-1.57 (br m, 4H), 1.57-1.76 (br m, 2H), 1.96-2.08 (br m, 1H), 2.67 (br t, J=7.5 Hz, 2H), 3.67 (s, 3H), 3.68-3.78 (br m, 1H), 3.85 (br s, 2H), 7.30 (br s, 1H), 7.43 (br d, J=1.5 Hz, 1H), 7.46 (br d, J=1.3 Hz, 1H), 7.69 (br s, 4H).

d) 4-Methyl-2-(5-{[(3-methyl-butyl)-(4-trifluoromethyl-phenyl)-amino]-methyl}-4'-trifluoromethyl-biphenyl-3-yl)-pentanoic acid methyl ester

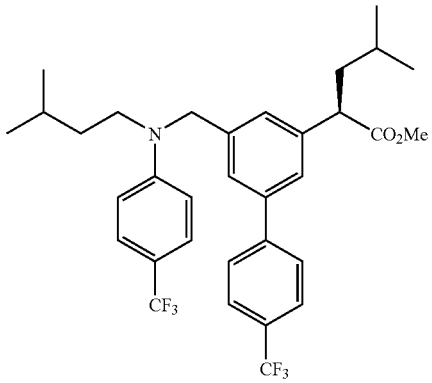

To a solution of compound 63c (0.1270 g, 0.280 mmole) in 2 mL of anhydrous toluene in a sealed tube was added 1-bromo-4-trifluoromethylbenzene (0.069 g, 0.040 mL, 0.308 mmole). The resulting solution was degassed with argon for 5 minutes, and then tris(dibenzylideneacetone)dipalladium(0) (Pd$_2$dba$_3$) (0.0026 g, 0.0028 mmole) and (±)-2,2'-bis(diphenylphosphino)-1,1'-binaphthalene (BINAP) (0.0052 g, 0.0084 mmole) were added. The mixture was degassed again with argon for 5 min, and then NaOt-Bu (0.038 g, 0.392 mmole) was added. The sealed tube was capped, and added to a preheated oil bath at 110° C. The tube was heated for 22 h. After cooling, dichloromethane and water were added to the reaction mixture. The layers were separated, and the aqueous layer was extracted twice with dichloromethane. The organic extracts were combined, washed with brine, dried (Na$_2$SO$_4$), and concentrated to provide 0.13 g of a golden brown oil. The oil was purified twice on a silica gel flash column with 2:1 heptanes:ethyl acetate as eluant, but the isolated material contained a close-running impurity. Repurification on a silica gel flash column with 3:1 heptanes:ethyl acetate yielded 0.03 g of 4-methyl-2-(5-{[(3-methyl-butyl)-(4-trifluoromethyl-phenyl)-amino]-methyl}-4'-trifluoromethyl-biphenyl-3-yl)-pentanoic acid methyl ester as a milky glass as well as some impure product containing fractions. The impure material was repurified on flash silica gel using pure dichloromethane as eluant to yield an additional 0.02 g of 4-methyl-2-(5-{[(3-methyl-butyl)-(4-trifluoromethyl-phenyl)-amino]-methyl}-4'-trifluoromethyl-biphenyl-3-yl)-pentanoic acid methyl ester. Both materials contained ca. 25% of the corresponding ethyl ester.

MH$^+$ 594.3

$^1$H NMR (300 MHz, CDCl$_3$): δ0.88 (d, J=6.6 Hz, 6H), 0.97 (d, J=6.2 Hz, 6H), 1.38-1.49 (br m, 1H), 1.52-1.73 (br m, 4H), 1.89-2.02 (br m, 1H), 3.48 (br t, J=7.9 Hz, 2H), 3.63 (s, 3H), 3.70 (br t, J=7.7 Hz, 1H), 4.62 (br s, 2H), 6.67 (br d, J=8.8 Hz, 2H), 7.15 (br s, 1H), 7.28 (br s, 1H), 7.39 (br d, J=9.2 Hz, 2H), 7.41 (br s, 1H), 7.61 (br d, J=8.3 Hz, 2H), 7.67 (br d, J=8.4 Hz, 2H).

e) 4-Methyl-2-(5-{[(3-methyl-butyl)-(4-trifluoromethyl-phenyl)-amino]-methyl}-4'-trifluoromethyl-biphenyl-3-yl)-pentanoic acid Using the procedure described for the preparation of compound 54e, compound 63d was converted to 4-methyl-2-(5-{[(3-methyl-butyl)-(4-trifluoromethyl-phenyl)-amino]-methyl}-4'-trifluoromethyl-biphenyl-3-yl)-pentanoic acid as a colorless glass.

MH$^+$ 580.3

$^1$H NMR (300 MHz, CDCl$_3$): δ0.90 (d, J=6.6 Hz, 6H), 0.95 (d, J=6.2 Hz, 6H), 1.37-1.78 (m, 5H), 1.89-2.03 (m, 1H), 3.47 (br t, J=7.8 Hz, 2H), 3.71 (t, J=7.8 Hz, 1H), 4.61 (br s, 2H), 6.65 (br d, J=8.7 Hz, 2H), 7.18 (br s, 1H), 7.29 (br s, 1H), 7.39 (br d, J=8.8 Hz, 2H), 7.43 (br s, 1H), 7.59 (d, J=8.4 Hz, 2H), 7.66 (d, J=9.2 Hz, 2H).

Screening of the Compounds of the Invention for γ-Secretase-Modulating Activity

Screening was carried out using SKNBE2 cells carrying the APP 695—wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

Examples of the γ-secretase modulating activity of representative products of the invention are shown in the following table.

| Compound # | Structure | Chemical Name | EC$_{50}$ (μM) |
|---|---|---|---|
| 1 | 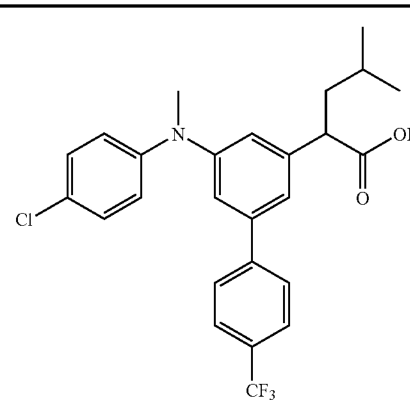 | 2-{5-[(4-Chloro-phenyl)-methyl-amino]-4'-trifluoromethyl-biphenyl-3-yl}-4-methyl-pentanoic acid | 0.62 |

-continued

| Compound # | Structure | Chemical Name | EC$_{50}$ (μM) |
|---|---|---|---|
| 2 | 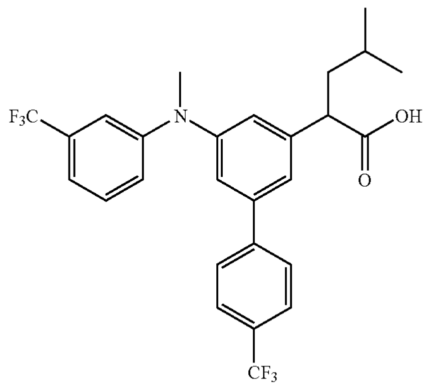 | 4-Methyl-2-{5-[methyl-(3-trifluoromethyl-phenyl)-amino]-4'-trifluoromethyl-biphenyl-3-yl}-pentanoic acid | 0.22 |
| 3 | 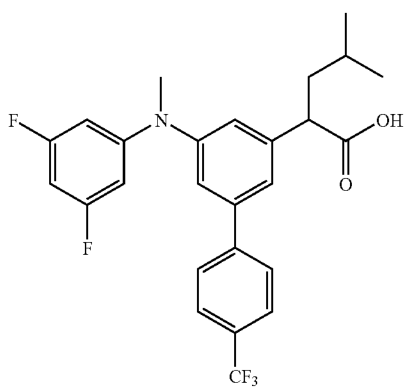 | 2-{5-[(3,5-Difluoro-phenyl)-methyl-amino]-4'-trifluoromethyl-biphenyl-3-yl}-4-methyl-pentanoic acid | 0.45 |
| 4 | 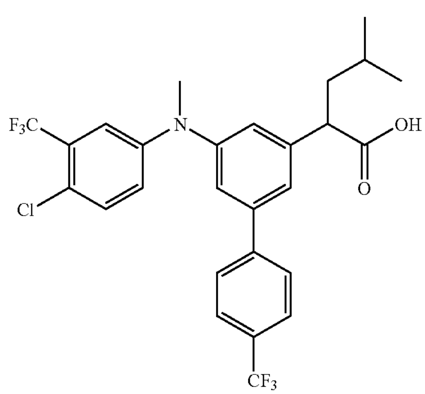 | 2-{5-[(4-Chloro-3-trifluoromethyl-phenyl)-methyl-amino]-4'-trifluoromethyl-biphenyl-3-yl}-4-methyl-pentanoic acid | 31% inhibition @ 0.3 μM |
| 5 | 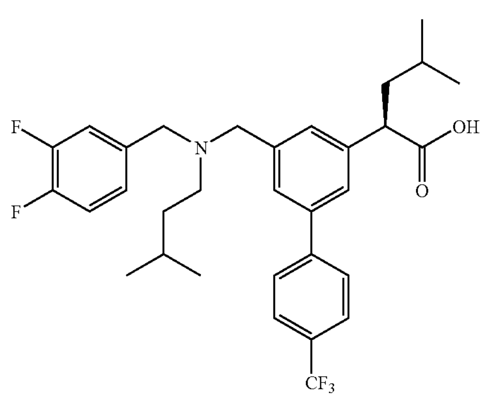 | 2-(5-{[(3,4-Difluoro-benzyl)-(3-methyl-butyl)-amino]-methyl}-4'-trifluoromethyl-biphenyl-3-yl)-4-methyl-pentanoic acid | 0.065 |

| Compound # | Structure | Chemical Name | EC₅₀ (μM) |
|---|---|---|---|
| 6 | 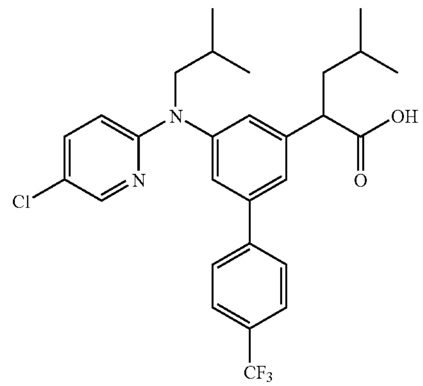 | 2-{5-[(5-Chloro-pyridin-2-yl)-isobutyl-amino]-4'-trifluoromethyl-biphenyl-3-yl}-4-methyl-pentanoic acid | 0.21 |
| 7 | 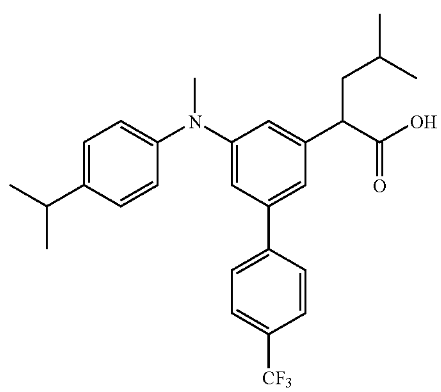 | 2-{5-[(4-Isopropyl-phenyl)-methyl-amino]-4'-trifluoromethyl-biphenyl-3-yl}-4-methyl-pentanoic acid | 8% |
| 8 | 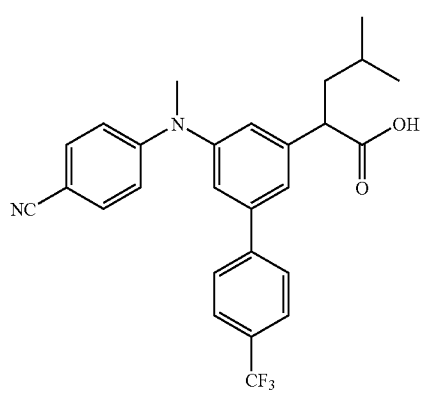 | 2-{5-[(4-Cyano-phenyl)-methyl-amino]-4'-trifluoromethyl-biphenyl-3-yl}-4-methyl-pentanoic acid | −0% |
| 9 | 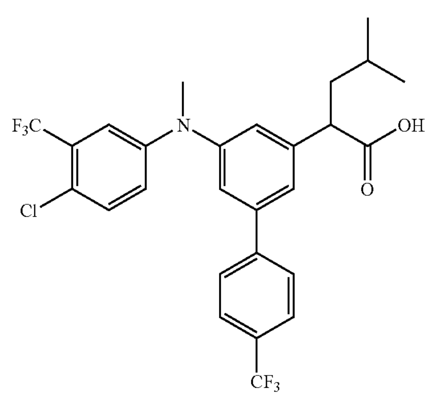 | 2-{5-[(4-Chloro-3-trifluoromethyl-phenyl)-methyl-amino]-4'-trifluoromethyl-biphenyl-3-yl}-4-methyl-pentanoic acid | 0.33 |

| Compound # | Structure | Chemical Name | EC$_{50}$ (μM) |
|---|---|---|---|
| 10 | 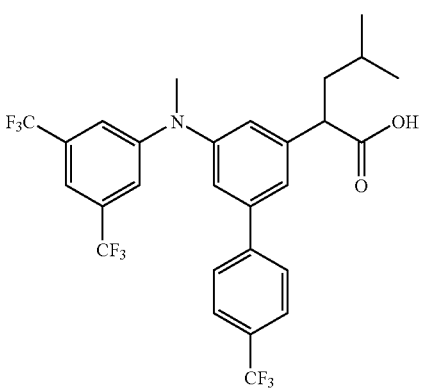 | 2-{5-[(3,5-Bis-trifluoromethyl-phenyl)-methyl-amino]-4'-trifluoromethyl-biphenyl-3-yl}-4-methyl-pentanoic acid | 0.19 |
| 11 | 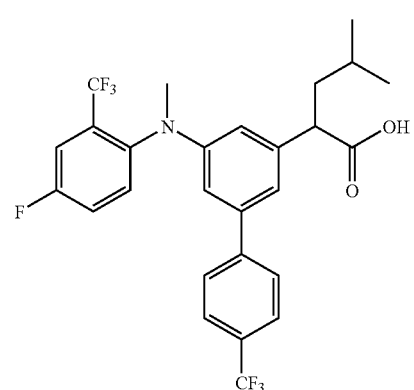 | 2-{5-[(4-Fluoro-2-trifluoromethyl-phenyl)-methyl-amino]-4'-trifluoromethyl-biphenyl-3-yl}-4-methyl-pentanoic acid | 23% inhibition @ 0.3 μM |
| 12 | 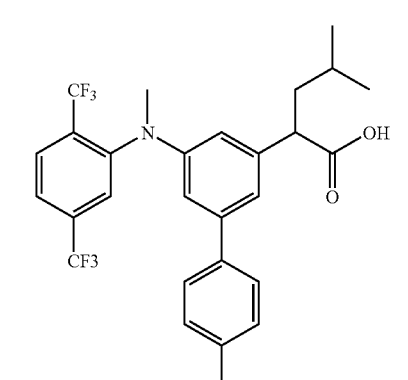 | 2-{5-[(2,5-Bis-trifluoromethyl-phenyl)-methyl-amino]-4'-trifluoromethyl-biphenyl-3-yl}-4-methyl-pentanoic acid | 0.16 |
| 13 | 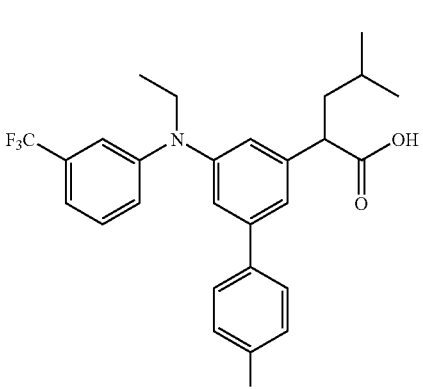 | 2-{5-[Ethyl-(3-trifluoromethyl-phenyl)-amino]-4'-trifluoromethyl-biphenyl-3-yl}-4-methyl-pentanoic acid | 16% inhibition @ 0.3 μM |

| Compound # | Structure | Chemical Name | EC$_{50}$ (μM) |
|---|---|---|---|
| 14 | 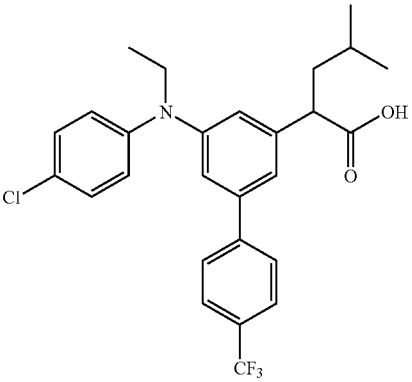 | 2-{5-[(4-Chloro-phenyl)-ethyl-amino]-4'-trifluoromethyl-biphenyl-3-yl}-4-methyl-pentanoic acid | 14% inhibition @ 0.3 μM |
| 15 | 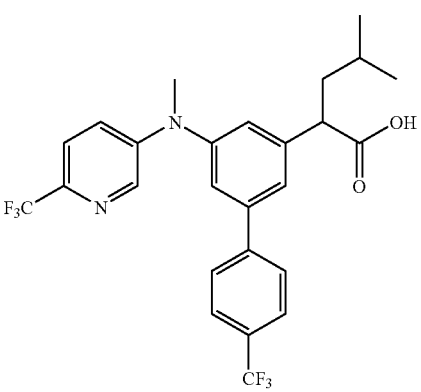 | 4-Methyl-2-{5-[methyl-(6-trifluoromethyl-pyridin-3-yl)-amino]-4'-trifluoromethyl-biphenyl-3-yl}-pentanoic acid | 0.85 |
| 16 | 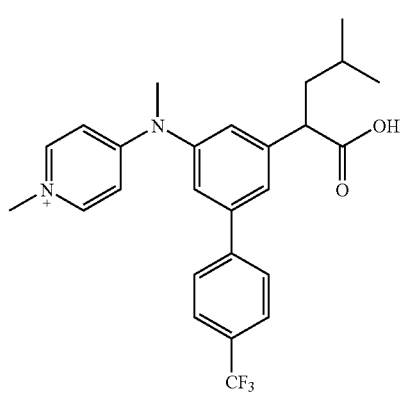 | 4-Methyl-2-{5-[methyl-(1-methyl-pyridin-4-yl)-amino]-4'-trifluoromethyl-biphenyl-3-yl}-pentanoic acid | 13% inhibition @ 0.3 μM |
| 17 | 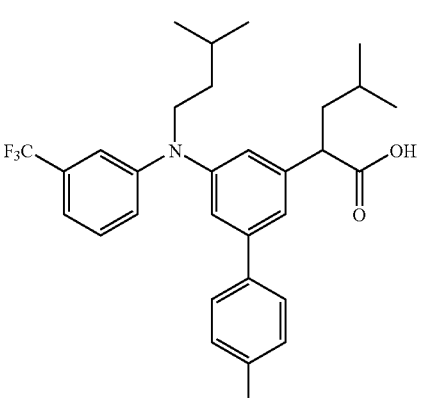 | 4-Methyl-2-{5-[(3-methyl-butyl)-(4-trifluoromethyl-phenyl)-amino]-4'-trifluoromethyl-biphenyl-3-yl}-pentanoic acid | 0.26 |

-continued

| Compound # | Structure | Chemical Name | EC$_{50}$ (μM) |
|---|---|---|---|
| 18 | 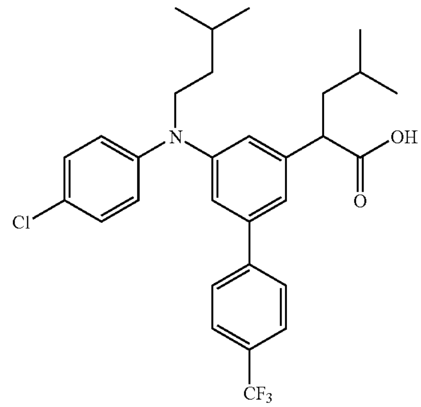 | 2-{5-[(4-Chloro-phenyl)-methyl-amino]-4'-trifluoromethyl-biphenyl-3-yl}-4-methyl-pentanoic acid | 0.15 |
| 19 | 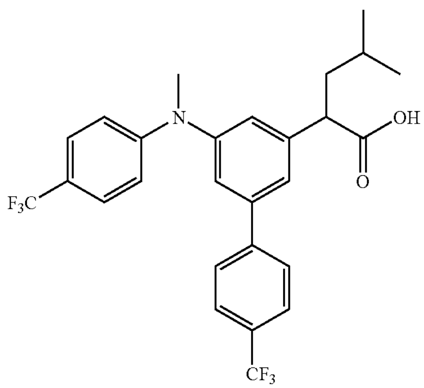 | 4-Methyl-2-{5-[methyl-(4-trifluoromethyl-phenyl)-amino]-4'-trifluoromethyl-biphenyl-3-yl}-pentanoic acid | 22% inhibition @ 0.3 μM |
| 20 | 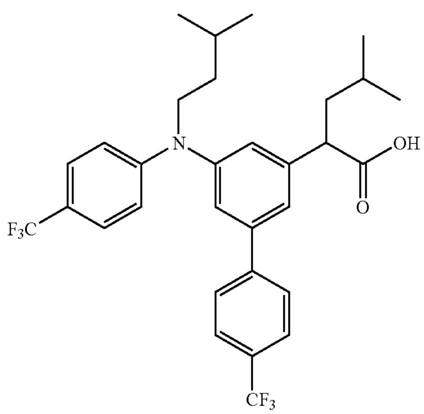 | 4-Methyl-2-{5-[(3-methyl-butyl)-(4-trifluoromethyl-phenyl)-amino]-4'-trifluoromethyl-biphenyl-3-yl}-pentanoic acid | 0.17 |
| 21 | 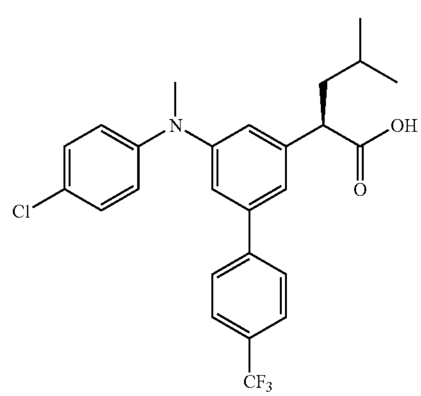 | (R*)-2-{5-[(4-Chloro-phenyl)-methyl-amino]-4'-trifluoromethyl-biphenyl-3-yl}-4-methyl-pentanoic acid | 1.13 |

| Compound # | Structure | Chemical Name | EC$_{50}$ (μM) |
|---|---|---|---|
| 22 | 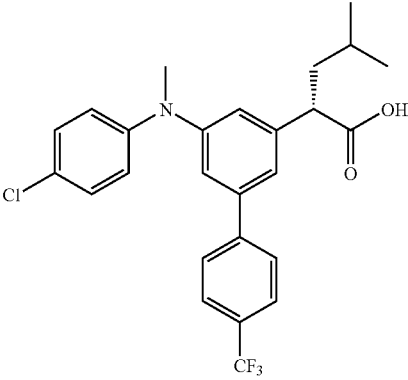 | (S*)-2-{5-[(4-Chloro-phenyl)-methyl-amino]-4'-trifluoromethyl-biphenyl-3-yl}-4-methyl-pentanoic acid | 2.15 |
| 23 | 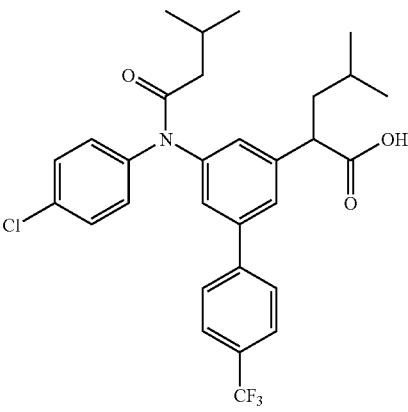 | 2-{5-[(4-Chloro-phenyl)-(3-methyl-butyryl)-amino]-4'-trifluoromethyl-biphenyl-3-yl}-4-methyl-pentanoic acid | 21% inhibition @ 0.3 μM |
| 24 | 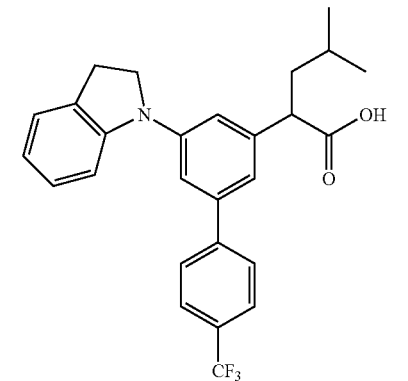 | 2-[5-(2,3-Dihydro-indol-1-yl)-4'-trifluoromethyl-biphenyl-3-yl]-4-methyl-pentanoic acid | 0% inhibition @ 0.3 μM |
| 25 | 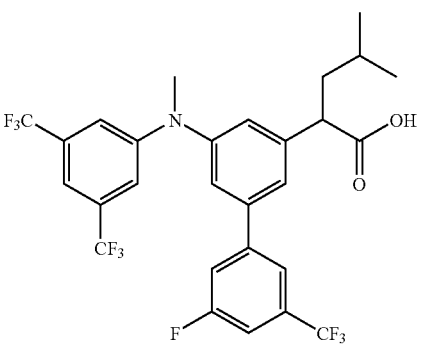 | 2-{5-[(3,5-Bis-trifluoromethyl-phenyl)-methyl-amino]-3'-fluoro-5'-trifluoromethyl-biphenyl-3-yl}-4-methyl-pentanoic acid | 0.6 |

| Compound # | Structure | Chemical Name | EC$_{50}$ (µM) |
| --- | --- | --- | --- |
| 26 | 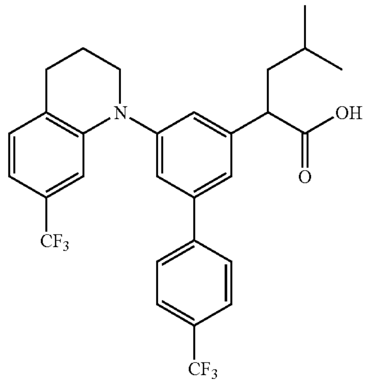 | 4-Methyl-2-[4'-trifluoromethyl-5-(7-trifluoromethyl-3,4-dihydro-2H-quinolin-1-yl)-biphenyl-3-yl]-pentanoic acid | 0.36 |
| 27 | 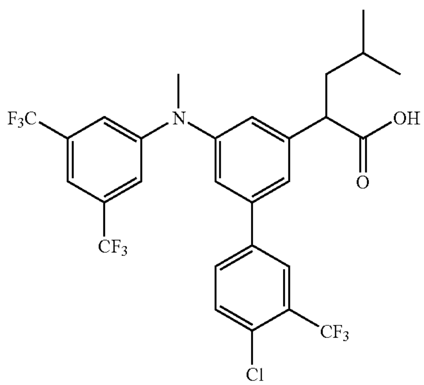 | 2-{5-[(3,5-Bis-trifluoromethyl-phenyl)-methyl-amino]-4'-chloro-3'-trifluoromethyl-biphenyl-3-yl}-4-methyl-pentanoic acid | 0.48 |
| 28 | 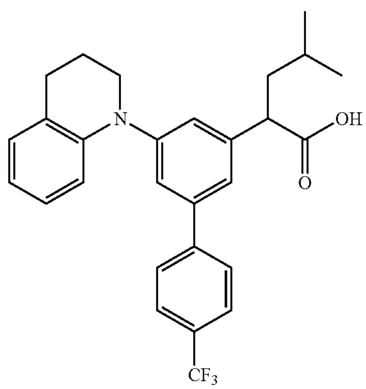 | 2-[5-(3,4-Dihydro-2H-quinolin-1-yl)-4'-trifluoromethyl-biphenyl-3-yl]-4-methyl-pentanoic acid | 0% inhibition @ 0.3 µM |
| 29 | 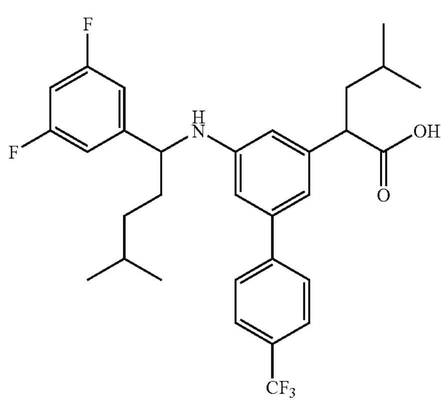 | 2-{5-[1-(3,5-Difluoro-phenyl)-4-methyl-pentylamino]-4'-trifluoromethyl-biphenyl-3-yl}-4-methyl-pentanoic acid | 0.3 |

-continued

| Compound # | Structure | Chemical Name | EC$_{50}$ (μM) |
|---|---|---|---|
| 30 | 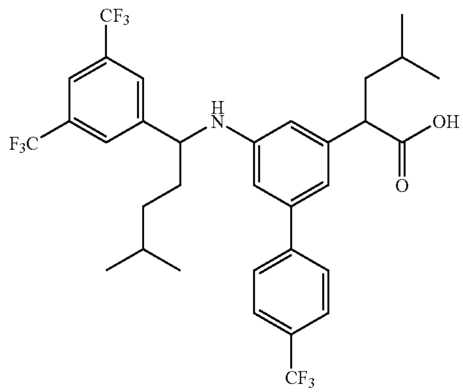 | 2-{5-[1-(3,5-Bis-trifluoromethyl-phenyl)-4-methyl-pentylamino]-4'-trifluoromethyl-biphenyl-3-yl}-4-methyl-pentanoic acid | 0.22 |
| 31 | 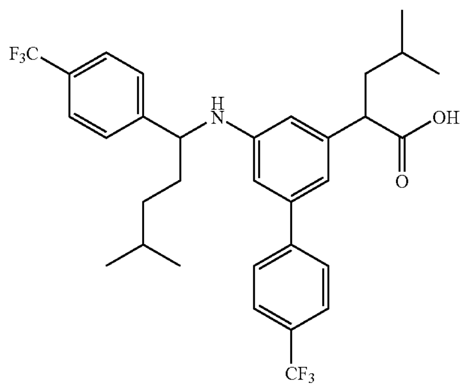 | 4-Methyl-2-{5-[4-methyl-1-(4-trifluoromethyl-phenyl)-pentylamino]-4'-trifluoromethyl-biphenyl-3-yl}-pentanoic acid | 0.27 |
| 32 | 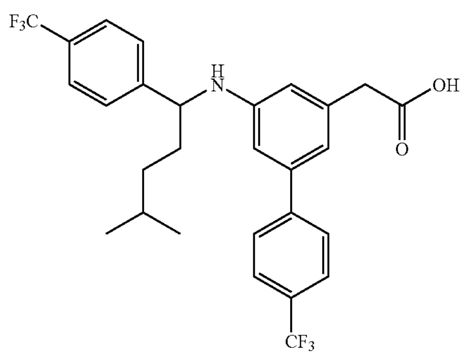 | 5-[4-Methyl-1-(4-trifluoromethyl-phenyl)-pentylamino]-4'-trifluoromethyl-biphenyl-3-yl}-acetic acid | 25% inhibition @ 0.3 μM |
| 33 | 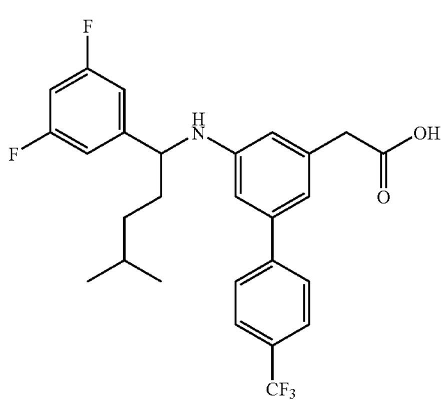 | 5-[1-(3,5-Difluoro-phenyl)-4-methyl-pentylamino]-4'-trifluoromethyl-biphenyl-3-yl}-acetic acid | 11% inhibition @ 0.3 μM |

-continued

| Compound # | Structure | Chemical Name | EC$_{50}$ (μM) |
|---|---|---|---|
| 34 | 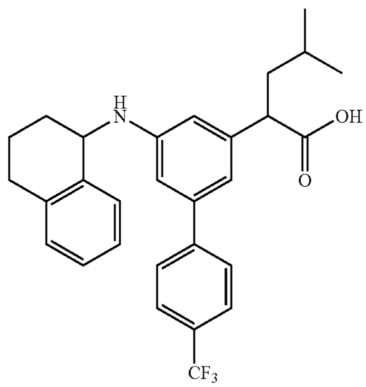 | 4-Methyl-2-[5-(1,2,3,4-tetrahydro-naphthalen-1-ylamino)-4'-trifluoromethyl-biphenyl-3-yl]-pentanoic acid | 22% inhibition @ 0.3 μM |
| 35 | 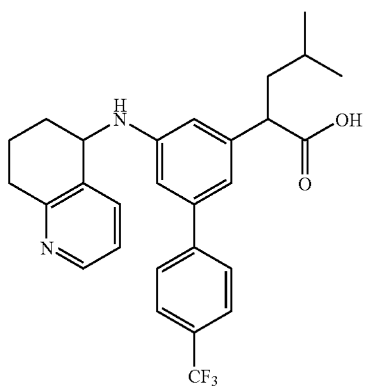 | 4-Methyl-2-[5-(5,6,7,8-tetrahydro-isoquinolin-5-ylamino)-4'-trifluoromethyl-biphenyl-3-yl]-pentanoic acid | 5% inhibition @ 0.3 μM |
| 36 | 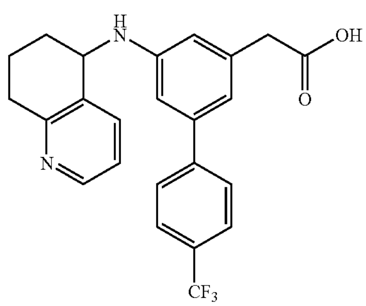 | [5-(5,6,7,8-Tetrahydro-isoquinolin-5-ylamino)-4'-trifluoromethyl-biphenyl-3-yl]-acetic acid | 0% inhibition @ 0.3 μM |
| 37 | 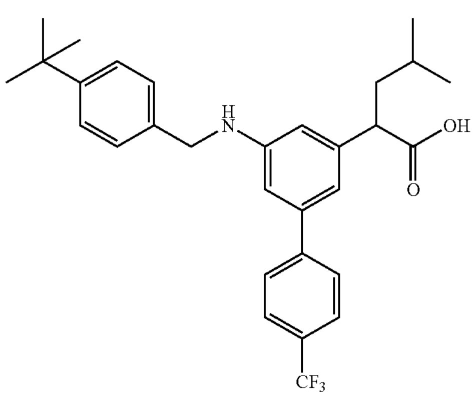 | 2-[5-(4-tert-Butyl-benzylamino)-4'-trifluoromethyl-biphenyl-3-yl]-4-methyl-pentanoic acid | 18% inhibition @ 0.3 μM |

-continued

| Compound # | Structure | Chemical Name | EC$_{50}$ (μM) |
|---|---|---|---|
| 38 | 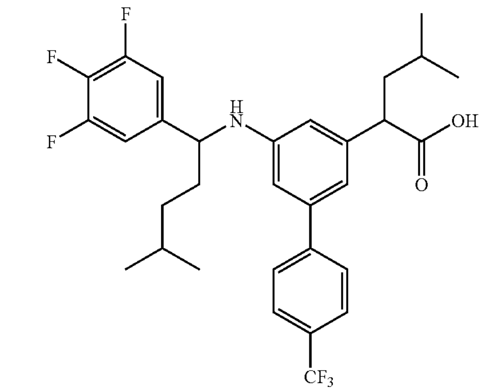 | 4-Methyl-2-{5-[4-methyl-1-(3,4,5-trifluoro-phenyl)-pentylamino]-4'-trifluoromethyl-biphenyl-3-yl}-pentanoic acid | 0.23 |
| 39 | 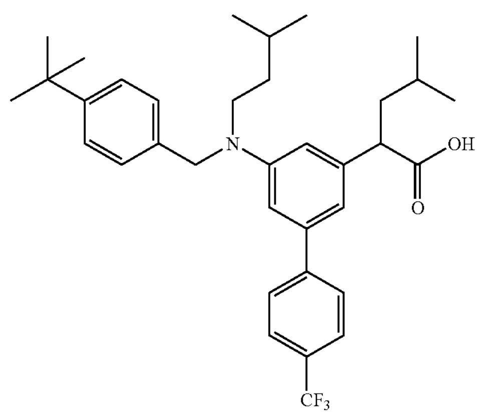 | 2-{5-[(4-tert-Butyl-benzyl)-(3-methyl-butyl)-amino]-4'-trifluoromethyl-biphenyl-3-yl}-4-methyl-pentanoic acid | 0.58 |
| 40 | 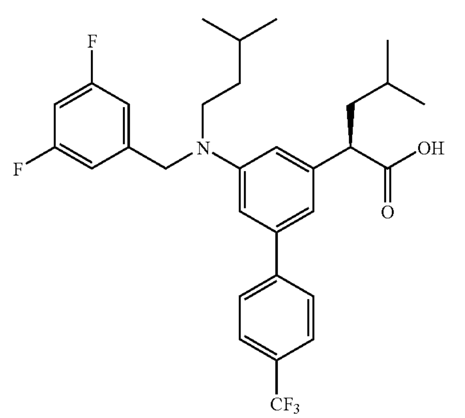 | 2-{5-[(3,5-Difluoro-benzyl)-(3-methyl-butyl)-amino]-4'-trifluoromethyl-biphenyl-3-yl}-4-methyl-pentanoic acid | 0.19 |
| 41 | 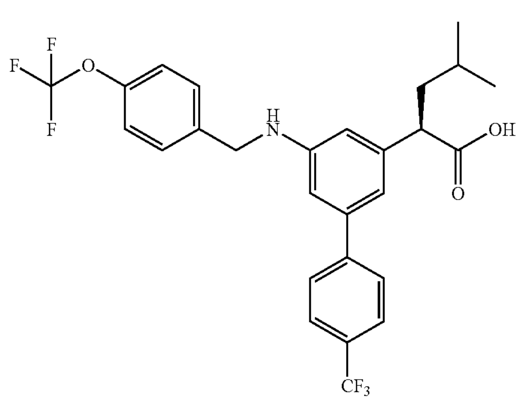 | 4-Methyl-2-[5-(4-trifluoromethoxy-benzylamino)-4'-trifluoromethyl-biphenyl-3-yl]-pentanoic acid | 0% inhibition @ 0.3 μM |

-continued

| Compound # | Structure | Chemical Name | EC$_{50}$ (μM) |
|---|---|---|---|
| 42 | 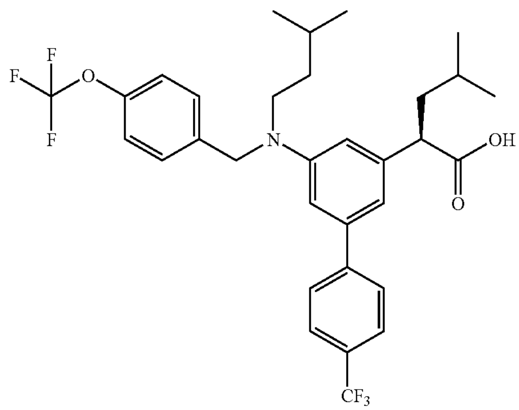 | 4-Methyl-2-{5-[(3-methyl-butyl)-(4-trifluoromethoxy-benzyl)-amino]-4'-trifluoromethyl-biphenyl-3-yl}-pentanoic acid | 0.64 |
| 43 | 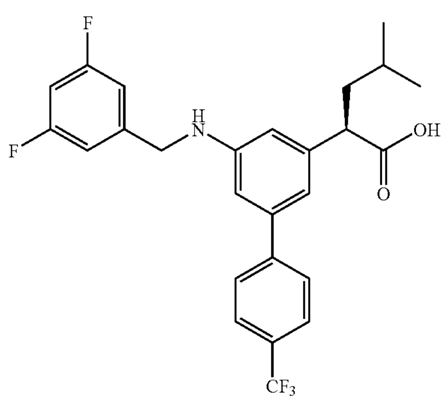 | 2-[5-(3,5-Difluoro-benzylamino)-4'-trifluoromethyl-biphenyl-3-yl]-4-methyl-pentanoic acid | 0% inhibition @ 0.3 μM |
| 44 | 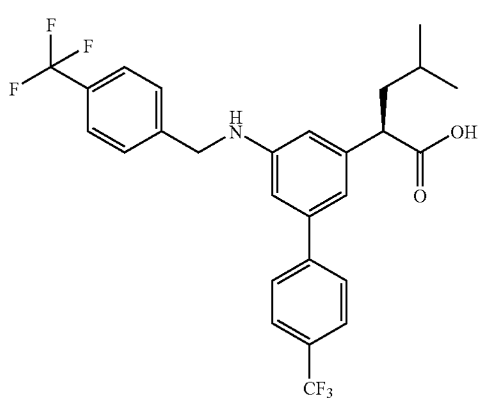 | 4-Methyl-2-[4'-trifluoromethyl-5-(4-trifluoromethyl-benzylamino)-biphenyl-3-yl]-pentanoic acid | 7% inhibition @ 0.3 μM |

| Compound # | Structure | Chemical Name | EC$_{50}$ (μM) |
|---|---|---|---|
| 45 | 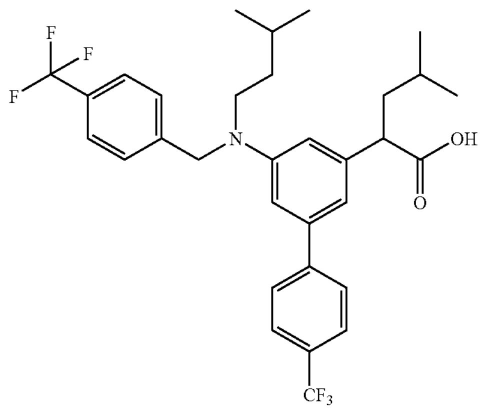 | 4-Methyl-2-{5-[(3-methyl-butyl)-(4-trifluoromethyl-benzyl)-amino]-4'-trifluoromethyl-biphenyl-3-yl}-pentanoic acid | 0.58 |
| 46 | 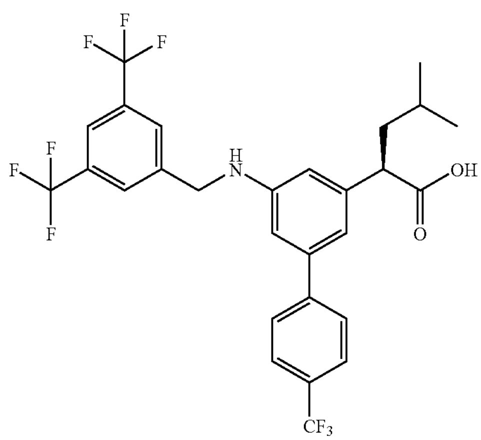 | 2-[5-(3,5-Bis-trifluoromethyl-benzylamino)-4'-trifluoromethyl-biphenyl-3-yl]-4-methyl-pentanoic acid | 6% inhibition @ 0.3 μM |
| 47 | 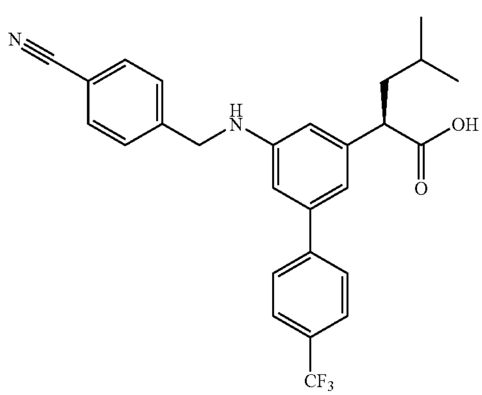 | 2-[5-(4-Cyano-benzylamino)-4'-trifluoromethyl-biphenyl-3-yl]-4-methyl-pentanoic acid | 0% inhibition @ 0.3 μM |

| Compound # | Structure | Chemical Name | EC$_{50}$ (μM) |
|---|---|---|---|
| 48 | 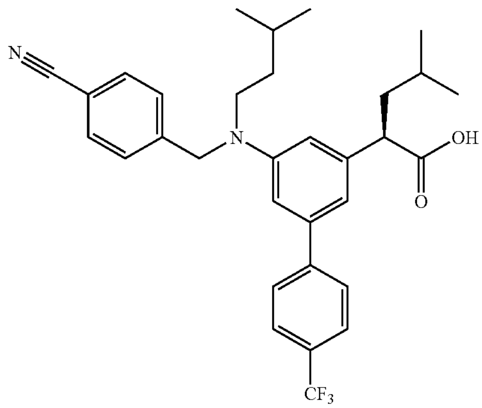 | 2-{5-[(4-Cyano-benzyl)-(3-methyl-butyl)-amino]-4'-trifluoromethyl-biphenyl-3-yl}-4-methyl-pentanoic acid | 31% inhibition @ 0.3 μM |
| 49 | 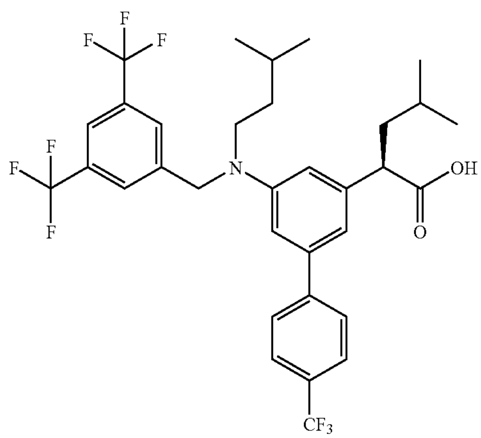 | 2-{5-[(3,5-Bis-trifluoromethyl-benzyl)-(3-methyl-butyl)-amino]-4'-trifluoromethyl-biphenyl-3-yl}-4-methyl-pentanoic acid | 0.22 |
| 50 | 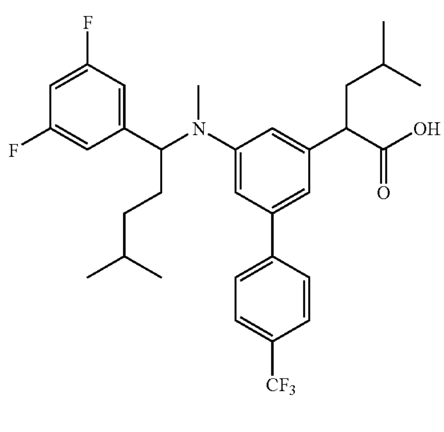 | 2-(5-{[1-(3,5-Difluoro-phenyl)-4-methyl-pentyl]-methyl-amino}-4'-trifluoromethyl-biphenyl-3-yl)-4-methyl-pentanoic acid | 65% inhibition @ 0.3 μM |

-continued

| Compound # | Structure | Chemical Name | EC$_{50}$ (μM) |
|---|---|---|---|
| 51 | 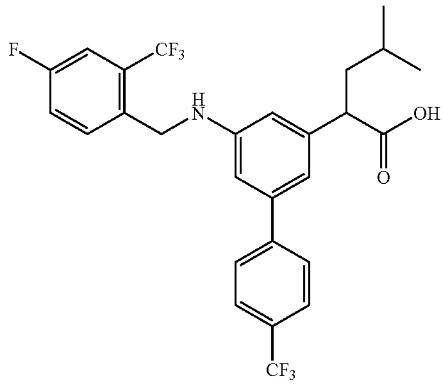 | 2-[5-(4-Fluoro-2-trifluoromethyl-benzylamino)-4'-trifluoromethyl-biphenyl-3-yl]-4-methyl-pentanoic acid | 0.64 |
| 52 | 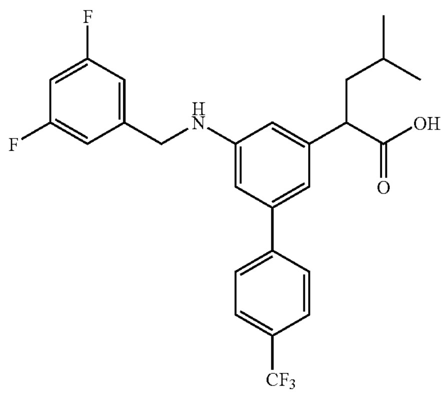 | 2-[5-(3,5-Difluoro-benzylamino)-4'-trifluoromethyl-biphenyl-3-yl]-4-methyl-pentanoic acid | 0% inhibition @ 0.3 μM |
| 53 | 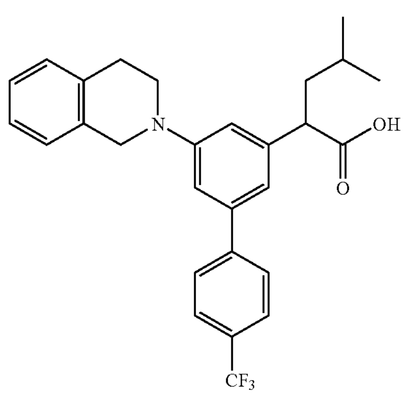 | 2-[5-(3,4-Dihydro-1H-isoquinolin-2-yl)-4'-trifluoromethyl-biphenyl-3-yl]-4-methyl-pentanoic acid | 0% inhibition @ 0.3 μM |
| 54 | 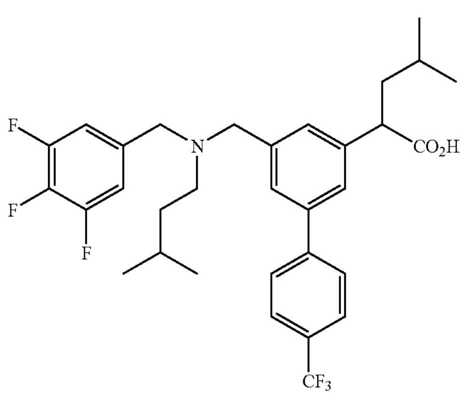 | 4-Methyl-2-(5-{[(3-methyl-butyl)-(3,4,5-trifluoro-benzyl)-amino]-methyl}-4'-trifluoromethyl-biphenyl-3-yl)-pentanoic acid | 0.27 |

| Compound # | Structure | Chemical Name | EC$_{50}$ (μM) |
|---|---|---|---|
| 55 | 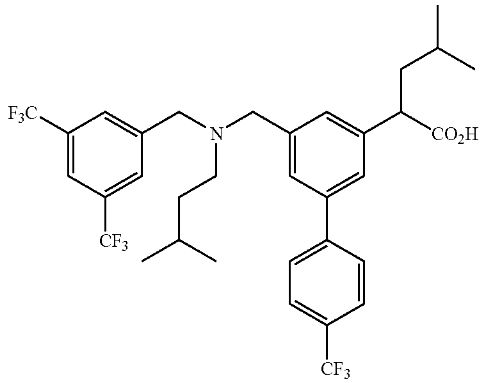 | 2-(5-{[(3,5-Bis-trifluoromethyl-benzyl)-(3-methyl-butyl)-amino]-methyl}-4'-trifluoromethyl-biphenyl-3-yl)-4-methyl-pentanoic acid | 025 |
| 56 | 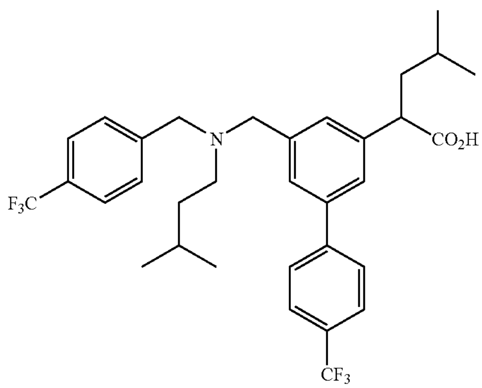 | 4-Methyl-2-(5-{[(3-methyl-butyl)-(4-trifluoromethyl-benzyl)amino]-methyl}-4'-trifluoromethyl-biphenyl-3-yl)-pentanoic acid | 0.22 |
| 57 | 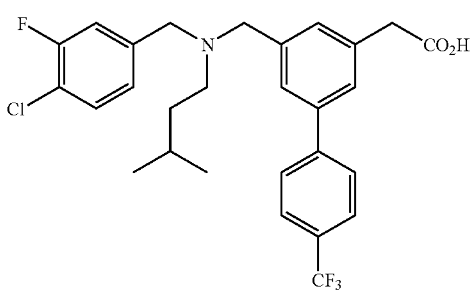 | (5-{[(4-Chloro-3-fluoro-benzyl)-(3-methyl-butyl)-amino]-methyl}-4'-trifluoromethyl-biphenyl-3-yl)-acetic acid | 11% inhibition @ 0.3 uM |
| 58 | 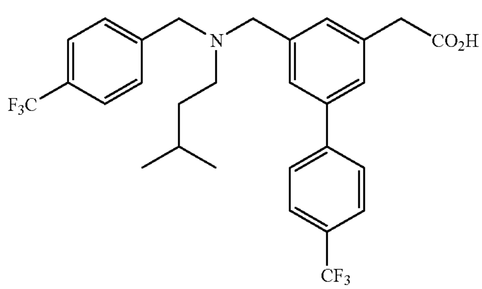 | (5-{[(3-Methyl-butyl)-(4-trifluoromethyl-benzyl)-amino]-methyl}-4'-trifluoromethyl-biphenyl-3-yl)-acetic acid | 0.59 |

| Compound # | Structure | Chemical Name | EC$_{50}$ (μM) |
|---|---|---|---|
| 59 | 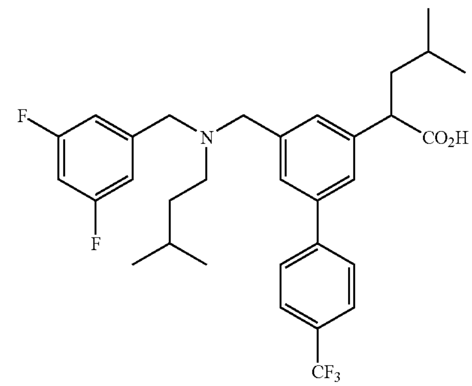 | 2-(5-{[(3,5-Difluoro-bentyl)-(3-methyl-butyl)-amino]-methyl}-4'-trifluoromethyl-biphenyl-3-yl)-4-methyl-pentanoic acid | 0.24 |
| 60 | 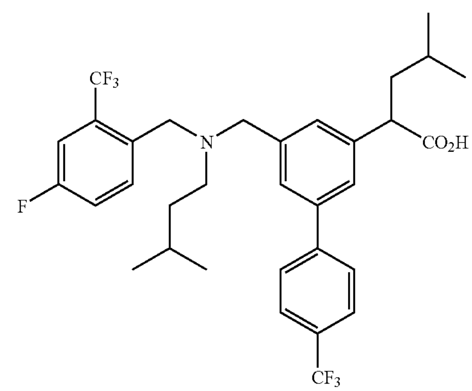 | 2-(5-{[(4-fluoro-2-trifluoromethyl-benzyl)-(3-methyl-butyl)-amino]-methyl}-4'-trifluoromethyl-biphenyl-3-yl)-4-methyl-pentanoic acid | 0.3 |
| 61 | 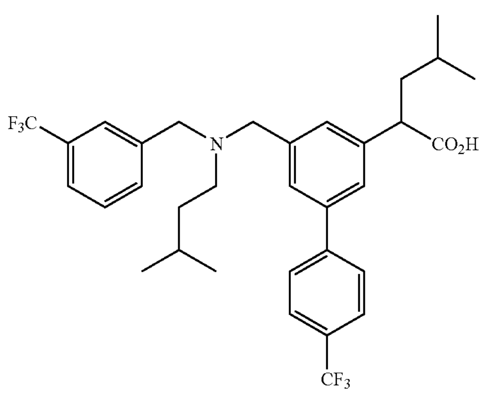 | 4-Methyl-2-(5-{[(3-methyl-butyl)-(3-trifluoromethyl-benzyl)-amino]-methyl}-4'-trifluoromethyl-biphenyl-3-yl)-pentanoic acid | 0.39 |
| 62 | 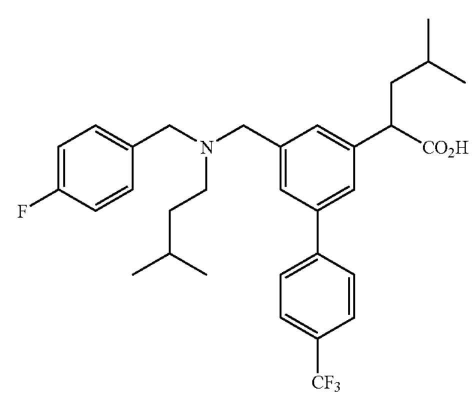 | 2-(5-{[(4-Fluoro-benzyl)-(3-methyl-butyl)-amino]-methyl}-4'-trifluoromethyl-biphenyl-3-yl)-4-methyl-pentanoic acid | 0.13 |

-continued

| Compound # | Structure | Chemical Name | EC$_{50}$ (μM) |
|---|---|---|---|
| 63 | 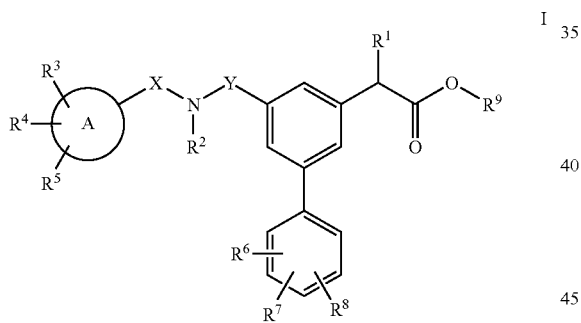 | 4-Methyl-2-(5-{[(3-methyl-butyl)-(4-trifluoromethyl-phenyl)-amino]-methyl}-4'-trifluoromethyl-biphenyl-3-yl)-pentanoic acid | 0.25 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:

1. A compound having the general Formula (I)

$$I$$

wherein (A)

A is phenyl or pyridyl;

X is $CH_2$ or $CHC_{(1-4)}$alkyl wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

$R^2$ is selected from the group consisting of H, benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I, and $CF_3$; alternatively, when $R^2$ is alkyl, it may be combined with $R^3$, the A ring, X, and the attached nitrogen to form a 9 or 10 membered fused ring system;

$R^3$, and $R^6$, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

$R^4$, $R^5$, $R^7$, and $R^8$ are independently selected from the group consisting of $CF_3$, H, F, Cl, $OCH_3$, $C_{(1-4)}alkyl$, and CN;

$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

or, (B)

A is phenyl or pyridyl;

X is $CH_2$, a direct bond, or $CHC_{(1-4)}$alkyl wherein said alkyl is optionally substituted with one, two, or three substituents independently selected from the group consisting of F, Cl, Br, I, and $CF_3$;

Y is $CH_2$ or a direct bond;

$R^1$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

R² is selected from the group consisting of benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I, and $CF_3$; alternatively, when R² is alkyl, it may be combined with R³, the A ring, X, and the attached nitrogen to form a 9 or 10 membered fused ring system;

R³, and R⁶, are independently selected from the group consisting of H, F, Cl, Br, I, CN, OH, $CF_3$, $OCF_3$, $C(O)NH_2$, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl and $C_1$-$C_4$-alkoxy;

R⁴, R⁵, R⁷, and R⁸ are independently selected from the group consisting of $CF_3$, H, F, Cl, $OCH_3$, $C_{(1-4)}alkyl$, and CN;

R⁹ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

or a pharmaceutically acceptable salt thereof.

2. A compound of claim 1 wherein

R¹ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$; and alkenyl selected from $C_2H_3$, i-$C_3H_5$, n-$C_3H_5$, n-$C_4H_7$, i-$C_4H_7$, and sec-$C_4H_7$;

R⁹ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$;

or a pharmaceutically acceptable salt thereof.

3. A compound of claim 2 wherein

R² is selected from the group consisting of H, benzyl, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $C(O)CH_2CH(CH_3)_2$; alkenyl selected from $C_2H_3$, i-$C_3H_5$, n-$C_3H_5$, n-$C_4H_7$, i-$C_4H_7$, and sec-$C_4H_7$; alternatively, when R² is alkyl, it may be combined with R³, the A ring, X, and the attached nitrogen to form a 9 or 10 membered fused ring system, or a pharmaceutically acceptable salt thereof.

4. A compound of claim 3 wherein

R³ and R⁶ are independently selected from the group consisting of $C(O)NH_2$, $OCF_3$, $CF_3$, H, F, Cl, $OCH_3$, $C_{(1-4)}alkyl$, and CN;

R⁹ is H;

or an ester or pharmaceutically acceptable salt thereof.

5. A compound of claim 4 wherein

A is phenyl or pyridyl

X is $CH_2$, a direct bond, or $CHC_{(1-5)}alkyl$;

R¹ is $CH_2CH(CH_3)_2$;

R² is H, $CH_3$, $CH_2CH_3$, $CH_2CH_2CH(CH_3)_2$, $C(O)CH_2CH(CH_3)_2$; alternatively R² and R³, together with the A ring, X, and the attached nitrogen may form a fused ring system selected from the group consisting of:

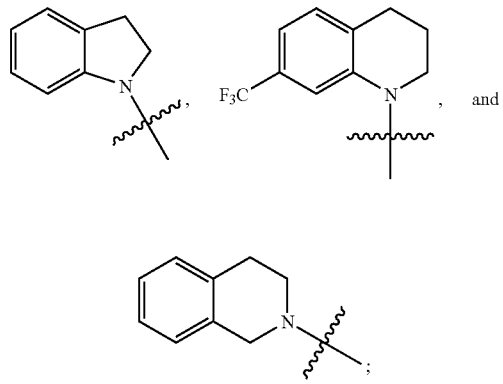

R³, R⁴, and R⁵, are H, Cl, $CF_3$, F, —CN, $C(O)NH_2$, $CH(CH_3)_2$, $CH_3$, $C(CH_3)_3$, $OCF_3$;

R⁶, R⁷, and R⁸ are H, F, Cl, and $CF_3$;

or an ester or pharmaceutically acceptable salt thereof.

6. A compound selected from the group consisting of

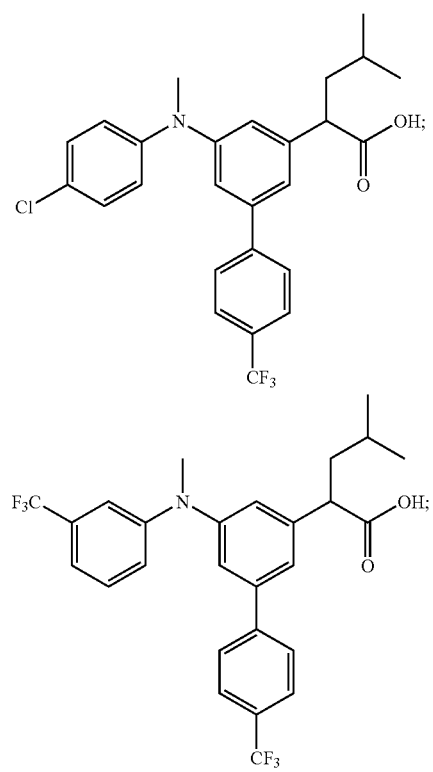

151
-continued
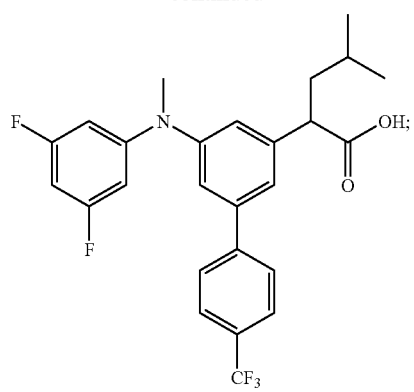
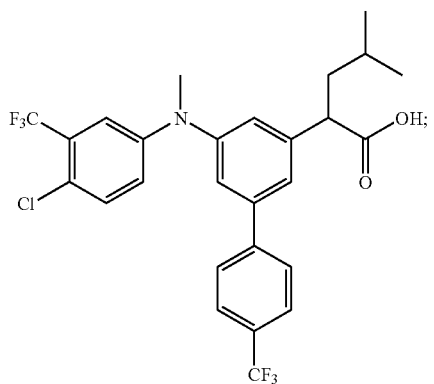
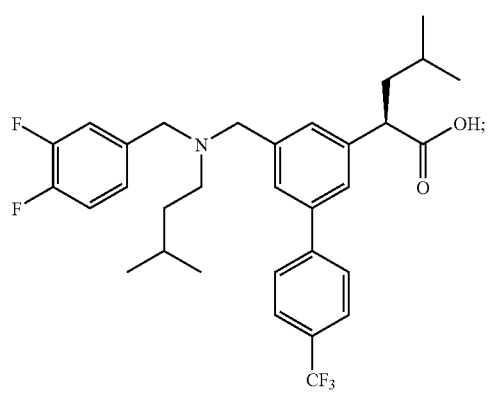
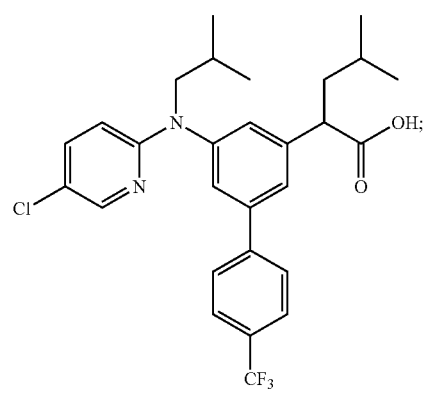
152
-continued
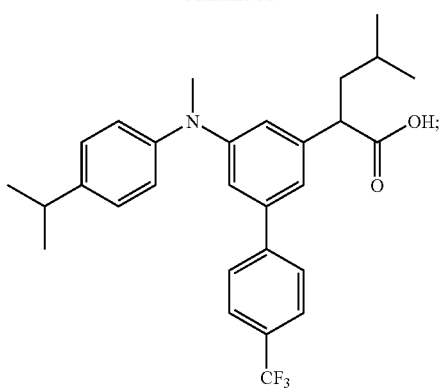
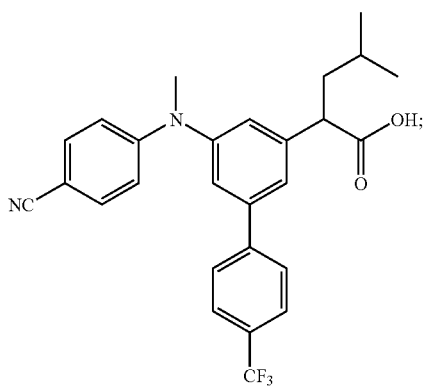
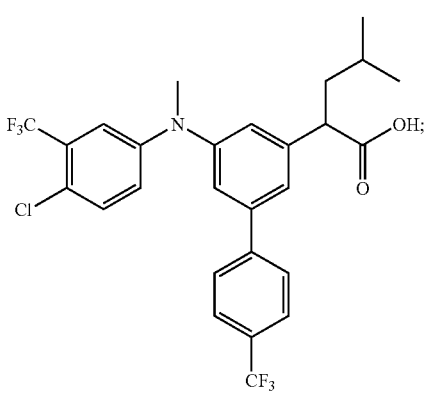
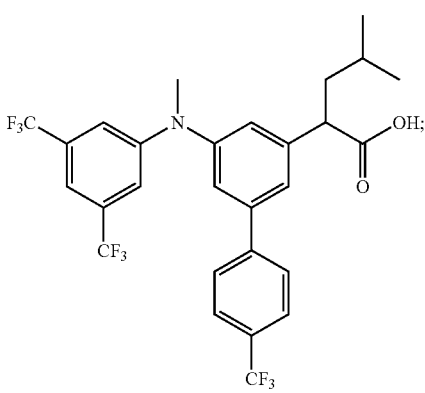

153
-continued
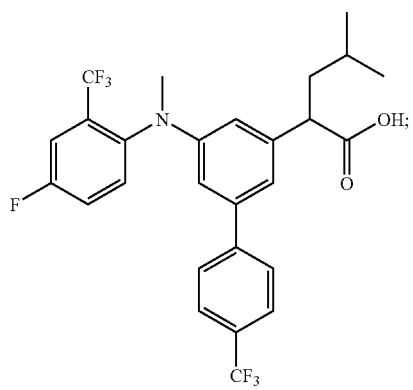
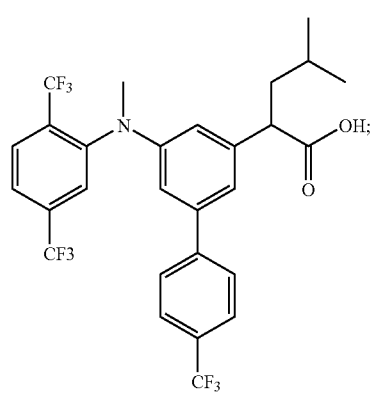
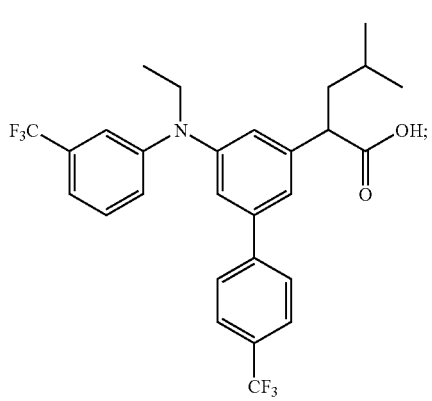
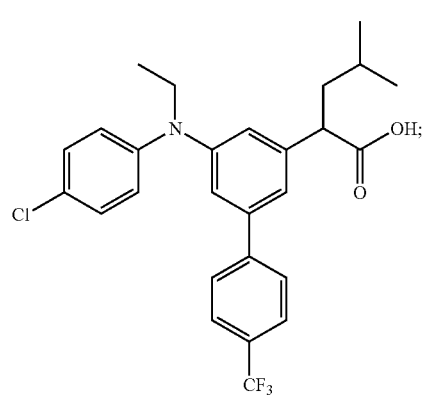
154
-continued
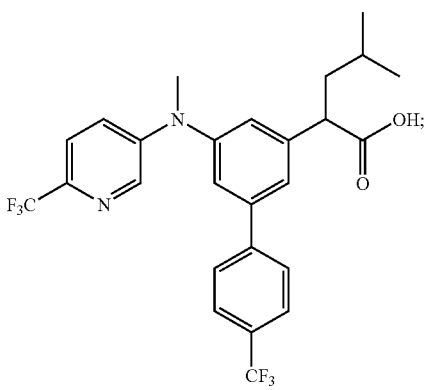
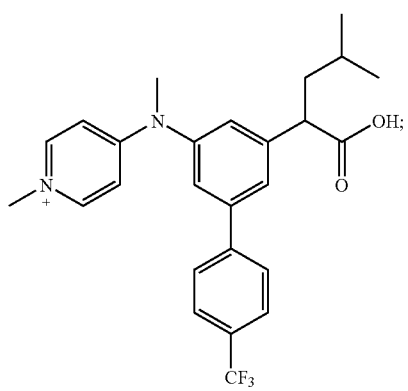
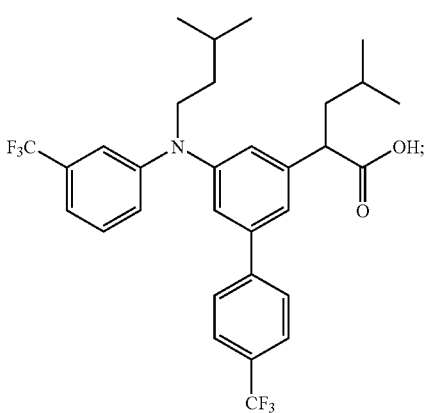
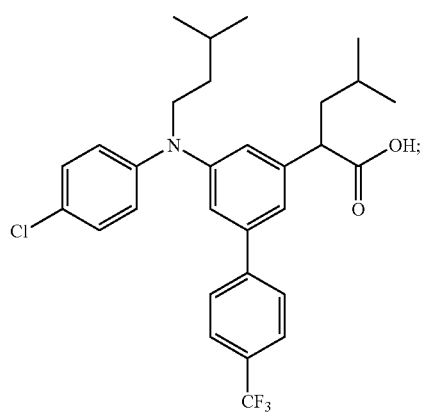

155
-continued
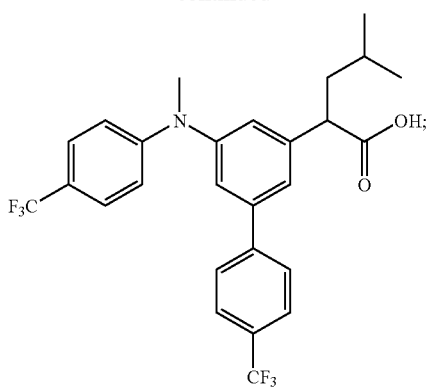
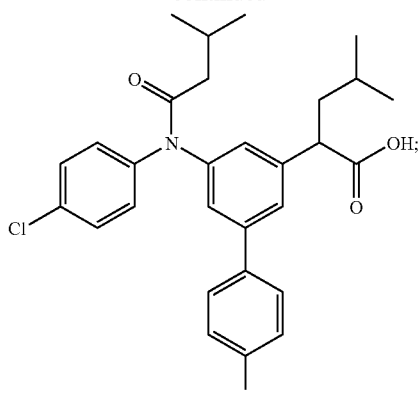
156
-continued

157
-continued
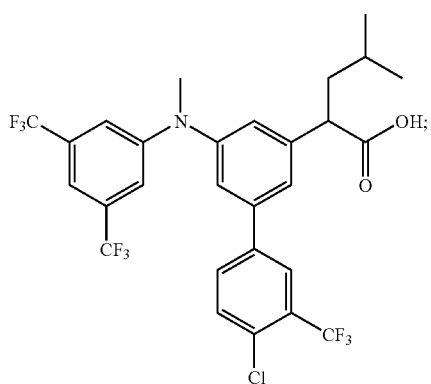
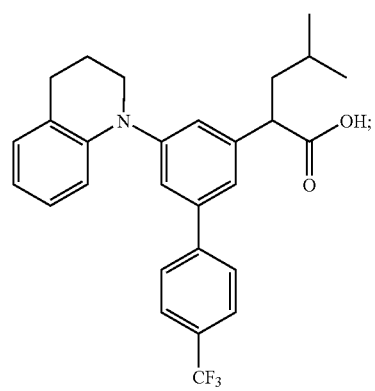
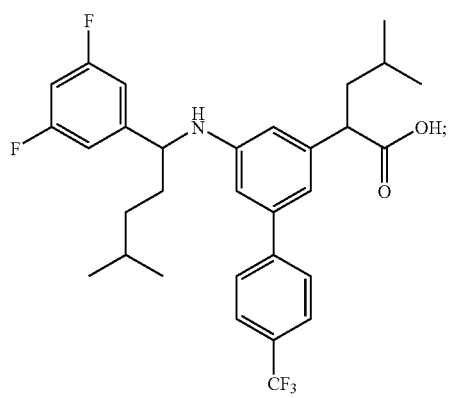
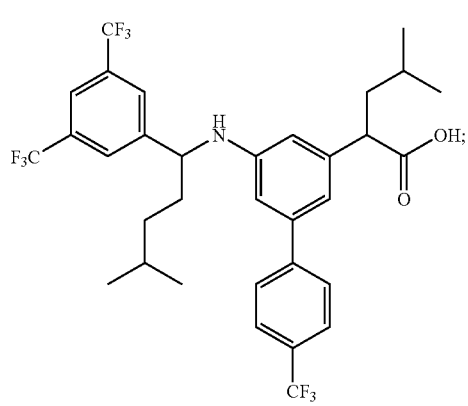
158
-continued
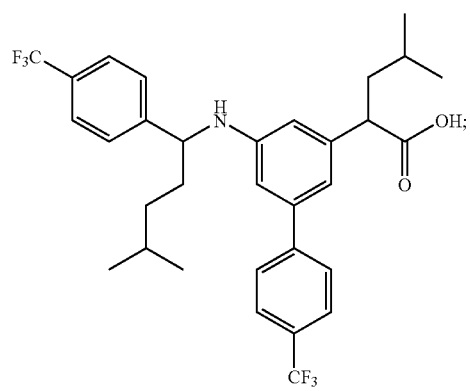
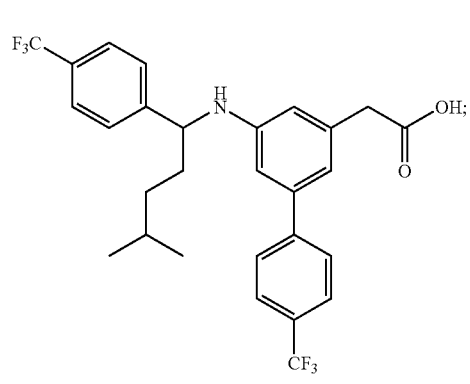
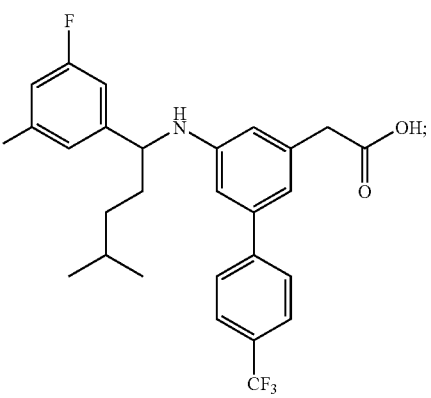
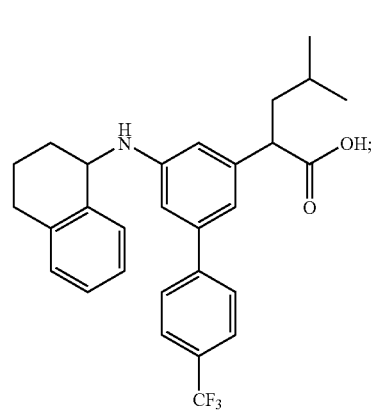

159
-continued
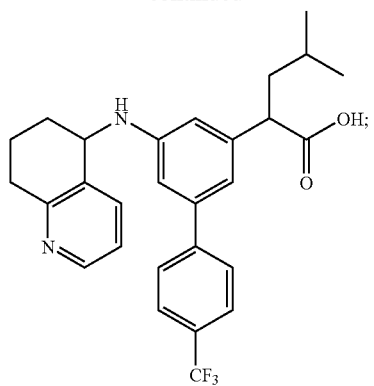
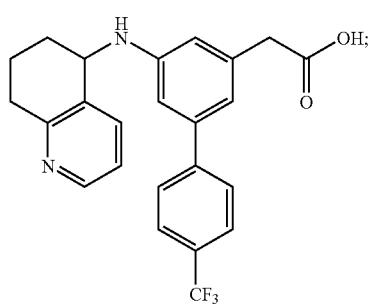
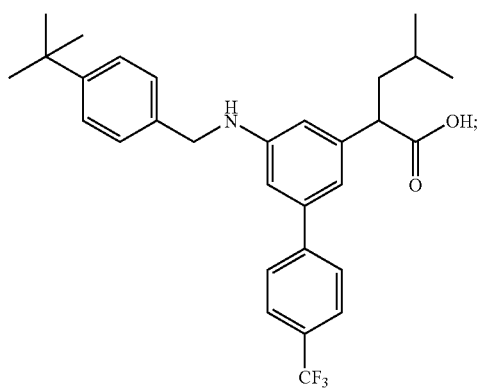
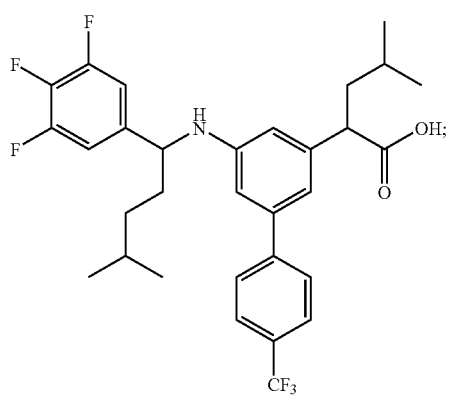
160
-continued
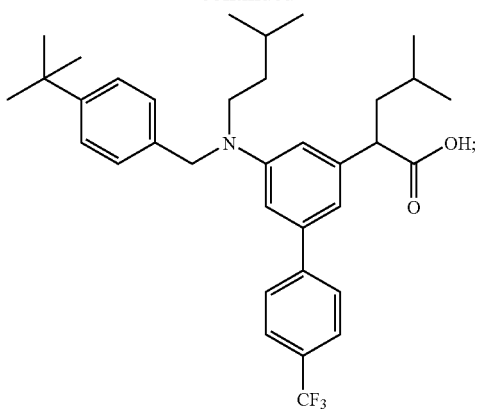
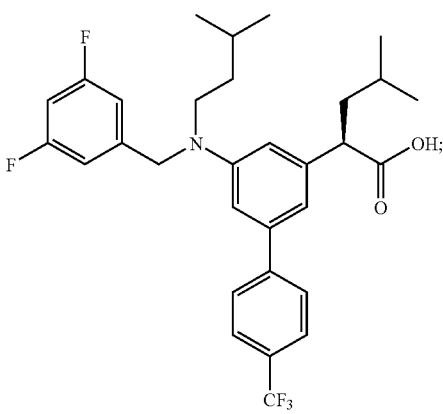
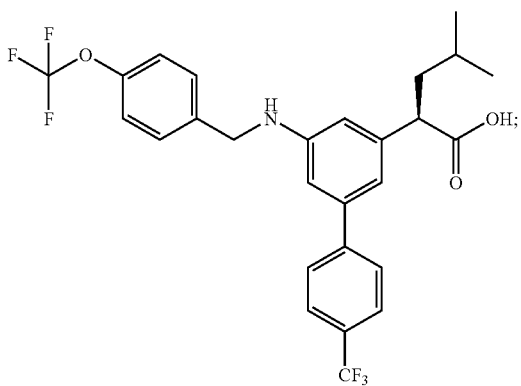
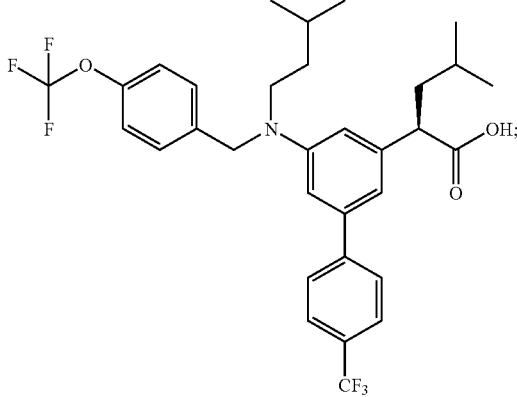

161
-continued
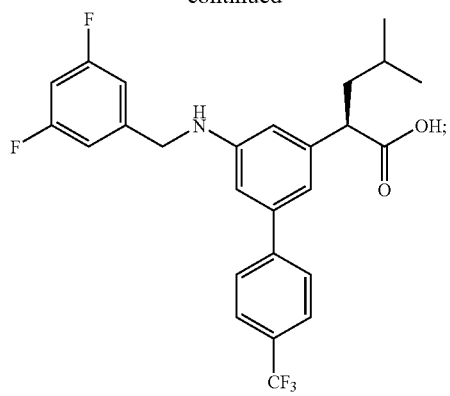
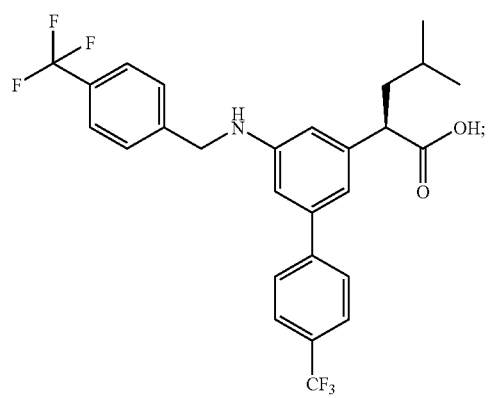
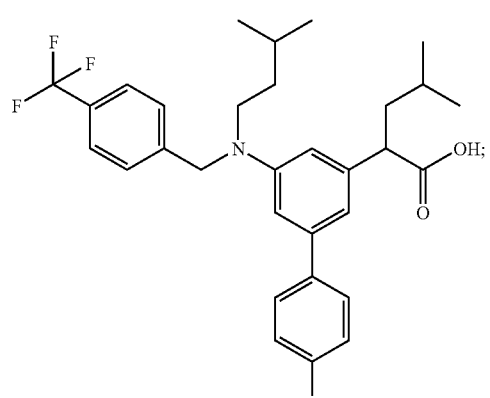
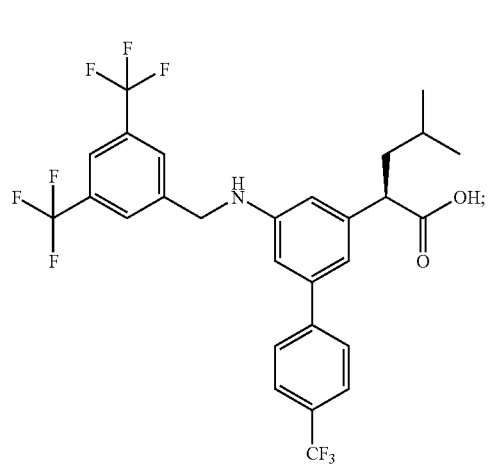
162
-continued
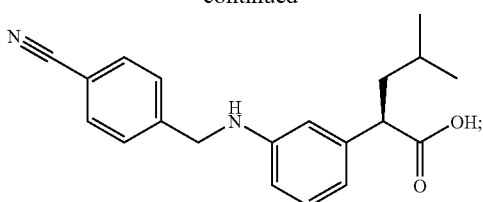
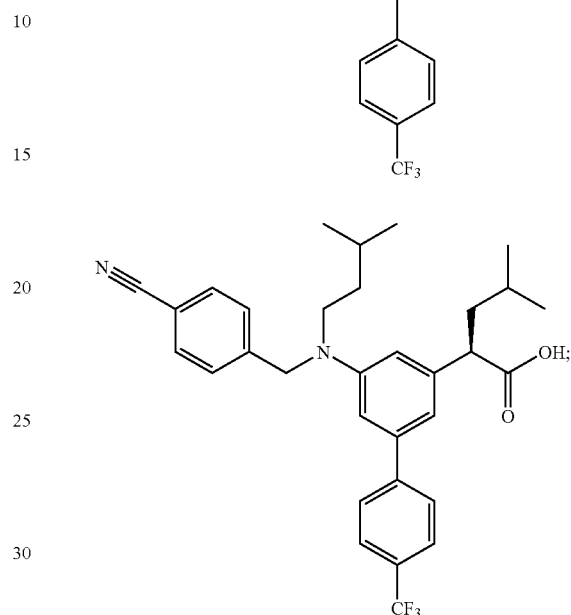
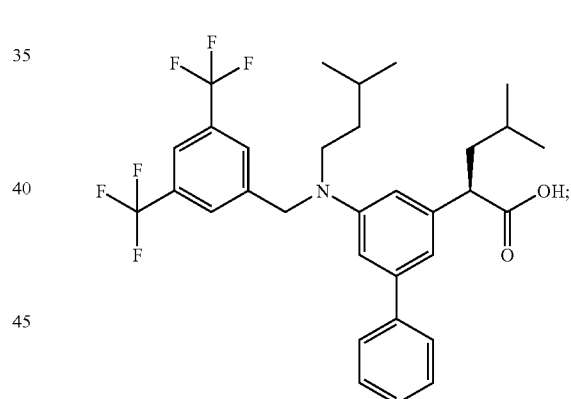
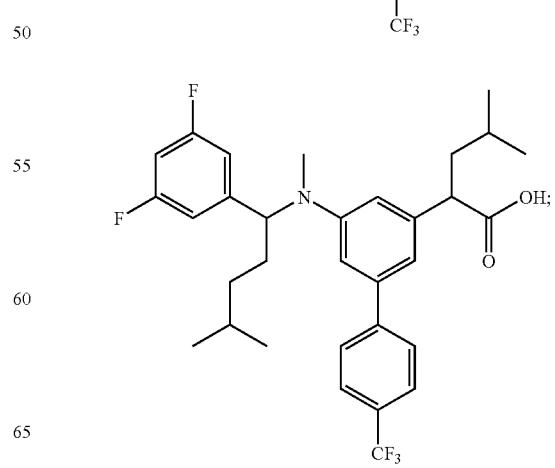

163
-continued
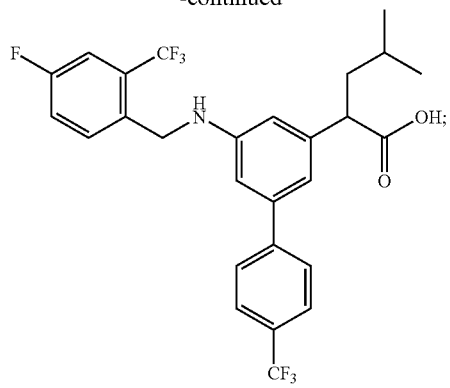
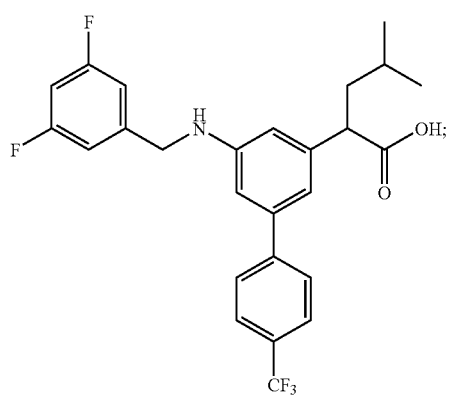
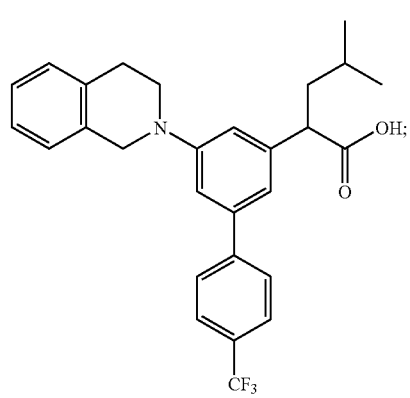
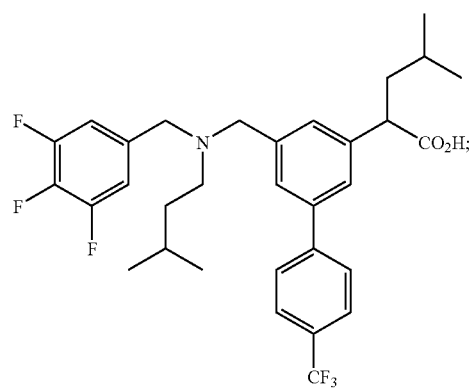
164
-continued
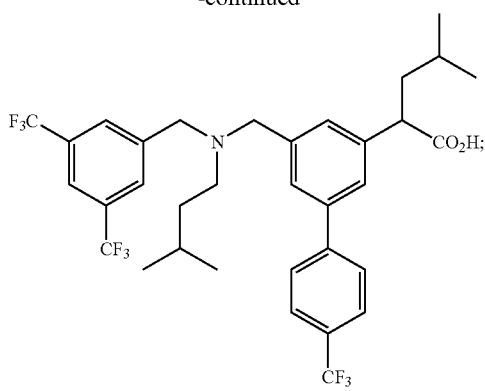
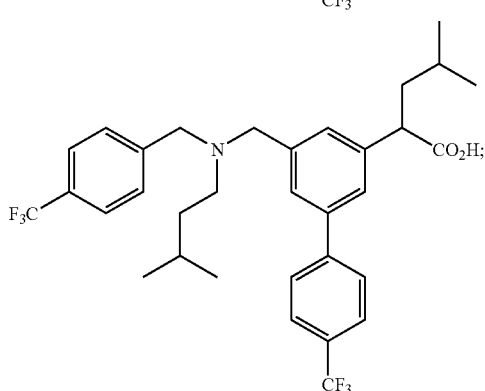
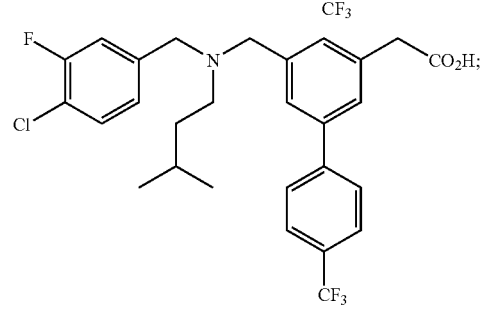
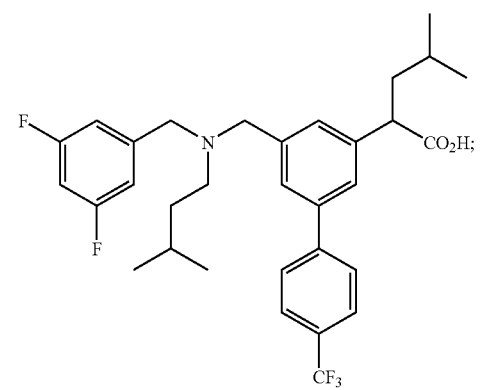

165
-continued
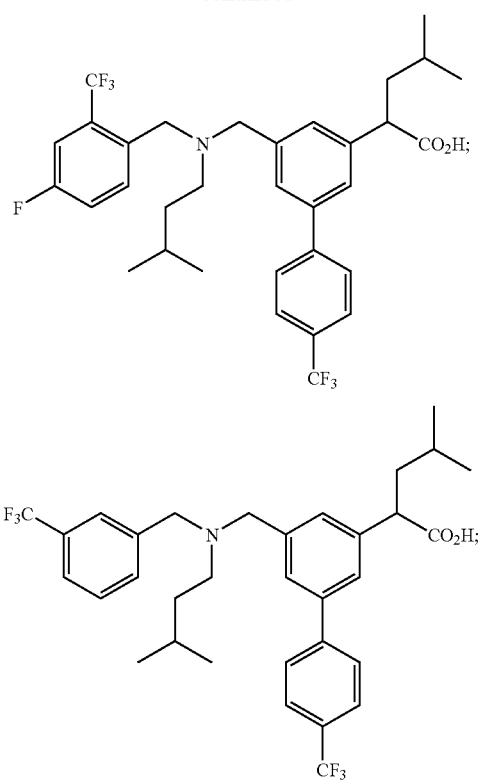
166
-continued
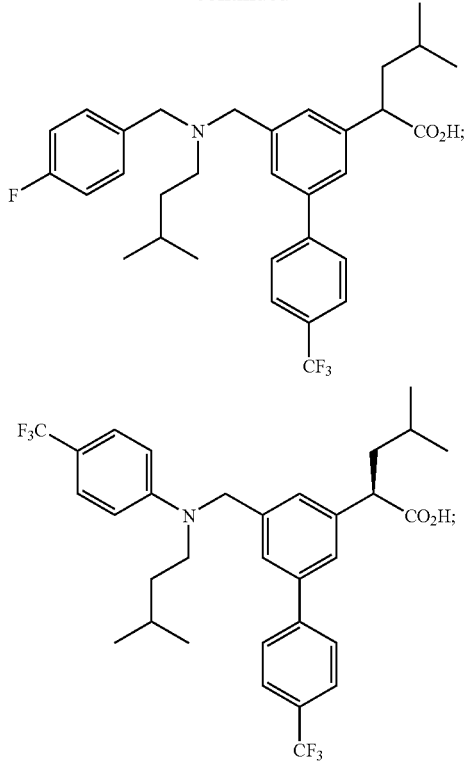
* * * * *